(12) United States Patent
Sawhney et al.

(10) Patent No.: US 8,409,606 B2
(45) Date of Patent: Apr. 2, 2013

(54) DRUG DELIVERY THROUGH HYDROGEL PLUGS

(75) Inventors: Amarpreet S. Sawhney, Lexington, MA (US); Peter Jarrett, Sudbury, MA (US); Michael Bassett, Natick, MA (US); Charles Blizzard, Westwood, MA (US)

(73) Assignee: Incept, LLC, Bedford, MA (US)

( * ) Notice: Subject to any disclaimer, the term of this patent is extended or adjusted under 35 U.S.C. 154(b) by 91 days.

(21) Appl. No.: 12/704,692

(22) Filed: Feb. 12, 2010

(65) Prior Publication Data

US 2010/0209478 A1 Aug. 19, 2010

Related U.S. Application Data

(60) Provisional application No. 61/152,081, filed on Feb. 12, 2009.

(51) Int. Cl.
*A61F 2/00* (2006.01)
*B29B 9/06* (2006.01)
*A01N 43/42* (2006.01)
*A01N 37/08* (2006.01)
*A61K 31/44* (2006.01)
*A61K 31/215* (2006.01)

(52) U.S. Cl. ......... 424/427; 264/118; 514/300; 514/530

(58) Field of Classification Search .................. 424/427; 264/118; 514/300, 530
See application file for complete search history.

(56) References Cited

U.S. PATENT DOCUMENTS

| | | | |
|---|---|---|---|
| 3,161,602 A | 12/1964 | Herbig et al. | |
| 3,423,489 A | 1/1969 | Arens et al. | |
| 3,520,949 A | 7/1970 | Shepard et al. | |
| 3,640,741 A | 2/1972 | Etes | |
| 3,779,942 A | 12/1973 | Bolles | |
| 3,865,108 A | 2/1975 | Hartop | |
| 3,949,073 A | 4/1976 | Daniels et al. | |
| 3,949,750 A * | 4/1976 | Freeman | 424/427 |
| 3,975,350 A | 8/1976 | Hudgin et al. | |
| 3,981,303 A | 9/1976 | Higuchi et al. | |
| 3,991,766 A | 11/1976 | Schmitt et al. | |
| 3,992,562 A | 11/1976 | Denzinger et al. | |
| 4,002,173 A | 1/1977 | Manning et al. | |
| 4,014,335 A | 3/1977 | Arnold | |
| 4,101,380 A | 7/1978 | Rubinstein et al. | |
| 4,107,288 A | 8/1978 | Oppenheim et al. | |
| 4,141,973 A | 2/1979 | Balazs | |
| 4,195,129 A | 3/1980 | Fukui et al. | |
| 4,207,893 A | 6/1980 | Michaels | |
| 4,247,406 A | 1/1981 | Widder et al. | |
| 4,268,495 A | 5/1981 | Muxfeldt et al. | |
| 4,311,146 A | 1/1982 | Wonder | |
| 4,362,567 A | 12/1982 | Schwarz et al. | |
| 4,414,976 A | 11/1983 | Schwarz et al. | |
| 4,424,311 A | 1/1984 | Nagaoka et al. | |
| 4,456,711 A | 6/1984 | Pietsch et al. | |
| 4,472,542 A | 9/1984 | Nambu | |
| 4,507,466 A | 3/1985 | Tomalia et al. | |
| 4,530,840 A | 7/1985 | Tice et al. | |
| 4,532,134 A | 7/1985 | Malette et al. | |
| 4,568,737 A | 2/1986 | Tomalia et al. | |
| 4,597,970 A | 7/1986 | Sharma et al. | |
| 4,631,188 A | 12/1986 | Stoy et al. | |
| 4,646,730 A | 3/1987 | Schonfeld et al. | |
| 4,664,857 A | 5/1987 | Nambu | |
| 4,693,887 A | 9/1987 | Shah | |
| 4,717,378 A | 1/1988 | Perrault et al. | |
| 4,734,097 A | 3/1988 | Tanabe et al. | |
| 4,740,534 A | 4/1988 | Matsuda et al. | |
| 4,741,872 A | 5/1988 | DeLuca et al. | |
| 4,760,131 A | 7/1988 | Sundsmo et al. | |
| 4,803,075 A | 2/1989 | Wallace et al. | |
| 4,804,691 A | 2/1989 | English et al. | |
| 4,826,945 A | 5/1989 | Cohn et al. | |
| 4,828,857 A | 5/1989 | Sharma et al. | |
| 4,837,381 A | 6/1989 | Steber et al. | |
| 4,839,345 A | 6/1989 | Doi et al. | |
| 4,911,926 A | 3/1990 | Henry et al. | |
| 4,925,677 A | 5/1990 | Feijen | |
| 4,938,763 A | 7/1990 | Dunn et al. | |
| 4,952,581 A | 8/1990 | Bio et al. | |
| 4,979,959 A | 12/1990 | Guire | |
| 4,994,277 A | 2/1991 | Higham et al. | |
| 5,024,742 A | 6/1991 | Nesburn et al. | |

(Continued)

FOREIGN PATENT DOCUMENTS

EP 0 732 109 A1 9/1996
EP 1 704 878 A1 9/1996

(Continued)

OTHER PUBLICATIONS

David Lee & Eve Higginbotham, Glaucoma and its Treatment: A Review, 62 Am. J Health Syst. Pharm. 691, 695-96 (2005).*
Geerling et al, "Plugs for Occlusion of the Lacrimal Drainage System", Developments in Ophthalmology, 41:193-212 (2008).
International Search Report (PCT/US2010/024029) dated Nov. 11, 2010.
Atha et al "Mechanism of Precipitation of Proteins by Polyethylene Glycols," J. Biol. Chem. 256(23):12108-12117 (1981).
Bailey et al., "Synthesis of Polymerized Vesicles with Hydrolyzable Linkages," Macromolecules, 25:3-11 (1992).
Burczak et al "Protein Permeation Through Poly(Vinyl Alcohol) Hydrogel Membranes," Biomateria/s 15:231-238 (1994) (abstract).
Dong et al., "Dextran Permeation Through Poly (N-Isopropylacrylamide) Hydrogels," J. Biomater. Sci., Polymer Edn., Bamford, C.H. et al., eds., 5(5):473-484 (1994).

(Continued)

*Primary Examiner* — Sean Basquill
(74) *Attorney, Agent, or Firm* — Dardi & Herbert, PLLC; Curtis B. Herbert

(57) ABSTRACT

An embodiment is a medical prosthesis for blocking or reducing tear flow through a punctum or canaliculus of a human eye and delivering a drug to the eye that comprises a dehydrated covalently crosslinked synthetic hydrophilic polymer hydrogel with dimensions to pass through a puncta lacrimali, with the dehydrated hydrogel absorbing physiological water to swell to at least 1 mm in cross-sectional width and conformably fit a canaliculus, with the hydrogel comprising a therapeutic agent dispersed through the hydrogel for release to an eye, with the hydrogel having a water content of at least about 50% by weight or volume when allowed to fully hydrate in vitro in physiological saline.

23 Claims, 27 Drawing Sheets

U.S. PATENT DOCUMENTS

| | | | |
|---|---|---|---|
| 5,041,292 A | 8/1991 | Feijen | |
| 5,093,319 A | 3/1992 | Higham et al. | |
| 5,100,992 A | 3/1992 | Cohn et al. | |
| 5,104,909 A | 4/1992 | Grasel et al. | |
| 5,122,614 A | 6/1992 | Zalipsky | |
| 5,126,141 A | 6/1992 | Henry | |
| 5,143,662 A | 9/1992 | Chesterfield et al. | |
| 5,152,782 A | 10/1992 | Kowligi et al. | |
| 5,160,745 A | 11/1992 | DeLuca et al. | |
| 5,162,430 A | 11/1992 | Rhee et al. | |
| 5,167,624 A | 12/1992 | Butler et al. | |
| 5,171,148 A | 12/1992 | Wasserman et al. | |
| 5,185,152 A | 2/1993 | Peyman | |
| 5,192,743 A | 3/1993 | Hsu et al. | |
| 5,198,220 A | 3/1993 | Damani | |
| 5,213,580 A | 5/1993 | Slepian et al. | |
| 5,213,760 A | 5/1993 | Dziabo, Jr. et al. | |
| 5,213,808 A | 5/1993 | Bar-Shalom et al. | |
| 5,227,372 A | 7/1993 | Folkman | |
| 5,232,984 A | 8/1993 | Hubbell et al. | |
| 5,266,325 A | 11/1993 | Kuzma et al. | |
| 5,266,326 A | 11/1993 | Barry et al. | |
| 5,278,202 A | 1/1994 | Dunn et al. | |
| 5,281,662 A | 1/1994 | Ito et al. | |
| 5,283,063 A | 2/1994 | Freeman | |
| 5,286,257 A | 2/1994 | Fischer | |
| 5,292,362 A | 3/1994 | Bass et al. | |
| 5,296,228 A | 3/1994 | Chang et al. | |
| 5,296,504 A | 3/1994 | Stjernschantz et al. | |
| 5,296,518 A | 3/1994 | Grasel et al. | |
| 5,304,147 A | 4/1994 | Johnson et al. | |
| 5,304,595 A | 4/1994 | Rhee et al. | |
| 5,306,500 A | 4/1994 | Rhee et al. | |
| 5,324,775 A | 6/1994 | Rhee et al. | |
| 5,328,955 A | 7/1994 | Rhee et al. | |
| 5,330,768 A | 7/1994 | Park et al. | |
| 5,334,137 A | 8/1994 | Freeman | |
| 5,366,498 A | 11/1994 | Brannan et al. | |
| 5,376,375 A | 12/1994 | Rhee et al. | |
| 5,380,536 A | 1/1995 | Hubbell et al. | |
| 5,385,561 A | 1/1995 | Cerny | |
| 5,395,923 A | 3/1995 | Bui-Khac et al. | |
| 5,405,607 A | 4/1995 | Epstein | |
| 5,409,703 A | 4/1995 | McAnalley et al. | |
| 5,410,016 A | 4/1995 | Hubbell et al. | |
| 5,413,791 A | 5/1995 | Rhee et al. | |
| 5,419,491 A | 5/1995 | Breitsprecher | |
| 5,423,821 A | 6/1995 | Pasque | |
| 5,426,148 A | 6/1995 | Tucker | |
| 5,431,639 A | 7/1995 | Shaw | |
| 5,446,090 A | 8/1995 | Harris | |
| 5,446,091 A | 8/1995 | Rhee et al. | |
| 5,455,027 A | 10/1995 | Zalipsky et al. | |
| 5,462,976 A | 10/1995 | Matsuda et al. | |
| 5,462,990 A | 10/1995 | Hubbell et al. | |
| 5,468,811 A | 11/1995 | Moro et al. | |
| 5,470,911 A | 11/1995 | Rhee et al. | |
| 5,475,052 A | 12/1995 | Rhee et al. | |
| 5,480,914 A | 1/1996 | Meadows | |
| 5,509,899 A | 4/1996 | Fan et al. | |
| 5,510,418 A | 4/1996 | Rhee et al. | |
| 5,514,379 A | 5/1996 | Weissleder et al. | |
| 5,514,380 A | 5/1996 | Song et al. | |
| 5,527,856 A | 6/1996 | Rhee et al. | |
| 5,529,914 A | 6/1996 | Hubbell et al. | |
| 5,543,441 A | 8/1996 | Rhee et al. | |
| 5,550,187 A | 8/1996 | Rhee et al. | |
| 5,550,188 A | 8/1996 | Rhee et al. | |
| 5,565,215 A | 10/1996 | Gref et al. | |
| 5,565,519 A | 10/1996 | Rhee et al. | |
| 5,567,435 A | 10/1996 | Hubbell et al. | |
| 5,567,440 A | 10/1996 | Hubbell et al. | |
| 5,573,934 A | 11/1996 | Hubbell et al. | |
| 5,578,638 A | 11/1996 | Brazzell et al. | |
| 5,583,114 A | 12/1996 | Barrows et al. | |
| 5,587,175 A | 12/1996 | Viegas et al. | |
| 5,588,960 A | 12/1996 | Edwards et al. | |
| 5,589,194 A | 12/1996 | Tsuei et al. | |
| 5,605,938 A | 2/1997 | Roufa et al. | |
| 5,612,050 A | 3/1997 | Rowe et al. | |
| 5,612,052 A | 3/1997 | Shalaby | |
| 5,614,587 A | 3/1997 | Rhee et al. | |
| 5,618,563 A | 4/1997 | Berde et al. | |
| 5,624,840 A | 4/1997 | Naughton et al. | |
| 5,626,863 A | 5/1997 | Hubbell et al. | |
| 5,627,233 A | 5/1997 | Hubbell et al. | |
| 5,631,329 A | 5/1997 | Yin et al. | |
| 5,643,464 A | 7/1997 | Rhee et al. | |
| 5,650,173 A | 7/1997 | Ramstack et al. | |
| 5,650,450 A | 7/1997 | Lovette et al. | |
| 5,660,849 A | 8/1997 | Polson et al. | |
| 5,662,712 A | 9/1997 | Pathak et al. | |
| 5,665,063 A | 9/1997 | Roth et al. | |
| 5,665,840 A | 9/1997 | Pohlmann et al. | |
| 5,681,576 A | 10/1997 | Henry | |
| 5,702,361 A | 12/1997 | Evans et al. | |
| 5,702,716 A | 12/1997 | Dunn et al. | |
| 5,705,194 A | 1/1998 | Wong et al. | |
| 5,707,643 A | 1/1998 | Ogura et al. | |
| 5,714,159 A | 2/1998 | Shalaby | |
| 5,717,614 A | 2/1998 | Shah et al. | |
| 5,718,916 A | 2/1998 | Scherr | |
| 5,723,269 A | 3/1998 | Akagi et al. | |
| 5,731,005 A | 3/1998 | Ottoboni et al. | |
| 5,733,950 A | 3/1998 | Dunn et al. | |
| 5,741,292 A | 4/1998 | Mendius | |
| 5,741,323 A | 4/1998 | Pathak et al. | |
| 5,744,545 A | 4/1998 | Rhee et al. | |
| 5,752,974 A | 5/1998 | Rhee et al. | |
| 5,769,882 A | 6/1998 | Fogarty et al. | |
| 5,770,229 A | 6/1998 | Tanihara et al. | |
| 5,773,019 A | 6/1998 | Ashton et al. | |
| 5,773,025 A | 6/1998 | Baichwal | |
| 5,776,445 A | 7/1998 | Cohen et al. | |
| 5,776,493 A | 7/1998 | Barclay et al. | |
| 5,786,421 A | 7/1998 | Rhee et al. | |
| 5,800,373 A | 9/1998 | Melanson et al. | |
| 5,800,541 A | 9/1998 | Rhee et al. | |
| 5,801,033 A | 9/1998 | Hubbell et al. | |
| 5,807,581 A | 9/1998 | Rosenblatt et al. | |
| 5,814,621 A | 9/1998 | Kanaya et al. | |
| 5,820,882 A | 10/1998 | Hubbell et al. | |
| 5,830,171 A | 11/1998 | Wallace | |
| 5,830,178 A | 11/1998 | Jones et al. | |
| 5,830,196 A | 11/1998 | Hicks et al. | |
| 5,834,274 A | 11/1998 | Hubbell et al. | |
| 5,837,226 A | 11/1998 | Jungherr et al. | |
| 5,843,743 A | 12/1998 | Hubbell et al. | |
| 5,844,016 A | 12/1998 | Sawhney et al. | |
| 5,844,023 A | 12/1998 | Tomka | |
| 5,849,035 A | 12/1998 | Pathak et al. | |
| 5,849,412 A | 12/1998 | Bromberg et al. | |
| 5,849,839 A | 12/1998 | Hubbell et al. | |
| 5,851,508 A | 12/1998 | Greff et al. | |
| 5,858,746 A | 1/1999 | Hubbell et al. | |
| 5,869,096 A | 2/1999 | Barclay et al. | |
| 5,874,500 A | 2/1999 | Rhee et al. | |
| 5,879,688 A | 3/1999 | Coury et al. | |
| 5,888,493 A | 3/1999 | Sawaya | |
| 5,900,245 A | 5/1999 | Sawhney et al. | |
| 5,932,462 A | 8/1999 | Harris et al. | |
| 5,936,035 A | 8/1999 | Rhee et al. | |
| 5,962,023 A | 10/1999 | Jamiolkowski et al. | |
| 5,972,375 A | 10/1999 | Truter et al. | |
| 5,973,014 A | 10/1999 | Funk et al. | |
| 5,981,607 A | 11/1999 | Ding et al. | |
| 5,986,043 A | 11/1999 | Hubbell et al. | |
| 5,990,193 A | 11/1999 | Russell et al. | |
| 6,017,301 A | 1/2000 | Schwartz et al. | |
| 6,046,305 A | 4/2000 | Choi | |
| 6,051,248 A | 4/2000 | Sawhney et al. | |
| 6,051,648 A | 4/2000 | Rhee et al. | |
| 6,060,582 A | 5/2000 | Hubbell et al. | |
| 6,071,875 A | 6/2000 | Clark et al. | |
| 6,082,362 A | 7/2000 | Webb | |
| 6,083,524 A | 7/2000 | Sawhney et al. | |
| 6,110,484 A | 8/2000 | Sierra | |

| | | | |
|---|---|---|---|
| 6,121,341 A | 9/2000 | Sawhney et al. | |
| 6,123,667 A | 9/2000 | Poff et al. | |
| 6,129,761 A | 10/2000 | Hubbell et al. | |
| 6,132,986 A | 10/2000 | Pathak et al. | |
| 6,149,614 A | 11/2000 | Dunshee et al. | |
| 6,149,931 A | 11/2000 | Schwartz et al. | |
| 6,152,943 A | 11/2000 | Sawhney | |
| 6,153,211 A | 11/2000 | Hubbell et al. | |
| 6,154,671 A | 11/2000 | Parel et al. | |
| 6,156,345 A | 12/2000 | Chudzik et al. | |
| 6,156,531 A | 12/2000 | Pathak et al. | |
| 6,162,241 A | 12/2000 | Coury et al. | |
| 6,165,201 A | 12/2000 | Sawhney et al. | |
| 6,165,489 A | 12/2000 | Berg et al. | |
| 6,166,130 A | 12/2000 | Rhee et al. | |
| 6,171,600 B1 | 1/2001 | Dahms | |
| 6,176,871 B1 | 1/2001 | Pathak et al. | |
| 6,177,095 B1 | 1/2001 | Sawhney et al. | |
| 6,177,514 B1 | 1/2001 | Pathak et al. | |
| 6,179,862 B1 | 1/2001 | Sawhney | |
| 6,196,993 B1 * | 3/2001 | Cohan et al. | 604/891.1 |
| 6,201,065 B1 | 3/2001 | Pathak et al. | |
| 6,206,930 B1 | 3/2001 | Burg et al. | |
| 6,214,966 B1 | 4/2001 | Harris | |
| 6,217,896 B1 | 4/2001 | Benjamin | |
| 6,220,246 B1 | 4/2001 | Chandler et al. | |
| 6,231,892 B1 | 5/2001 | Hubbell et al. | |
| 6,242,442 B1 | 6/2001 | Dean et al. | |
| 6,251,382 B1 | 6/2001 | Greenwald et al. | |
| 6,258,351 B1 | 7/2001 | Harris | |
| 6,258,870 B1 | 7/2001 | Hubbell et al. | |
| 6,261,544 B1 | 7/2001 | Coury et al. | |
| 6,277,394 B1 | 8/2001 | Sierra | |
| 6,283,991 B1 | 9/2001 | Cox et al. | |
| 6,287,588 B1 | 9/2001 | Shih et al. | |
| 6,290,729 B1 | 9/2001 | Slepian et al. | |
| 6,297,240 B1 | 10/2001 | Embleton | |
| 6,303,102 B1 | 10/2001 | Schlichte | |
| 6,306,922 B1 | 10/2001 | Hubbell et al. | |
| 6,312,725 B1 | 11/2001 | Wallace et al. | |
| 6,316,441 B1 | 11/2001 | Dean et al. | |
| 6,319,240 B1 | 11/2001 | Beck | |
| 6,322,593 B1 | 11/2001 | Pathak et al. | |
| 6,323,278 B2 | 11/2001 | Rhee et al. | |
| 6,331,313 B1 | 12/2001 | Wong et al. | |
| 6,335,335 B2 | 1/2002 | Higashiyama et al. | |
| 6,352,682 B2 | 3/2002 | Leavitt et al. | |
| 6,371,975 B2 | 4/2002 | Cruise et al. | |
| 6,379,373 B1 | 4/2002 | Sawhney | |
| 6,387,977 B1 | 5/2002 | Sawhney et al. | |
| 6,409,757 B1 | 6/2002 | Trout, III et al. | |
| 6,410,045 B1 | 6/2002 | Schultz et al. | |
| 6,410,645 B1 | 6/2002 | Pathak et al. | |
| 6,413,539 B1 | 7/2002 | Shalaby | |
| 6,416,740 B1 | 7/2002 | Unger | |
| 6,458,147 B1 | 10/2002 | Cruise et al. | |
| 6,458,889 B1 | 10/2002 | Trollsas et al. | |
| 6,465,001 B1 | 10/2002 | Hubbell et al. | |
| 6,475,508 B1 | 11/2002 | Schwartz et al. | |
| 6,479,079 B1 | 11/2002 | Pathak et al. | |
| 6,495,127 B1 | 12/2002 | Wallace et al. | |
| 6,503,731 B2 | 1/2003 | Marx et al. | |
| 6,514,534 B1 | 2/2003 | Sawhney | |
| 6,517,824 B1 | 2/2003 | Kohn et al. | |
| 6,528,107 B2 | 3/2003 | Chinn et al. | |
| 6,534,591 B2 | 3/2003 | Rhee et al. | |
| 6,539,251 B2 | 3/2003 | Beck et al. | |
| 6,566,406 B1 | 5/2003 | Pathak et al. | |
| 6,569,463 B2 | 5/2003 | Patel et al. | |
| 6,579,519 B2 | 6/2003 | Maitra et al. | |
| 6,589,549 B2 | 7/2003 | Shih et al. | |
| 6,596,471 B2 | 7/2003 | Pathak et al. | |
| 6,602,975 B2 | 8/2003 | Hubbell et al. | |
| 6,605,294 B2 | 8/2003 | Sawhney | |
| 6,610,033 B1 | 8/2003 | Melanson et al. | |
| 6,624,245 B2 | 9/2003 | Wallace et al. | |
| 6,632,446 B1 | 10/2003 | Hubbell et al. | |
| 6,632,457 B1 | 10/2003 | Sawhney | |
| 6,639,014 B2 | 10/2003 | Pathak et al. | |
| 6,656,200 B2 | 12/2003 | Li et al. | |
| 6,673,093 B1 | 1/2004 | Sawhney | |
| 6,679,605 B2 | 1/2004 | Zhou et al. | |
| 6,689,148 B2 | 2/2004 | Sawhney et al. | |
| 6,692,759 B1 | 2/2004 | Wong et al. | |
| 6,699,493 B2 | 3/2004 | Wong | |
| 6,703,047 B2 | 3/2004 | Sawhney et al. | |
| 6,709,668 B2 | 3/2004 | Won et al. | |
| 6,710,126 B1 | 3/2004 | Hirt et al. | |
| 6,719,750 B2 | 4/2004 | Varner et al. | |
| 6,747,090 B2 | 6/2004 | DeGroot et al. | |
| 6,777,000 B2 | 8/2004 | Ni et al. | |
| 6,818,018 B1 | 11/2004 | Sawhney | |
| 6,833,408 B2 | 12/2004 | Sehl et al. | |
| 6,861,065 B2 | 3/2005 | Hodd et al. | |
| 6,887,974 B2 | 5/2005 | Pathak | |
| 6,902,743 B1 | 6/2005 | Setterstrom et al. | |
| 6,905,700 B2 | 6/2005 | Won et al. | |
| 6,911,227 B2 | 6/2005 | Hubbell et al. | |
| 6,911,496 B2 | 6/2005 | Rhee et al. | |
| 6,916,857 B2 | 7/2005 | Won et al. | |
| 6,923,986 B2 | 8/2005 | Pathak et al. | |
| 6,923,988 B2 | 8/2005 | Patel et al. | |
| 6,936,005 B2 | 8/2005 | Poff et al. | |
| 6,958,212 B1 | 10/2005 | Hubbell et al. | |
| 6,962,979 B1 | 11/2005 | Rhee | |
| 7,009,034 B2 | 3/2006 | Pathak et al. | |
| 7,017,580 B2 | 3/2006 | Prescott et al. | |
| 7,025,990 B2 | 4/2006 | Sawhney | |
| 7,057,019 B2 | 6/2006 | Pathak | |
| 7,060,297 B2 | 6/2006 | Karakelle et al. | |
| 7,129,210 B2 | 10/2006 | Lowinger et al. | |
| 7,141,248 B2 | 11/2006 | Hodd et al. | |
| 7,153,519 B2 | 12/2006 | Hubbell et al. | |
| 7,211,651 B2 | 5/2007 | Pathak | |
| 7,220,270 B2 | 5/2007 | Sawhney et al. | |
| RE39,713 E | 7/2007 | Sawhney et al. | |
| 7,238,364 B2 | 7/2007 | Sawhney et al. | |
| 7,247,314 B2 | 7/2007 | Hnojewyj et al. | |
| 7,273,896 B2 | 9/2007 | Daniloff et al. | |
| 7,332,566 B2 | 2/2008 | Pathak et al. | |
| 7,413,752 B2 | 8/2008 | Sawhney | |
| 7,589,057 B2 | 9/2009 | Chang et al. | |
| 7,648,713 B2 | 1/2010 | Sawhney | |
| 7,998,497 B2 * | 8/2011 | de Juan et al. | 424/423 |
| 2002/0026176 A1 | 2/2002 | Varner et al. | |
| 2002/0064513 A1 | 5/2002 | Maitra et al. | |
| 2002/0071869 A1 | 6/2002 | Bures et al. | |
| 2002/0071874 A1 | 6/2002 | Olejnik et al. | |
| 2002/0114778 A1 | 8/2002 | Xia et al. | |
| 2002/0119941 A1 | 8/2002 | Ni et al. | |
| 2002/0197300 A1 | 12/2002 | Schultz et al. | |
| 2003/0012734 A1 | 1/2003 | Pathak et al. | |
| 2003/0017199 A1 | 1/2003 | Woodward et al. | |
| 2003/0108511 A1 * | 6/2003 | Sawhney | 424/78.08 |
| 2003/0143280 A1 | 7/2003 | El-Sherif et al. | |
| 2003/0147849 A1 | 8/2003 | Warne et al. | |
| 2003/0175324 A1 | 9/2003 | Robinson et al. | |
| 2003/0185892 A1 | 10/2003 | Bell et al. | |
| 2003/0191426 A1 | 10/2003 | Lerner et al. | |
| 2004/0009205 A1 | 1/2004 | Sawhney | |
| 2004/0037889 A1 | 2/2004 | Richeal et al. | |
| 2004/0063206 A1 | 4/2004 | Rowley et al. | |
| 2004/0076602 A1 | 4/2004 | Harris | |
| 2004/0086479 A1 | 5/2004 | Grinstaff et al. | |
| 2004/0121905 A1 | 6/2004 | Ranganathan et al. | |
| 2004/0131582 A1 | 7/2004 | Grinstaff et al. | |
| 2004/0147016 A1 | 7/2004 | Rowley et al. | |
| 2004/0175410 A1 * | 9/2004 | Ashton et al. | 424/427 |
| 2004/0228862 A1 | 11/2004 | Shelton et al. | |
| 2004/0230183 A1 | 11/2004 | Breegi et al. | |
| 2005/0043220 A1 | 2/2005 | Guyer et al. | |
| 2005/0080445 A1 | 4/2005 | Sawhney et al. | |
| 2005/0089545 A1 | 4/2005 | Kuwano et al. | |
| 2005/0169882 A1 | 8/2005 | Lowe et al. | |
| 2005/0197614 A1 * | 9/2005 | Pritchard et al. | 604/8 |
| 2005/0208095 A1 | 9/2005 | Hunter et al. | |
| 2005/0232872 A1 | 10/2005 | Deaver et al. | |
| 2005/0232972 A1 | 10/2005 | Odrich | |

| | | |
|---|---|---|
| 2005/0238692 A1 | 10/2005 | Hughes |
| 2005/0244464 A1 | 11/2005 | Hughes |
| 2005/0244467 A1 | 11/2005 | Nivaggioli et al. |
| 2005/0255144 A1 | 11/2005 | Schultz |
| 2005/0271727 A1 | 12/2005 | Yao |
| 2005/0277864 A1 | 12/2005 | Haffner et al. |
| 2006/0002963 A1 | 1/2006 | Rabinovich-Guilatt et al. |
| 2006/0013859 A1 | 1/2006 | Yamada et al. |
| 2006/0024350 A1 | 2/2006 | Varner et al. |
| 2006/0034930 A1 | 2/2006 | Khosravi et al. |
| 2006/0039479 A1 | 2/2006 | Francois et al. |
| 2006/0039979 A1 | 2/2006 | Yamada et al. |
| 2006/0057222 A1 | 3/2006 | Linhardt et al. |
| 2006/0074370 A1 | 4/2006 | Zhou |
| 2006/0079599 A1 | 4/2006 | Arthur |
| 2006/0099238 A1 | 5/2006 | Khosravi et al. |
| 2006/0100288 A1 | 5/2006 | Bague et al. |
| 2006/0147409 A1 | 7/2006 | Pathak et al. |
| 2006/0177481 A1 | 8/2006 | Sawhney |
| 2006/0182771 A1 | 8/2006 | Dor et al. |
| 2006/0182781 A1 | 8/2006 | Hughes et al. |
| 2006/0182783 A1 | 8/2006 | Hughes et al. |
| 2006/0193899 A1 | 8/2006 | Sawhney |
| 2006/0258698 A1 | 11/2006 | Mudumba et al. |
| 2006/0286173 A1 | 12/2006 | Yamada et al. |
| 2007/0021762 A1 | 1/2007 | Liu et al. |
| 2007/0160647 A1 | 7/2007 | Pritchard et al. |
| 2007/0185033 A1 | 8/2007 | Gefter et al. |
| 2007/0195261 A1 | 8/2007 | Vogt et al. |
| 2007/0196497 A1 | 8/2007 | Pouliquen et al. |
| 2007/0197776 A1 | 8/2007 | Pathak |
| 2007/0202186 A1 | 8/2007 | Yamamoto et al. |
| 2007/0224246 A1 | 9/2007 | Hughes et al. |
| 2007/0231366 A1 | 10/2007 | Sawhney et al. |
| 2007/0233240 A1 | 10/2007 | Frank et al. |
| 2007/0243230 A1 | 10/2007 | de Juan, Jr. et al. |
| 2007/0248567 A1 | 10/2007 | Pathak et al. |
| 2007/0270345 A1 | 11/2007 | Gardner et al. |
| 2007/0275027 A1 | 11/2007 | Wen et al. |
| 2007/0282366 A1 | 12/2007 | Khosravi et al. |
| 2008/0014144 A1 | 1/2008 | Saltzman et al. |
| 2008/0038316 A1 | 2/2008 | Wong et al. |
| 2008/0038317 A1 | 2/2008 | Chang et al. |
| 2008/0045911 A1* | 2/2008 | Borgia et al. ............ 604/294 |
| 2008/0114092 A1 | 5/2008 | Sawhney |
| 2008/0124376 A1 | 5/2008 | Pruitt et al. |
| 2008/0124389 A1 | 5/2008 | Jenkins et al. |
| 2008/0124400 A1* | 5/2008 | Liggins et al. ............ 424/501 |
| 2008/0132444 A1 | 6/2008 | Li et al. |
| 2008/0171091 A1 | 7/2008 | Wood et al. |
| 2008/0220047 A1 | 9/2008 | Sawhney et al. |
| 2008/0233173 A1 | 9/2008 | Whitcup et al. |
| 2008/0241223 A1 | 10/2008 | Nivaggioli et al. |
| 2008/0268020 A1 | 10/2008 | Philips et al. |
| 2009/0017097 A1 | 1/2009 | Sawhney et al. |
| 2009/0104248 A1 | 4/2009 | Rapacki et al. |
| 2009/0105749 A1 | 4/2009 | de Juan et al. |
| 2009/0118702 A1 | 5/2009 | Lazar |
| 2009/0215923 A1 | 8/2009 | Carnahan et al. |
| 2009/0227981 A1* | 9/2009 | Bennett .................. 604/511 |
| 2009/0240276 A1 | 9/2009 | Ainpour et al. |
| 2009/0264861 A1 | 10/2009 | Jain et al. |
| 2010/0036488 A1 | 2/2010 | de Juan, Jr. et al. |
| 2010/0104654 A1 | 4/2010 | Robinson et al. |
| 2010/0158980 A1 | 6/2010 | Kopczynski et al. |
| 2011/0196317 A1 | 8/2011 | Lust et al. |

FOREIGN PATENT DOCUMENTS

| | | |
|---|---|---|
| EP | 1967220 A2 | 9/2008 |
| WO | 94/25080 A1 | 11/1994 |
| WO | 97/05185 A2 | 2/1997 |
| WO | 97/19973 A1 | 6/1997 |
| WO | 97/22371 A1 | 6/1997 |
| WO | 97/39781 A1 | 10/1997 |
| WO | 98/12274 A1 | 3/1998 |
| WO | 98/35631 A1 | 8/1998 |
| WO | 99/03454 A1 | 1/1999 |
| WO | 99/22770 A | 5/1999 |
| WO | 99/34833 A1 | 7/1999 |
| WO | 99/62510 A2 | 12/1999 |
| WO | 00/09199 A1 | 2/2000 |
| WO | 0009088 A1 | 2/2000 |
| WO | 2004/028404 A2 | 4/2004 |
| WO | 2005086694 A2 | 9/2005 |
| WO | 2006/026325 A2 | 3/2006 |
| WO | 2006/031358 A2 | 3/2006 |
| WO | 2006/031388 A2 | 3/2006 |
| WO | 2006/096586 A1 | 9/2006 |
| WO | 2007/001926 A2 | 1/2007 |
| WO | 2007/005249 A2 | 1/2007 |
| WO | 2007115259 A2 | 10/2007 |
| WO | 2008/035376 A2 | 3/2008 |

OTHER PUBLICATIONS

Farokhzad et al., "Targeted nanoparticle-aptamer bioconjugates for cancer chemotherapy in vivo", PNAS, 103 (16):6315-6320 (Apr. 18, 2005).

Farokhzad et al, "Nanoparticle-Aptamer Bioconjugates: A New Approach for Targeting Prostate Cancer Cells", Cancer Research, 64:7668-7672 (Nov. 1, 2004).

Galeska et al., "Controlled Release of Dexamethasone from PLGA Microspheres Embedded Within Polyacid—Containing PVA Hydrogels", AAPS Journal 2005:7(1):E231-E240 (Sep. 2, 2005).

Gander et al., "Crosslinked Poly(alkylene Oxides) for the Preparation of Controlled Release Micromatrices", Journal of Controlled Release, 5:271-283 (1988).

Gayet et al, "High Water Content BSA-PEG Hydrogel for Controlled Release Device: Evaluation of the Drug Release Properties", Journal of Controlled Release, 38:177-184 (1996).

Hill-West et al., "Prevention of Postoperative Adhesions in the Rat by in Situ Photopolymerization of Bioresorbably Hydrogel Barriers," Obstetrics and Gynecology, 83(1): 59-64 (1994).

Hyon, "Biodegradable Poly(Lactic Acid) Microsphers for Drug Delivery Systems", Yonsei Medical Journal, 41 (6):720-734 (2000).

Jarrett et al, "Bioabsorbable Hydrogel Tissue Barrier: In Situ Gelation Kinetics," Soc. for Biomater., Transactions of 21st Annual Meeting: 182 (1995).

Kimura et al., "Injectable Microsphers with Controlled Drug Release for Glaucoma Filtering Surger", Invest. Opthalmol & Visual Sci., 33(12): 3436-3441 (Nov. 1992).

Klibanov et al., "Activity of Amphipathic Poly (ethylene glycol) 5000 to Prolong the Circulation Time of Liposomes Depends on the Liposome Size and is Unfavorable for Immunoliposome Binding to Target," Biochimica et Biophysica Acta, 1062:142-148 (1991).

Kissel et al., "Parenteral depot-systems on the basis of biodegradable polyesters," Journal of Controlled Release 16:27-42 (1991).

Kissell et al. "ABA-triblock Copolymers from Biodegradable Polyester A-blocks and Hydrophilic Poly(ethylene ) xide) B-Blocks as a Candidate for in Situ Forming Hydrogel Delivery Systems for Proteins" Advanced Drug Delivery Reviews, 54:99-134 (2002).

Lasic et al., "Sterically Stabilized Liposomes: A Hypothesis on the Molecular Origin of the Extended Circulation Times," Biochimica et Biophysica Acta, 1070:187-192 (1991).

Mathiowitz et al., "Polyanhydride Microspheres As Drug Carriers I. Hot-Melt Microencapsulation", J Controlled Release 5:13-22 (1987).

Mayhew et al., "Characterization of Liposomes Prepared by Using a Microemulsifier," Biochimica et Biophysica Acta, 775:169-174 (1984).

Mettler et al., "A Prospective Clinical Trial of SprayGel as a Barrier to Adhesion Formation: An Interim Analysis", The Journal of the American Association of Gynecologic Laparoscopists, 10(3):339-344 (Aug. 2003).

Mordenti et al.., "Intraocular Pharmokinetics and Safety of a Huumanized Monocloona Antibody in Rabbits After Intravitreal Administration of a Solution or a PLGA Microsphere Formulation", Toxicollogial Sciences, 52:101-106 (1999).

Nihant et al., "Polylactide Microparticles Prepared by Double Emulsion-Evaporation", J. Colloid & Interface Science 173:55-65 (1995).

Park et al., Biodegradable Hydrogels for Drug Delivery, Technomic Publishing Co., Inc., Lancaster, PA (1993).

Park, "Enzyme-Digestible Swelling Hydrogels as Platforms for Long-Term Oral Drug Delivery: Synthesis and Characterization," Biomaterials, 9:435-441 (1988).

Reddy et al., "Polyurethane Microspheres as Drug Carriers", Macromolecular Reports A32:789-799 (1995).

Sawhney et al., "Bioerodible Hydrogels Based on Photopolymerized Poly(ethylene glycol)-co-poly(α-hydroxy acid) Diacrylate Macromers," Macromolecules, 26:581-587 (1993).

Sawhney et al., "Optimization of Photopolymerized Bioerodible Hydrogel Properties for Adhesion Prevention", Journal of Biomedical Materials Research, 28:831-838 (1994).

Shalaby et al., "In Vitro and in Vivo Studies of Enzyme-Digestible Hydrogels for Oral Drug Delivery," J. Controlled Release, 19:131-144 (1992).

Shalaby, "Bioabsorbable Polymers," Encyclopedia of Pharmaceutical Technology, Swarbrick, J. et al., eds., Marcel Dekker, Inc., New York, 1:465-476 (1988).

Tabata et al., "Controlled Delivery Systems for Proteins Using Polyanhydride Microspheres," Pharmaceutical Research 10:487-496 (1993).

Torchilin et al., "Liposome-Polymer Systems. Introduction of Liposomes into a Polymer Gel and Preparation of the Polymer Gel Inside a Liposome," Polymer Sci. U.S.S.R., 30(10): 2307-2312 (1988).

Roberts,"Penetration of the fourth-generation fluoroquinolones: consider risks vs. benefits," Therapeutic Updates in Ophthalmology 6, 1-4 (2005).

Passerini et al.,"An investigation into the effects of residual water on the glass transition temperature of polyactide microspheres using modulated temperature DSC," Journal of Controlled Release, 73, 111-115 (2001).

Communications from U.S. Appl. No. 11/825,848 dated from Mar. 31, 2009 to Apr. 6, 2010.

Jain et al. "Lessons from phase III clinical trials on anti-VEGF therapy for cancer" Nature Clinical Practice Oncology, vol. 3 No. 1 Jan. 2006, pp. 24-40.

Al-Aswad "Another Role for Avastin? Neovascular Glasucoma" Review of Ophthalmology Online, http://www.revophth.com/content/d/cover_focus/i/1304/c/25094, Jun. 13, 2006, 5 pages.

Supplementary European Search Report from corresponding EP Patent Application No. 10741771.9 dated Aug. 22, 2012 (9 pages).

Zustiak et al., "Characterization of protein release from hydrolytically degradable poly(ehtylene glycol) hydrogels", Biotechnology and Bioenginering 108 (2011) 197-206.

Bos et al., "Controlled release of pharmaceutical proteins from hydrogels", Business Briefing Pharmatech (2002) 1-5.

Hoare et al., "Hydrogels in drug delivery: progress and challenges", ScienceDirect Polymer 49 (2008) 1993-2007.

Herrmann, "Lipidic implants for pharmaceutical proteins: mechanisms of release and development of extruded devices", Dissertation Ludwig-Maximilians-Univiversity, Munich Germany (2007) 1-220.

Dunn et al., "Evaluation of the SprayGel adhesion barrier in the rat cecum abrasion and rabbit uterine horn adhesion models", Fertility and Sterility, 75(2): 411-416 (Feb. 2001).

Dunn et al., "Rat (Abdominal) & Rat (Pelvic) Studies", Efficacy Preclinical Studies brochure, 2000.

Ferland et al., "Porcine (Pelvic) Efficacy Studies", Efficacy Preclinical Studies brochure, 2000.

Internet Archive, Search results for (http://chemistry2.csudh.edu/rpedarvis/AmAcSeqSyn.html., Accessed Mar. 23, 2009.

Lou et al., "Drug release characteristics of phase separation pHEMA sponge materials", Biomaterials, 25:5071-5080 (2004).

Neises et al., "Esterification of Carboxylic Acids with Dicyclohexylcarbodiimide/4-Dimethylaminopyridime: tert-Butyl Ethyl Fumarate", 63 Org. Synth. Coll. 183 (1985).

Office Action dated Aug. 5, 2009.

Peptide Sequencing and Synthesis"Chemistry 240 Summer 2001.", May 8, 2003 (as of Internet Archive). Http://chemistry2csudh.edu/rpendarvis/Am/AcSeqSyn.html.

Sawhney et al., "Rabbit (Pericardial) Adhesion Study", Efficacy Preclinical Studies brochure, 2000.

Srividya et al., "Sustained Ophthalmic Delivery of Ofloxacin from a pH Triggered in Situ Gellng System", Journal of Controlled Release, 73:205-211 (2001).

Sawhney et al., File History U.S. Appl. No. 11/825,848, 2007.

US 6,214,374, 04/2001, Schmirler et al. (withdrawn)

* cited by examiner

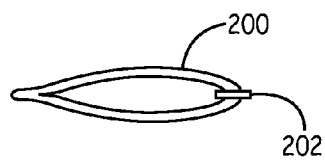
FIG. 2A
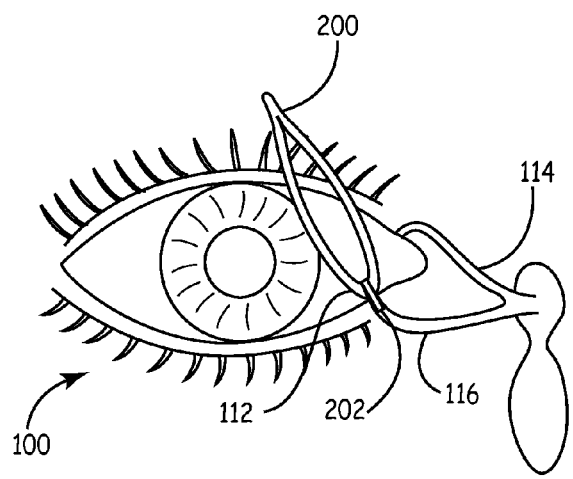
FIG. 2B
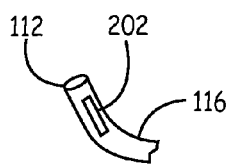 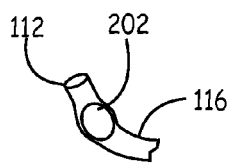 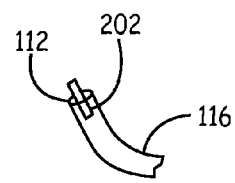 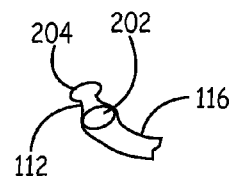
FIG. 2C   FIG. 2D   FIG. 2E   FIG. 2F See Example 11 Change in Volume for plugs made using MeOH and WFI.

DRUG DELIVERY THROUGH HYDROGEL PLUGS

CROSS REFERENCE TO RELATED APPLICATIONS

This application claims priority to U.S. 61/152,081 filed Feb. 12, 2009, which is hereby incorporated herein by reference for all purposes.

TECHNICAL FIELD

The technical field relates broadly to ophthalmologic prostheses, and more particularly to medical canalicular inserts such as punctum plugs.

BACKGROUND

Drug delivery to the eye is conventionally accomplished by periodic administration of eye drops, pastes-and-bandages, lenses impregnated with drugs applied to the cornea, direct injection, or drug depots inserted into the eye. For example, after cataract and vitreoretinal surgery, antibiotics may need to be administered every few hours for several days. In addition, other drugs such as non-steroidal anti inflammatory drugs (NSAIDS) may also need to be given frequently.

SUMMARY OF THE INVENTION

In general, ocular drugs for treating an eye disease or condition are directed to treat ocular surface conditions, anterior segment diseases, or posterior/back-of-the-eye diseases.

Most drugs that are delivered to the ocular surface and the front of the eye are administered in the form of eye drops. There are several problems with this form of delivery. Firstly, for older patients who may be arthritic, getting the drop into the eye can be difficult. Secondly, it has been estimated that upwards of 95% of the medication in the drop does not end up penetrating the eye and is wasted. This wastage not only results in inefficient utilization of the drug, but also can lead to systemic side effects (e.g., beta blockers for glaucoma may lead to cardiovascular problems). Finally, to be able to achieve the required therapeutic level, a user has to administer larger concentrations of drugs, which can lead to local problems, e.g., burning and stinging or ocular surface discomfort which lead to non-compliance as well as discomfort. However, to date, drops have remained as the mainstay of ophthalmic pharmaceutical delivery.

Various drug depots have been made in attempting to administer ocular drugs. The delivery of a consistent dose of a drug over time is a difficult problem that has given rise to an entire drug release industry since the first large scale commercialization of drug release on the 1950s. Some approaches have included intravitreal implant reservoir type systems or implants that need to be removed (non-erodeable). These implants are thus made to be very small with a very high drug concentration. Even though they are small, they still need to be deployed with needles larger than 25 G (25 gauge) in size, or a surgical approach delivery system for implantation or removal as needed. For instance, POSURDEX (Allergan) is a biodegradable pellet implanted for use in diabetic macular edema (DME) or retinal vein occlusions, with a 22 G delivery system used for delivery into the vitreous cavity. And for instance, a MEDIDURE implant is about 3 mm in diameter, cylindrical in shape, and non-erodeable. It is placed with a 25 G injector delivery system and has a nominal delivery life of 18 or 36 months.

Many other approaches to ocular eye delivery are known, for instance, as reviewed in the background section of US2008/0038317 (hereby incorporated herein by reference for all purposes with the instant specification controlling in case of conflict), which teaches a punctum plug made with an interior reservoir and certain biodegradable polymers that further has an impermeable member or other particular release controllers to control rate of release of a drug in the plug. And, for instance, U.S. Pat. No. 6,196,993 (hereby incorporated herein by reference for all purposes with the instant specification controlling in case of conflict) teaches a punctum plug with an interior drug-loaded reservoir that has a pore that can have a size and shape tailored to release the drug in the reservoir at a useful rate.

Despite these advances, the retention of plugs is an ongoing problem, with an unduly high percentage of them falling out before their intended life cycle is complete. A robust delivery system is needed. Indeed, conventional systems can be used only for a few types of drugs and a limited number of diseases due to delivery, dosage, and size limitations.

Certain embodiments solve this problem with a hydrogel plug that swells and locks-in place for retention, is made from a degradable hydrogel that would not require removal, and does not rely on a reservoir-system for release. The plug is particularly well suited to drug delivery to the ocular surface or anterior chamber of the eye. Disclosed herein are synthetic hydrogel punctal plugs that are high-swelling to be firmly positioned and release drugs at a predetermined rate that can be adjusted to the drug and disease condition. These hydrogels are soft and resilient for comfort and biodegrade at a predictable rate so that the plugs expire after the treatment time is over or are easily flushed out for replacement. These systems provide for a high rate of patient compliance while avoiding the need to create punctures in the eye to place drug release systems. Embodiments herein provide for a consistent matrix formulation that can be adapted to use with drugs of very different chemical properties for delivery as needed to meet a wide range of delivery dosages and times. The use of consistent tools for a wide variety of conditions is a very significant advance because it provides for a single platform that can be used repeatedly without custom-making the entire system. This approach enhances safety because clinical experience can be generated with one system and provides efficiency by eliminating a step for creation of future therapies.

BRIEF DESCRIPTION OF THE DRAWINGS

FIG. 2A depicts a punctal plug in the grasp of an applicator;

FIG. 2B depicts the applicator of FIG. 2A in use for placement of the plug;

FIG. 2C depicts the plug in place entirely within a canaliculus;

FIG. 2D depicts the plug swelling in place;

FIG. 2E depicts an alternative placement of the plug, with a proximal portion extending out of the canaliculus and the distal portion disposed within the same;

FIG. 2F depicts a swelling of the plug of the embodiment of FIG. 2E;

DETAILED DESCRIPTION

Figure 1:
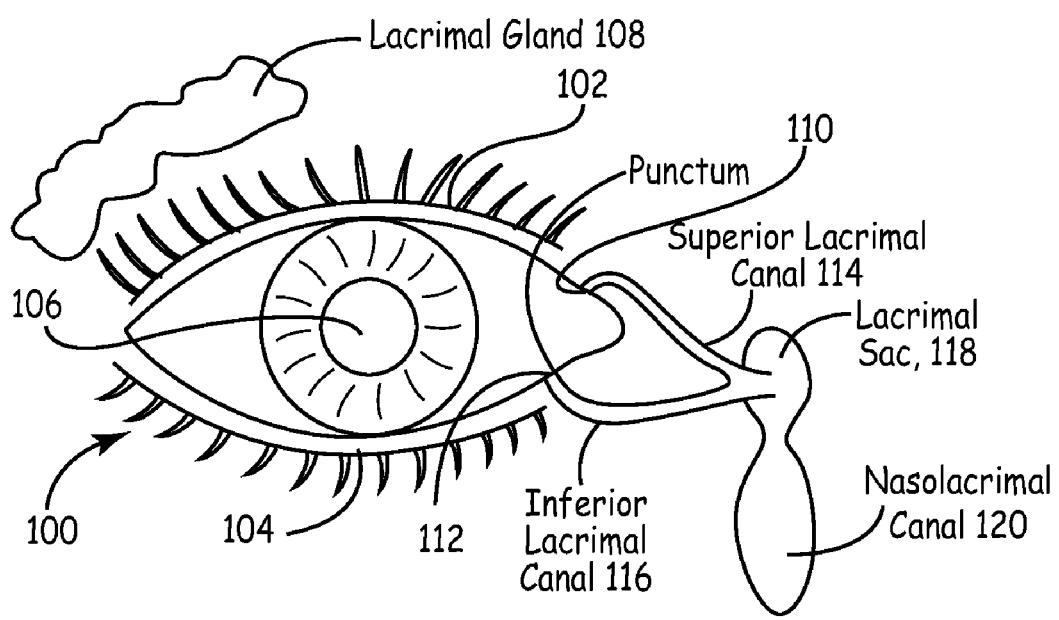
FIG. 1 is an illustration of an eye and the lacrimal system.

One embodiment is punctal plug formed of a covalently crosslinked hydrophilic polymer that absorbs water to form a hydrolytically biodegradable hydrogel that contacts and absorbs water to swell in situ to expand a canaliculus for firm and stable placement and to conformably fit the canaliculus, with the hydrogel comprising a drug for controlled release to an eye and having a high water content.

Controlled release is a complex subject area. Many drugs need to be present at a concentration that at least meets a threshold value. At the same time, a concentration that is too high may have unwanted side effects. In general, a zero-order release profile is useful. Zero-order release refers to a system wherein release is constant over time, at a rate which is independent of changes to the concentration of the reactant(s). Diffusion processes tend to be a function of the concentration of the drug, however, so that the amount of drug released per unit of time tends to drop as the concentration of the drug declines. In the case of degradable materials, the situation can be more complex if degradation affects the drug release rate. Various approaches have been developed. One approach is to trap a matrix in a device that allows fluid access only to a portion of a reservoir, with a diffusion-limiting material controlling release. Or another approach is a material that allows a surface of constant area to be eroded. Or reservoir-based approaches have been used.

Disclosed and exemplified herein, however, are hydrogel materials with agent release rates that are substantially zero-order over a predetermined time, wherein the materials have an the agent dispersed throughout the material, either with or without encapsulation. These agents may be free of non-hydrogel materials, e.g., no reservoir area, no diffusion membrane barriers, and no sleeves that control release rates. The hydrogel materials are hydrophilic and allow aqueous solutions (physiological fluids) to penetrate through the material. Moreover, the hydrogel systems may be degradable, and hydrolytically degradable. As is evident, the design factors to obtain a zero-order release hydrogel system are in competition with each other. Prior to performing experimentation as described herein, it was not known if such systems could be developed to deliver effective amounts of drugs to an eye.

In the case of punctal plugs, it is hypothesized, without being bound to a particular theory, that physiological fluids build up on top of a canalicular plug and provide a fluid column that tends to allow agent release to be limited by the cross-sectional area of the proximal portion of the plug. The walls of the canaliculus seem to elute drug at a rate that is much slower relative to the depletion of the therapeutic agent through the fluid column. Alternatively, or additionally, the canaliculus walls may become saturated with the drug so that release through the walls is slowed, and egress of the drug shifts to the ends of a plug. Therefore many of the barrier or reservoir or other relatively more complex systems that are conventionally proposed may provide little true benefit. In the case of plugs with a portion outside the canaliculus, it is hypothesized that the fluid column penetrates into the hydrogel to accomplish the same effect. Nonetheless, there are considerable challenges to be overcome when concentrating drugs into a small volume while releasing only a small portion per unit of time.

The hydrogel plug imbibes water and thereby generates force to stay in the punctum or lacrimal canal; in some embodiments, the hydrogel swells 500% or more in water when it is not constrained. The hydrogel is covalently crosslinked so that it is resilient, draws water into itself and holds it in the hydrogel to generate swelling forces, and is not re-formed into a different shape when a patient rubs their eye or the hydrogel is otherwise strained and deformed. The drug is incorporated into the hydrogel so as to provide a desired release profile, with microencapsulation, micellization, or dispersion being embodiments for drug release. Conjugation of drug to the hydrogel molecular network or to a large molecule trapped within the hydrogel matrix are also motifs that can be used to modulate drug release.

Punctal plugs fall into one of two groups: punctal plugs, which are placed at the tops of the puncta (referred to herein as punctum plugs), or intracanalicular plugs, which are inserted into the canalicula. Both permanent (stable until retrieved) and temporary plugs (biodegradable) are available. Temporary plugs are usually made of collagen and are conventionally designed to last long enough to determine whether a patient can benefit from plugging. Extended duration temporary plugs are typically made of synthetics such as poly(caprolactone-co-lactide) and poly(glycolide-co-trimethylenecarbonate). Permanent punctum plugs and intracanalicular plugs are generally made of silicone. One permanent plug is made of a hydrophobic acrylic polymer that changes shape as it is warmed to body temperature and changes from rigid to pliable. Another permanent plug is made of a non-degradable dried hydrogel that swells when exposed to tear fluid.

FIG. 1 depicts the punctum and lacrimal canals. The eye 100 has upper eyelid 102, lower eyelid 104, pupil 106, lacrimal gland 108, superior punctum 110, inferior punctum 112, superior lacrimal canal 114, inferior lacrimal canal 116, lacrimal sac 118, and nasolacrimal canal 120. The lacrimal canaliculi, also known as the lacrimal canals 112, 114 or lacrimal ducts, are the small channels in each eyelid 102, 104 that commence at minute orifices, termed puncta lacrimalia, or punctums, 110, 112 on the summits of the papillae lacrimales, seen on the margins of the lids at the lateral extremity of the lacus lacrimalis. The superior lacrimal canal 114, the smaller and shorter of the two, at first ascends, and then bends at an acute angle, and passes medialward and downward to the lacrimal sac 118. The inferior lacrimal canal 116 at first descends, and then runs approximately horizontally to lacrimal sac 118. At the angles they are dilated into ampullae. Microscopically, they are lined by nonkeratinizing stratified squamous epithelium surrounded by fibrous tissue having a further outer layer of striped muscle, continuous with the lacrimal part of the Orbicularis oculi. At the base of each lacrimal papilla the muscle fibers are arranged circularly and form a kind of sphincter.

FIG. 2A depicts forceps 200 gripping dehydrated plug 202. FIG. 2B shows use of forceps 200 to place plug 202 into inferior punctum 112 and/or inferior lacrimal canal 116. The plug is initially not swollen, as at FIG. 2C, which depicts placement of all of the plug into a lacrimal canal. The plug imbibes physiological fluid from its surroundings and swells as at FIG. 2D. Alternatively, the plug may be placed with at least a portion passing through a punctum, as at FIG. 2E, with subsequent swelling leaving a head portion. The hydrogel has internal covalent crosslinks between its polymeric members so that even when it swells in all directions, the constraints on its volume caused by the lumen of the canal prevent it from unduly lengthening; the swelling firmly positions the plug in place but the swelling does not force the plug out of its location.

U.S. Pat. No. 3,949,750, hereby incorporated by reference herein for all purposes, describes a conventional punctum plug. A rod-like plug is formed with an oversized tip or barb portion that dilates and blockingly projects into the canaliculus, a smaller neck or waist portion upon which the punctum sphincter ring tightens, and a relatively larger, smooth head portion which rests upon the top of the punctal opening and prevents the plug from passing down into the canaliculus. The head portion sits upon the body portion, which optionally has the waist portion. A typical method for inserting the plug into the punctal opening utilizes a dilator tool for enlarging the punctum and associated canaliculus and an inserter tool for facilitating the grasping, manipulation and insertion of the plug.

Figure 3A:
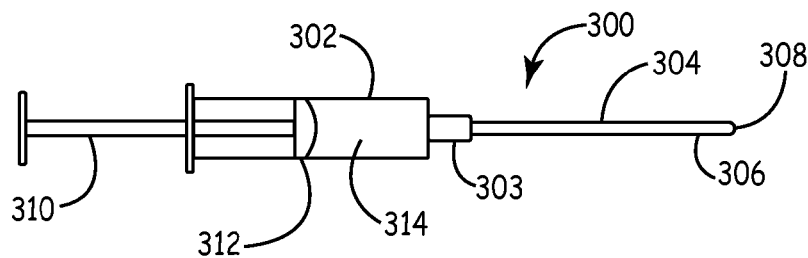
FIG. 3A depicts a syringe-type applicator for placing precursors into a site for in situ punctal plug formation.
Figure 3B:
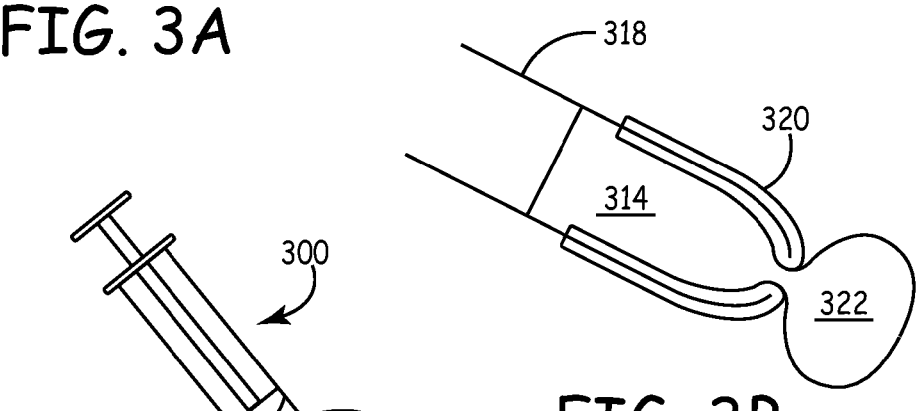
FIG. 3B depicts the applicator introducing the precursors to form a punctal plug in situ.

FIG. 3A depicts syringe system 300 with barrel 302, needle hilt 303, needle 304 with rounded tip 306 having outlet 308 and plunger 310 with pusher 312. A solution of hydrogel precursors 314 may be placed in barrel 302 and dispensed through needle 304 and out outlet 308. One embodiment of syringe system 300 is depicted in FIG. 3B, which shows alternative needle 318 with a hydrophobic coating 320 that produces a high contact angle between the needle and precursor solution 314 to assist forming drop 322 and/or assist in leaving the solution 314 after it is placed in the patient by virtue of the resistance of the needle to spreading of solution 314.

Figure 4A:
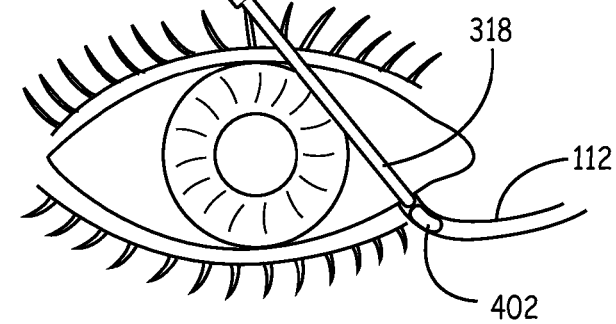
FIG. 4A depicts an applicator after placement of precursors that form a plug in situ.
Figure 4B:
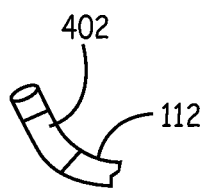
FIG. 4B depicts the formation of the plug of FIG. 3B.
Figure 4C:
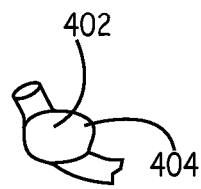
FIG. 4C depicts swelling of the plug of FIG. 4B.

FIG. 4A depicts syringe system 300 being used to introduce hydrogel precursors 314 into canal 112, with the precursors being left in canal 112. The precursors form covalent bonds with each other to create a crosslinked hydrogel plug 402. The hydrogel 402 swells as fluids are imbibed from its surroundings, as at FIG. 4C showing plug 402 in swollen state 404, pressing against the lumen of canal 112 and expanding the canal. The introduction of hydrogel precursors in a fluid state with subsequent formation of the hydrogel is referred to as in situ formation of the hydrogel because the hydrogel is created at the site of its intended use.

Hydrogels are materials that do not dissolve in water and retain a significant fraction (more than 20%) of water within their structure (Szycher's dictionary of Biomaterials and Medical Devices, Technomic Pub. Co., Lancaster, 1992). In fact, water contents in excess of 90% are often known. Hydrogels are often formed by crosslinking water soluble molecules to form networks of essentially infinite molecular weight. Hydrogels with high water contents are typically soft, pliable materials. When made with pliable materials, high-content hydrogels are comfortably worn in the eye and avoid the foreign-object sensation that can accompany more rigid materials, for instance plugs made of polylactic acid (PLA) and/or polyglycolic acid (PGA). A hydrogel that has been dried is referred to herein as a dehydrated hydrogel if it will return to a hydrogel state upon exposure to water (also referred to as a xerogel); this hydrogel that would expand in volume if it were exposed to an excess of water and not constrained. The term desiccated refers to a hydrogel essentially having no fluids, bearing in mind that some trace amounts of water may nonetheless be present.

A hydrogel network may be formed in a non-water solvent with a therapeutic agent optionally being present at the time of hydrogel network formation or loaded afterwards. The non-water solvent can then be replaced with water by a suitable means to form the hydrogel. The term therapeutic agent includes diagnostic agents, imaging agents, and drugs. The term drug refers to an agent intended to provoke a biological response so as to treat a patient. The hydrogels may be biodegradable or non-biodegradable.

The therapeutic agent may be dispersed (meaning spread substantially throughout a structure, either as a solution, suspension, or a colloid) within the hydrogel. The agent may be dispersed in the same phase as the fluid hydrating the hydrogel or it may be contained in a phase discontinuous from the fluid in the hydrogel. A phase discontinuous from the hydrogel may be a micelle, droplet, or a particle. Accordingly, a drug entrapped within microspheres dispersed within a hydrogel is a drug dispersed within the hydrogel. By way of contrast, a drug localized to a reservoir is not dispersed. A micelle, droplet, or a particle may include, for instance, a mixture of the drug with another material, e.g., a polymer. One embodiment of a particle is a capsule with the drug inside the capsule. Another embodiment of a particle is a solid formed by a polymer that associates with the drug. A particle may release a drug as it degrades, by diffusion, or a combination thereof. These features may be combined to provide a desired agent-release profile. A hydrogel with an agent dispersed through the hydrogel refers to a continuous hydrogel matrix with a substantially even distribution of agent throughout the structure.

Placement

Punctal plugs may be placed in, or partially within a lacrimal canal. Forceps or other applicators may be used to grasp the plugs and insert them. Or precursors may be placed into a lacrimal canal and allowed to crosslink to form a plug. Another option is placement of microspheres and/or a hydrogel (dehydrated, desiccated, partially hydrated, or hydrated) within the conjunctival cul-de-sac, between the lower lid and the eye. Examples of other devices that use this placement sit are disclosed in U.S. Pat. No. 3,618,604, U.S. Pat. No. 3,626,940, U.S. Pat. No. 3,845,770, U.S. Pat. No. 3,962,414, U.S. Pat. No. 3,993,071, and U.S. Pat. No. 4,014,335, each of which are hereby incorporated herein by reference for all purposes, with the specification herein controlling in case of conflict.

Another option is to place microspheres and/or a hydrogel subconjunctivally between the conjunctiva and the sclera. For instance, a syringe may be used to pierce the conjunctiva without piercing the sclera, and the hydrogel and/or microspheres and/or hydrogel precursors injected to form a depot. One or more of these components may be formed as a degradable material. Another option is to form such material(s) topically on a surface of the eye (e.g., cornea or a site that is topical but avoids the cornea). Therapeutic agents in these material(s) may then be released over time to accomplish a therapy. As is evident, the various embodiments set forth herein may be thusly administered.

A micropdepot may be formed with such materials and optionally at a subconjunctival site. For instance, a volume of 5-400 µl may be formed; artisans will immediately appreciate that all the ranges and values within the explicitly stated ranges are contemplated, e.g., about 5 to about 30 µl or from about 20 to about 100 µl.

Hydrogel Precursors

Hydrogels may be made from precursors. The precursors are not hydrogels but are covalently crosslinked with each other to form a hydrogel and are thereby part of the hydrogel. Crosslinks can be formed by covalent or ionic bonds, by hydrophobic association of precursor molecule segments, or by crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form polymers made of repeating units. Precursors may be polymers.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer (or macromer) is a polymer or oligomer that has at least one reactive group, often at the end, which enables it to act as a monomer; each macromonomer molecule is attached to the polymer by reaction the reactive group. Thus macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically these reactions can be achieved through reacting molecules incorporating alcohol, amine or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference herein in its entirety to the extent it does not contradict what is explicitly disclosed herein.

Some precursors react by a chain growth mechanism. Chain growth polymers are defined as polymers formed by the reaction of monomers or macromonomers with a reactive center. A reactive center is a particular location within a chemical compound that is the initiator of a reaction in which the chemical is involved. In chain-growth polymer chemistry, this is also the point of propagation for a growing chain. The reactive center is commonly radical, anionic, or cationic in nature, but can also take other forms. Chain growth systems include free radical polymerization, which involves a process of initiation, propagation and termination. Initiation is the creation of free radicals necessary for propagation, as created from radical initiators, e.g., organic peroxide molecules. Termination occurs when a radical reacts in a way that prevents further propagation. The most common method of termination is by coupling where two radical species react with each other forming a single molecule.

Some precursors react by a step growth mechanism, and are polymers formed by the stepwise reaction between functional groups of monomers. Most step growth polymers are also classified as condensation polymers, but not all step growth polymers release condensates.

Monomers may be polymers or small molecules. A polymer is a high molecular weight molecule formed by combining many smaller molecules (monomers) in a regular pattern. Oligomers are polymers having less than about 20 monomeric repeat units. A small molecule generally refers to a molecule that is less than about 2000 Daltons.

The precursors must thus be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, or U.S. Pat. Nos. 4,741,872 and 5,160,745 to DeLuca et al., each of which is hereby incorporated by reference herein in its entirety to the extent it does not contradict what is explicitly disclosed herein.

To form covalently crosslinked hydrogels, the precursors must be crosslinked together. In general, polymeric precursors will form polymers that will be joined to other polymeric precursors at two or more points, with each point being a linkage to the same or different polymers. Precursors with at least two reactive groups can serve as crosslinkers since each reactive group can participate in the formation of a different growing polymer chain. In the case of functional groups without a reactive center, among others, crosslinking requires three or more such functional groups on a precursor. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction. A covalent crosslink, however, will typically offer stability and predictability in reactant product architecture.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and hydrophilic portions, e.g., a core. In the case of a branched polymer, a core refers to a contiguous portion of a molecule joined to anus that extend from the core, with the arms having a functional group, which is often at the terminus of the branch. The hydrophilic precursor or precursor portion preferably has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly(vinyl pyrrolidinone) (PVP), poly(amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly(oxyalkylenes) or poly(ethylene glycol) or polyethylene glycol are generally hydrophilic.

A precursor may also be a macromolecule (or macromer), which is a molecule having a molecular weight in the range of a few thousand to many millions. In some embodiments, however, at least one of the precursors is a small molecule of about 1000 Da or less. The macromolecule, when reacted in combination with a small molecule of about 1000 Da or less, is preferably at least five to fifty times greater in molecular weight than the small molecule and is preferably less than about 60,000 Da; artisans will immediately appreciate that all the ranges and values within the explicitly stated ranges are contemplated. A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000.

Certain macromeric precursors are the crosslinkable, biodegradable, water-soluble macromers described in U.S. Pat. No. 5,410,016 to Hubbell et al, which is hereby incorporated herein by reference in its entirety to the extent it does not contradict what is explicitly disclosed. These macromers are characterized by having at least two polymerizable groups, separated by at least one degradable region.

Synthetic precursors may be used. Synthetic refers to a molecule not found in nature or not normally found in a human. Some synthetic polymers are free of amino acids or free of amino acid sequences that occur in nature. Some synthetic molecules are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Precursors may be made with a hydrophobic portion provided that the resultant hydrogel retains the requisite amount of water, e.g., at least about 20%. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TECTRONIC. A hydrophobic portion is one that is sufficiently hydrophobic to cause the macromer or copolymer to aggregate to form micelles in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

Thus hydrogels can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or non-polymers and natural or synthetic.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment, and can change substantially according to the solvent or solutes around it, e.g., changes in temperature, pH, or ion content.

Precursors may be dendrimers, e.g., as in Patent Application Pub. Nos. US20040086479, US20040131582, WO07005249, WO07001926, WO06031358, or the U.S. counterparts thereof; dendrimers may also be useful as multifunctional precursors, e.g., as in U.S. Pat. Pub. Nos. US20040131582, US20040086479 and PCT Applications No. WO06031388 and WO06031388; each of which US and PCT applications are hereby incorporated by reference herein in its entirety to the extent they do not contradict what is explicitly disclosed herein. Dendrimers are highly ordered possess high surface area to volume ratios, and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and can not be made by cleaving a naturally occurring protein and can not be made by adding synthetic materials to a protein. Precursors may be non-collagen, non-fibrin, non-fibrinogen), and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight. Thus a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some hydrogels are made with a polyethylene glycol-containing precursor. Polyethylene glycol (PEG, also referred to as polyethylene oxide when occurring in a high molecular weight) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group.

Initiating Systems

Some precursors react using initiators. An initiator group is a chemical group capable of initiating chain growth (e.g., a free radical) polymerization reaction. For instance, it may be present as a separate component, or as a pendent group on a precursor. Free radical initiator groups include thermal initiators, photoactivatable initiators, and oxidation-reduction (redox) systems. Long wave UV and visible light photoactivatable initiators include, for example, ethyl eosin groups, 2,2-dimethoxy-2-phenyl acetophenone groups, other acetophenone derivatives, thioxanthone groups, benzophenone groups, and camphorquinone groups. Examples of thermally reactive initiators include 4,4' azobis (4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogels with the aforementioned monomers.

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

Functional Groups

The precursors have functional groups that react with each other to form the material, either outside a patient, or in situ. The functional groups generally have polymerizable groups for polymerization or react with each other in electrophile-nucleophile reactions or are configured to participate in other polymerization reactions. Various aspects of polymerization reactions are discussed in the precursors section herein.

Thus in some embodiments, precursors have a polymerizable group that is activated by photoinitiation or redox systems as used in the polymerization arts, e.g., or electrophilic functional groups that are carbodiimidazole, sulfonyl chloride, chlorocarbonates, n-hydroxysuccinimidyl ester, succinimidyl ester or sulfasuccinimidyl esters, or as in U.S. Pat. No. 5,410,016, or U.S. Pat. No. 6,149,931, each of which are hereby incorporated by reference herein in its entirety to the extent they do not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michael addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide (NHS) groups are useful groups for crosslinking of proteins or amine-containing polymers, e.g., amino terminated polyethylene glycol. An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7).

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di- or multifunctional poly(ethylene glycol) can be used.

One embodiment has reactive precursor species with 3 to 16 nucleophilic functional groups each and reactive precursor species with 2 to 12 electrophilic functional groups each; artisans will immediately appreciate that all the ranges and values within the explicitly stated ranges are contemplated.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a of Michael-type reaction. The strong electrophile may be of a type that does not participate in a Michaels-type reaction or of a type that participates in a Michaels-type reaction.

A Michael-type reaction refers to the 1,4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Michael-type reactions are discussed in detail in U.S. Pat. No. 6,958,212, which is hereby incorporated by reference herein in its entirety for all purposes to the extent it does not contradict what is explicitly disclosed herein.

Examples of strong electrophiles that do not participate in a Michaels-type reaction are: succinimides, succinimidyl esters, or NHS-esters. Examples of Michael-type electrophiles are acrylates, methacrylates, methylmethacrylates, and other unsaturated polymerizable groups.

Hydrogels and Hydrogel Formation

In general, the precursors may be combined to make a covalently-crosslinked hydrogel. The hydrogel may comprise a therapeutic agent, or agents, released over a suitable period of time. Hydrogels may be made beforehand or in situ.

When made in situ, the crosslinking reactions generally occur in aqueous solution under physiological conditions. The crosslinking reactions preferably do not release heat of polymerization or require exogenous energy sources for initiation or to trigger polymerization. Photochemical initiation, for instance, is generally to be avoided in the eye so as to avoid damage to the eye. In the case of injected materials, the viscosity may be controlled so that the material is introduced through a small diameter catheter or needle. When hydrogels are made beforehand, the polymers made be made in aqueous and/or organic solvents.

The hydrogel is generally high-swelling, as measurable by the hydrogel having a weight increasing more than about 50% upon exposure to a physiological solution in the absence of physical restraints for twenty-four hours relative to a weight of the hydrogel at the time of formation. Swelling may be measured or expressed by weight or volume. Some embodiments swell by weight or by volume more than about 1000%, more than about 500%, or more than about 100%; artisans will immediately appreciate that all the ranges and values within the explicitly stated ranges are contemplated, e.g., more than about 200% or from about 300% to about 1000%. Accordingly, some embodiments include hydrogels that swell by weight or by volume between about 100% to about 2000%, between about 200% to about 1500%, or between about 300% and about 1100%; artisans will immediately appreciate that all the ranges and values within the explicitly stated ranges are contemplated.

One approach for high-swelling is to control the number of crosslinks. Another embodiment is mixing-into the hydrogel precursors a high molecular weight water soluble synthetic or natural polymer that does not covalently cross-link with the precursors to achieve a crosslinked hydrogel with these other materials dispersed therein. Examples of such materials are carboxy methyl cellulose, hyaluronic acid, and high molecular weight PEG, e.g., the high molecular weight being more than about 100,000 MW, e.g., from about 100,000 to about 10,000,000; artisans will immediately appreciate that all the ranges and values within the explicitly stated ranges are contemplated, e.g., from about 250,000 to about 1,000,000). These added materials can greatly increase swelling of the cross linked hydrogel as the highly water soluble large polymers remain entangled within the network causing an increased osmotic pressure within the hydrogel structure, thus causing the hydrogel to swell more.

In pre-formed dehydrated hydrogels, a degree of molecular orientation can be imparted by stretching the material then allowing it to solidify, locking in the molecular orientation. This can be accomplished by drawing the material while heated to a temperature above the melting point of the crystallizable regions of the material, then allowing the crystallizable regions to crystallize. Alternatively, the glass transition temperature of the dried hydrogel can be used to lock in the molecular orientation. Still another alternative is to draw the gel prior to complete dehydration (or drying) and then drying the material while under tension. The molecular orientation provides a mechanism for anisotropic swelling upon introduction into a hydrating medium. A rod can be formed, however, that will swell only in the radial dimension, neither increasing or decreasing in length. Radial swelling may be desirable in a punctum plug, but growth or shrinkage in length is sometimes a problem with retention of the device where placed by the surgeon. The change in length causes the punctal plug to be forced out or to be difficult to retrieve. Accordingly, a radial-swelling punctal plug may be made that is free of longitudinal shrinking and/or swelling. The term istotropic means to swell consistently in all directions when not constrained. The term anisotropic means to swell preferentially in one direction as opposed to another, as in a cylinder that swells predominantly in the radial direction to conform to the canaliculus and/or punctum, but does not appreciably expand or contract in the longitudinal dimension, thus maintaining its position as placed by the surgeon. Minimal length increases in combination with significant radial increases provides improved retention of the plug during the course of the therapy.

Another embodiment to increase swelling is to choose precursors that have a low degree of solvation at the time of crosslinking but subsequently become more solvated and having a radius of solvation that effectively increases; in other words, the precursor is spread-out in solution after crosslinking but relatively contracted when crosslinked. Changes to pH, temperature, solids concentration, and solvent environment can cause such changes.

Unless otherwise indicated, swelling of a hydrogel relates to its change in volume (or weight) between the time of its formation when crosslinking is effectively complete and the time after being placed in vitro aqueous solution in an unconstrained state for twenty-four hours, at which point it may be reasonably assumed to have achieved its equilibrium swelling state. For most embodiments, crosslinking is effectively complete within no more than about fifteen minutes such that the initial weight can generally be noted at about 15 minutes after formation as Weight at initial formation. Accordingly, this formula is used: % swelling=[(Weight at 24 hours−Weight at initial formation)/Weight at initial formation]*100. The weight of the hydrogel includes the weight of the solution in the hydrogel. A hydrogel formed in a location wherein it is constrained may nonetheless be considered a high-swelling hydrogel because it is the expansion in the unconstrained state that defines the amount of swelling. For instance, a swellable hydrogel created in a body may be constrained from swelling by its surroundings but nonetheless may be a highly swellable hydrogel as evidenced by measurements of its swelling when unconstrained and/or the forces against a constraint.

Reaction kinetics are generally controlled in light of the particular functional groups unless an external initiator or chain transfer agent is required, in which case triggering the initiator or manipulating the transfer agent can be a controlling step. In some embodiments, the molecular weights of the precursors are used to affect reaction times. Precursors with lower molecular weights tend to speed the reaction due to their higher concentration of reactive groups, so that some embodiments have at least one precursor with a molecular weight of less than about 1000 or about 2000 Daltons; artisans will immediately appreciate that all the ranges and values within the explicitly stated ranges are contemplated, e.g., from 100 to about 900 Daltons or from 500 to about 1800 Daltons. Preferably the crosslinking reaction leading to gelation occurs within less than about 2 to about 10 or to about 30 minutes; artisans will immediately appreciate that all the ranges and values within the explicitly stated ranges are contemplated, e.g., at least 120 seconds, or between 180 to 600 seconds. Gelation time is measured by applying the precursors to a flat surface and determining the time at which there is substantially no flow down the surface when it is titled at an angle of about 60 degrees (i.e., a steep angle, close to perpendicular). In the case of hydrogel formation in situ, a gelation time of less than about 2 minutes, or about 1 minute or about 30 seconds is useful; artisans will immediately appreciate that all the ranges and values within the explicitly stated ranges are contemplated, e.g., from about 5 to about 90 seconds or from about 10 to about 40 seconds.

The crosslinking density of the resultant biocompatible crosslinked polymer is controlled by the overall molecular weight of the crosslinker and functional polymer and the number of functional groups available per molecule. A lower molecular weight between crosslinks such as 500 will give much higher crosslinking density as compared to a higher molecular weight such as 10,000. The crosslinking density also may be controlled by the overall percent solids of the crosslinker and functional polymer solutions. Increasing the percent solids increases the probability that an electrophilic functional group will combine with a nucleophilic functional group prior to inactivation by hydrolysis. Yet another method to control crosslink density is by adjusting the stoichiometry of nucleophilic functional groups to electrophilic functional groups. A one to one ratio leads to the highest crosslink density. Precursors with longer distances between crosslinks are generally softer, more compliant, and more elastic. Thus an increased length of a water-soluble segment, such as a polyethylene glycol, tends to enhance elasticity to produce desirable physical properties. Thus certain embodiments are directed to precursors with water soluble segments having molecular weights in the range of 3,000 to 100,000 or, e.g., 10,000 to 35,000.

The solids content of the hydrogel can affect its mechanical properties and biocompatibility and reflects a balance between competing requirements. A relatively low solids content is useful, e.g., between about 2.5% to about 25%, including all ranges and values there between, e.g., about 2.5% to about 10%, about 5% to about 15%, or less than about 15%.

Figure 12:
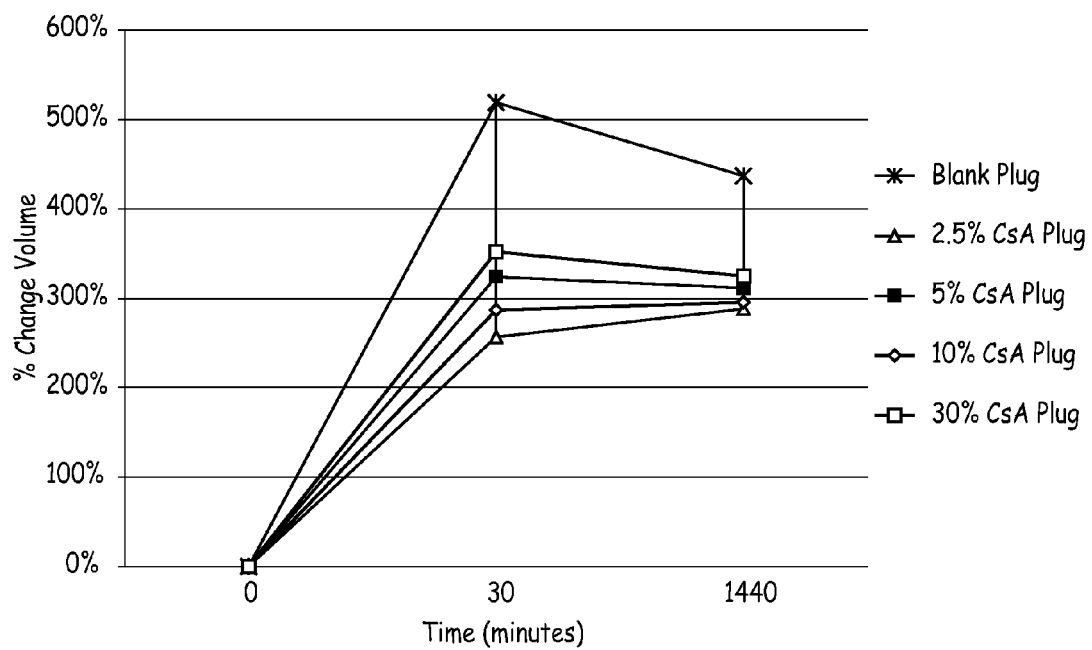
FIG. 12 is a graph demonstrating the reduction in swelling of hydrogel plugs by incorporation of hydrophobic domains.

It has surprisingly been found that loading hydrogels with hydrophobic domains in sufficient concentration will be effective to reduce the swelling of hydrogels. FIG. 12 documents this effect. Increased loading of cyclosporine A in the hydrogels decreased the overall swelling.

Processes for Making Hydrogels

Processes for making hydrogels that incorporate a drug include, for example, making a hydrogel in an organic solvent or in aqueous solution with the drug present at the time of formation of the hydrogel or added the hydrogel after its formation. The hydrogel may be made beforehand (a preformed device) and at least partially dehydrated or desiccated, or made in situ in a solution at the site of formation.

One embodiment for making a hydrogel is to make a preformed device in an organic-solvent in the presence of a therapeutic agent. A first hydrogel precursor with a first type functional groups is dissolved with a second hydrogel precursor with a second type of functional groups in an organic solvent in the presence of a therapeutic agent that is miscible in the organic solvent. The solution is introduced into a mold and left until the precursors crosslink with each other by covalent bond formation between the first functional groups and the second functional groups. The hydrogel is fully or partially dried to form a dehydrated or desiccated hydrogel (xerogel). The hydrogel is then removed and optionally cut or otherwise trimmed to another shape or size. This embodiment may be used, for example, for loading the hydrogel with non-water soluble agents or encapsulated agents tolerant to the organic phase.

An embodiment for making a preformed device in an organic-solvent in the presence of a therapeutic agent is to dissolve a branched polyethylene glycol with electrophilic functional groups at each arm terminus with a nucleophilic precursor in methanol containing a therapeutic agent. The precursors are formed into a hydrogel, dried, and shaped as desired.

Another embodiment for making a hydrogel is to make a preformed device in an organic solvent and, after the hydrogel is formed, load the hydrogel with a therapeutic agent. A first hydrogel precursor with a first type functional groups is dissolved with a second hydrogel precursor with a second type of functional groups in an organic solvent. The solution is introduced into a mold and left until the precursors crosslink with each other by covalent bond formation between the first functional groups and the second functional groups. The hydrogel is fully or partially dried to form a dehydrated or desiccated hydrogel. An organic solvent (the same or different from the one used during crosslinking) that swells the cross-linked hydrogels is added. This solvent contains dissolved agents at high concentrations. The hydrogels are allowed to swell with the organic drug solution, causing some drug to permeate into the hydrogel matrix. Gels are removed, and either dried again as above, or placed into a non-solvent, e.g., hexane. The non-solvent causes the organic solvent to leave the gel and the agent to precipitate-out in the gel matrix, leaving an agent-loaded plug. This embodiment may be used, for example, for loading of agents incompatible with the particular crosslinking functional groups, e.g., agents with primary amines when precursor amine functional groups are intended to be reacted during crosslinking. This separation of drug loading and crosslinking steps removes problems with chemical incompatibility between the therapeutic agent and the crosslinking reaction.

An embodiment for making a hydrogel is thus dissolving a branched polyethylene glycol with electrophilic functional groups at each arm terminus with a nucleophilic precursor. The precursors are mixed or otherwise activated to form the crosslinked hydrogel in a mold and then dried of solvent. The pre-formed devices are added to a solvent that swells the cross-linked hydrogel. The solvent contains dissolved drugs at high concentrations. Plugs are allowed to swell with the solvent-agent solution, causing some drug to permeate into the hydrogel matrix. Gels are removed, and either dried again as above, or placed into a precipitating agent such as hexane. If the precipitating agent is compatible with the solvent, bit incompatible with the gel network and the therapeutic agent, it causes the solvent to migrate from the gel leaving the drug to precipitate out in the gel matrix, forming a drug loaded plug.

Another embodiment for making a hydrogel is to make a preformed device in an aqueous solvent in the presence of a therapeutic agent. A first hydrogel precursor with a first type of functional groups is dissolved with a second hydrogel precursor with a second type of functional groups in an aqueous solvent in the presence of a therapeutic agent in the solvent. The solution is introduced into a mold and left until the precursors crosslink with each other by covalent bond formation between the first functional groups and the second functional groups. The hydrogel is fully or partially dried to form a dehydrated or desiccated hydrogel. The hydrogel is then removed and optionally cut or otherwise trimmed to another shape or size. This embodiment may be used, for example, for loading the hydrogel with non-water soluble agents or encapsulated agents tolerant to the aqueous phase. The agent may be dispersed in the aqueous solvent, e.g., in solution or suspension. A suspension may be, for instance, a particle comprising the agent or a suspension of encapsulated agent. This embodiment is useful for, for example, loading of hydrogels with agents already encapsulated in other polymer systems. The aqueous based manufacture may also be used to avoid extraction of the encapsulated agent, which could occur with some organic solvents.

An embodiment for making a hydrogel is thus dissolving a branched polyethylene glycol with electrophilicly activated termini with a nucleophilic precursor in water containing an agent, e.g., a suspension of drug. The hydrogel is formed in a mold and dried. The dried plugs are removed from the mold, and optionally further processed, e.g., for size or shape.

An embodiment for making a hydrogel in situ in the presence of a therapeutic agent is to combine precursors in an aqueous solution that can be administered with an applicator to the punctum and/or canaliculus and thereafter form the hydrogel. The precursors may be mixed with an activating agent before, during, or after administration. The hydrogel may be placed with a therapeutic agent dispersed therein, e.g., as a solution, suspension, particles, micelles, or encapsulated. Crosslinking, in one embodiment, entraps the agent. In another embodiment, the crosslinking causes the agent to precipitate or move from solution to suspension.

Thus one embodiment relates to combining a first hydrogel precursor with a first type of functional groups with a second hydrogel precursor having a second type of functional groups in an aqueous solvent in the presence of a therapeutic agent in the solvent. In one embodiment, the precursors are dissolved separately and combined in the presence of an activating agent that provides for effective crosslinking. Alternatively, the mere mixing of the precursors triggers crosslinking. Accordingly, one embodiment is providing branched polymer having a plurality of succinimidyl termini dissolved in a low pH (4.0) diluent solution) containing a low molecular weight precursor comprising nucleophiles. This solution is activated by combination with a higher pH solution (8.8), initiating the crosslinking mechanism. The agent is pre-loaded as a suspension in the diluent solution. The solution is applied to a canaliculus, or drawn into a small (e.g., 1 cc) syringe with a suitable cannula (e.g., 27 G) and injected into the canaliculus. The gel forms in situ.

The crosslinking chemistry may also be carried out in a volatile organic solvent. Thus one embodiment relates to combining a first hydrogel precursor with a first type of functional groups with a second hydrogel precursor having a second type of functional groups in a volatile organic solvent, optionally in the presence of a therapeutic agent in the solvent. Or a precursor may be combined with a volatile organic solvent optionally with an agent present to otherwise make the hydrogel. The precursors are reacted to form a device, e.g., a rod-shaped punctal plug. A volatile organic solvent refers to a solvent that has a boiling point of less than about 100° C. Examples of volatile organic solvents are: methanol (65° C.), ethanol (78° C.), acetonitrile (81° C.). In some embodiments, the therapeutic agent has low water solubility. This process advantageously provides for ready entrapment of the agent in the crosslinked hydrogel.

In some embodiments, the therapeutic agent is mixed with the precursors prior to making the aqueous solution or during the aseptic manufacturing of the functional polymer. This mixture then is mixed with the precursor to produce a crosslinked material in which the biologically active substance is entrapped.

Phase Separation of Agents for Delivery

In some embodiments, the therapeutic agent or agents are present in a separate phase when precursor(s) are reacted to produce a crosslinked polymer hydrogel. This phase separation prevents participation of therapeutic agents in the chemical crosslinking reaction such as reaction between NHS ester and amine group. The separate phase also helps to modulate the release kinetics of active agent from the crosslinked material or gel, where 'separate phase' could be oil (oil-in water emulsion), biodegradable vehicle, and the like. Biodegradable vehicles in which the active agent may be present include: encapsulation vehicles, such as microparticles, microspheres, microbeads, micropellets, and the like, where the active agent is encapsulated in a bioerodable or bioresorbable polymer such as polymers and copolymers of: poly(anhydride), poly(hydroxy acid)s, poly(lactone)s, poly(trimethylene carbonate), poly(glycolic acid), poly(lactic acid), poly(glycolic acid)-co-poly(glycolic acid), poly(orthocarbonate), poly(caprolactone), caging and entrapping molecules, like cyclodextrin, molecular sieves and the like. Microspheres made from polymers and copolymers of poly(lactone)s and poly(hydroxy acid)s are useful biodegradable encapsulation vehicles.

Certain embodiments of the invention are accomplished by providing compositions and methods to control the release of relatively low molecular weight therapeutic species using hydrogels. A therapeutic agent first is dispersed or dissolved within one or more relatively hydrophobic rate modifying agents to form a mixture. The mixture may be formed into particles or microparticles, which are then entrapped within a bioabsorbable hydrogel matrix so as to release the water soluble therapeutic agents in a controlled fashion. Alternatively, the microparticles may be formed in situ during crosslinking of the hydrogel. Drugs can be encapsulated using a variety of techniques for the purpose of controlled release prior to incorporation into punctum plugs. These controlled release systems may be forms of suspensions, oil solutions, emulsions, liposomes, micelles, implants and microparticles. Polymeric controlled release systems are commonly used in the pharmaceutical industry to provide sustained release with well over a dozen marketed products based on biodegradable polymers. Synthetic forms of biodegradable polymers may include polyorthoesters, polyanhydrides, polyphosazenes, polyamino acids polyalkylcyanoacrylates, polyesters (such as polycaprolactone, polydioxanone, polytrimethylenecarbonate, etc.), and the more frequently employed polyesters (poly(lactide) (PLA) and poly(lactide-co-glycolide) (PLGA)).

With respect to microparticle fabrication techniques, hydrophilic drugs are typically incorporated in the inner aqueous phase (see multiple emulsion method) or as solids dispersed in the oil phase (see dispersion method), whereas lipophilic drugs are generally dissolved in the organic/oil phase (see cosolvent method). With respect to solvent casting, the drugs are incorporated similarly to the cosolvent method minus the continuous phase necessary for microparticle formation. With respect to melt extrusion or compression techniques, the drugs may be incorporated in their initial state in the absence of solvent. Variations of these incorporation techniques exist and may be adjusted, as multiple variables (e.g., drug loading, solubility, solvent selection and blends, polymer concentration, polymer type and blends, excipients, targeted release duration, drug stability) play a role in selecting the best choice to incorporate the drug into the polymer matrix.

In one method, hydrogel microspheres are formed from polymerizable macromers or monomers by dispersion of a polymerizable phase in a second immiscible phase, wherein the polymerizable phase contains at least one component required to initiate polymerization that leads to crosslinking and the immiscible bulk phase contains another component required to initiate crosslinking, along with a phase transfer agent. Pre-formed microparticles containing the water soluble therapeutic agent may be dispersed in the polymerizable phase, or formed in situ, to form an emulsion. Polymerization and crosslinking of the emulsion and the immiscible phase is initiated in a controlled fashion after dispersal of the polymerizable phase into appropriately sized microspheres, thus entrapping the microparticles in the hydrogel microspheres. Visualization agents may be included, for instance, in the microspheres, microparticles, and/or microdroplets.

Embodiments of the invention include compositions and methods for forming composite hydrogel-based matrices and microspheres having entrapped therapeutic compounds. In one embodiment, a bioactive agent is entrapped in microparticles having a hydrophobic nature (also termed hydrophobic microdomains), to retard leakage of the entrapped agent. In some cases, the composite materials that have two phase dispersions, where both phases are absorbable, but are not miscible. For example, the continuous phase may be a hydrophilic network (such as a hydrogel, which may or may not be crosslinked) while the dispersed phase may be hydrophobic (such as an oil, fat, fatty acid, wax, fluorocarbon, or other synthetic or natural water immiscible phase, generically referred to herein as an "oil" or "hydrophobic" phase).

The oil phase entraps the drug and provides a barrier to release by slow partitioning of the drug into the hydrogel. The hydrogel phase in turn protects the oil from digestion by enzymes, such as lipases, and from dissolution by naturally occurring lipids and surfactants. The latter are expected to have only limited penetration into the hydrogel, for example, due to hydrophobicity, molecular weight, conformation, diffusion resistance, etc. In the case of a hydrophobic drug which has limited solubility in the hydrogel matrix, the particulate form of the drug may also serve as the release rate modifying agent.

Hydrophobic microdomains, by themselves, may be degraded or quickly cleared when administered in vivo, making it difficult to achieve prolonged release directly using microdroplets or microparticles containing the entrapped agent in vivo. In accordance with the present invention, however, the hydrophobic microdomains are sequestered in a gel matrix. The gel matrix protects the hydrophobic microdomains from rapid clearance, but does not impair the ability of the microdroplets or microparticles to release their contents slowly. Visualization agents may be included, for instance, in the gel matrix or the microdomains.

In one embodiment, a microemulsion of a hydrophobic phase and an aqueous solution of a water soluble molecular compound, such as a protein, peptide or other water soluble chemical is prepared. The emulsion is of the "water-in-oil" type (with oil as the continuous phase) as opposed to an "oil-in-water" system (where water is the continuous phase). Other aspects of drug delivery are found in U.S. Pat. Nos. 6,632,457; 6,379,373; and 6,514,534, each of which are hereby incorporated by reference herein in its entirety. Moreover, drug delivery schemes as described in U.S. Ser. No. 12/012,808 filed Feb. 6, 2008 and its priority document 60/899,898 filed Feb. 6, 2007, which are each hereby incorporated by reference herein in its entirety, and accordingly may also be used with the hydrogels and punctal plugs and particles herein.

Controlled rates of therapeutic agent delivery also may be obtained with the system disclosed herein by degradable, covalent attachment of the therapeutic agents to the crosslinked hydrogel network. The nature of the covalent attachment can be controlled to enable control of the release rate from hours to weeks or longer. By using a composite made from multiple linkages with a range of hydrolysis times, a controlled release profile may be extended for longer durations.

Agents can be encapsulated using a variety of techniques for the purpose of controlled release prior to incorporation into punctal plugs. These controlled release systems may be forms of suspensions, oil solutions, emulsions, liposomes, micelles, implants and microparticles. Polymeric controlled release systems are commonly used in the pharmaceutical industry to provide sustained release with well over a dozen marketed products based on biodegradable polymers. Synthetic forms of biodegradable polymers may include polyorthoesters, polyanhydrides, polyphosazenes, polyamino acids polyalkylcyanoacrylates, polyesters (such as polycaprolactone, polydioxanone, polytrimethylenecarbonate, etc.), and the more frequently employed polyesters (poly (lactide) (PLA) and poly(lactide-co-glycolide) (PLGA)).

Polyesters such as poly(lactide) (PLA) and its glycolic acid copolymer poly(lactide-co-glycolide) (PLGA) may be used as a drug carrier due to their biocompatibility, biodegradability and mechanical strength. They degrade by hydrolysis of the ester backbone and their degradation products (i.e. lactic and glycolic acids) are metabolic compounds. Degradation by hydrolysis refers to the spontaneous breaking of covalent bonds in water without a role for enzymes; hydrolytically degradable materials thus will degrade over time in a solution of water that is free of enzymes. Polyesters such as poly (lactide) (PLA) and its glycolic acid copolymer poly(lactide-co-glycolide) (PLGA) are most commonly used as a drug carrier due to their excellent biocompatibility, biodegradability and mechanical strength. They degrade by hydrolysis of the ester backbone and their degradation products (i.e. lactic and glycolic acids) are metabolic compounds. Incorporation of drug into polyesters can be performed using a variety of techniques, such as: melt extrusion, compression, solvent casting, injection molding, in situ polymerization and micro and/or nanoparticles. Microparticles can be formed by granulation of the aforementioned extruded, compressed or cast polymer systems, or they can be formed using techniques such as: spray drying, spray-freeze drying, phase separation (coacervation) and solvent evaporation. Solvent evaporation may employ different techniques, as illustrated in the figure below to encapsulate the drug dependent upon the lipophilicity and/or hydrophilicity of the drug.

Incorporation of agents into polyesters can be performed using a variety of techniques, such as: melt extrusion, compression, solvent casting, injection molding, in-situ polymerization and micro and/or nanoparticles. Microparticles can be formed by granulation of the aforementioned extruded, compressed or cast polymer systems, or they can be formed using techniques such as: spray drying, spray-freeze drying, phase separation (coacervation) and solvent evaporation. Solvent evaporation may employ different techniques, as illustrated in FIG. 5 below to encapsulate the drug dependent upon the lipophilicity and/or hydrophilicity of the agent.

Figure 5:
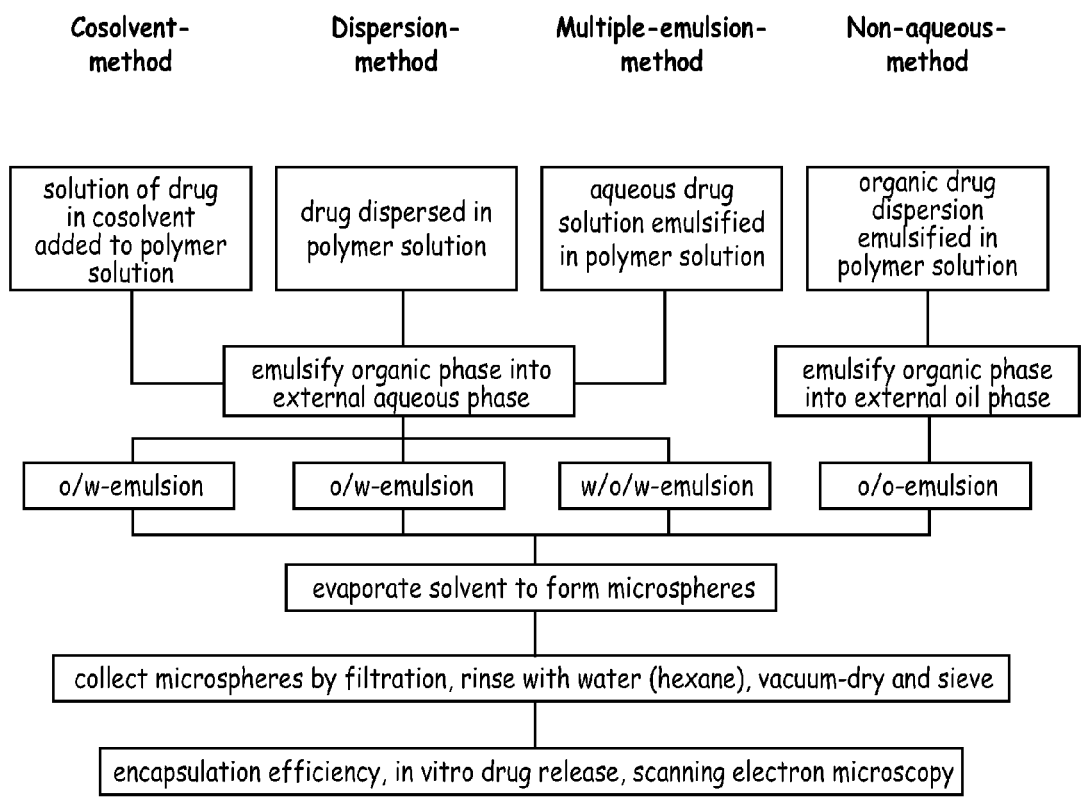
FIG. 5 is a flow chart depicting options for formation of microparticles for drug delivery.

With respect to microparticle fabrication techniques, hydrophilic agents are typically incorporated in the inner aqueous phase (see multiple emulsion method of FIG. 5) or as solids dispersed in the oil phase (see dispersion method of FIG. 5), whereas lipophilic agents are generally dissolved in the organic/oil phase (see cosolvent method of FIG. 5). With respect to solvent casting, the agents are incorporated similarly to the cosolvent method minus the continuous phase necessary for microparticle formation. With respect to melt extrusion or compression techniques, the agents are generally incorporated in their initial state in the absence of solvent. Variations of these incorporation techniques exist and should be adjusted on a case-by-case basis, as multiple variables (e.g., drug loading, solubility, solvent selection and blends, polymer concentration, polymer type and blends, excipients, targeted release duration, drug stability, etc.) play a role in selecting the best choice to incorporate the drug into the polymer matrix.

Agent release from implants, microparticles and to a large extent in situ forming devices is dependent upon and can be adjusted by multiple factors to modulate the sustained and/or burst release. Some of the factors that influence agent release from these biodegradable polymer systems are listed in Table 1.

TABLE 1

Factors Potentially Influencing the Sustained and/or Burst Release from PLA and PLGA Biodegradable Systems (not ordered for significance)

| | |
|---|---|
| Polymer molecular weight | Polymer concentration |
| Molecular weight distribution | Drug load |
| End-group chemistry | Inner-emulsion size |
| Lactide/glycolide ratio | Inner-particulate size |
| Crystalline vs. amorphous | Excipients |
| Drug load | Drug product stability |
| Drug solubility | Product drying and rate of drying |
| Device geometry (surface area) | Residual solvents |
| Hydrophilicity/hydrophobicity | pH |
| Porosity | Temperature |
| Drug/polymer interactions | Solvent type and concentration |
| Injection location and concentration | |

Biodegradation

The hydrogel is, in general, water-degradable, as measurable by the hydrogel being dissolvable in vitro in an excess of water by degradation of water-degradable groups. This test is predictive of hydrolytically-driven dissolution in vivo, a process that is in contrast to cell or protease-driven degradation. The hydrogels can be selected to be absorbable over days, weeks, or months, depending on the drug selected, disease being treated, the duration for release that is needed, and the release profile of the specific drug selected.

The biodegradable linkage may be water-degradable or enzymatically degradable. Illustrative water-degradable biodegradable linkages include polymers, copolymers and oligomers of glycolide, dl-lactide, l-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly(carbonate)s, poly(phosphonate)s.

Significantly, however, polyanhydrides or other conventionally-used degradable materials that degrade to acidic components tend to cause inflammation in the eye. The hydrogels, however, may exclude such materials, and may be free of polyanhydrides, anhydride bonds, or precursors that degrade into acid or diacids. Instead, for example, SG (succinimidyl glutarate), SS (succinimidyl succinate), SC (succinimidyl carbonate), SAP (succinimidyl adipate), carboxymethyl hydroxybutyric acid (CM-HBA) may be used and have esteric linkages that are hydrolytically labile. More hydrophobic linkages such as suberate linkages may also be used, with these linkages being less degradable than succinate, glutarate or adipate linkages.

If it is desired that the biocompatible crosslinked polymer be bioresorbable or absorbable, one or more precursors having biodegradable linkages present in between the functional groups may be used. The biodegradable linkage optionally also may serve as the hydrophilic core of one or more of the precursors. For each approach, biodegradable linkages may be chosen such that the resulting biodegradable biocompatible crosslinked polymer will degrade or be absorbed in a desired period of time.

The crosslinked hydrogel degradation will generally proceed by the water-driven hydrolysis of the biodegradable segment when water-degradable materials are used. If polyglycolate is used as the biodegradable segment, for instance, the crosslinked polymer could be made to degrade in about 1 to about 30 days depending on the crosslinking density of the network. Similarly, a polycaprolactone based crosslinked network can be made to tend to degrade in about 1 to about 8 months. The degradation time generally varies according to the type of degradable segment used, in the following order: polyglycolate<polylactate<polytrimethylene carbonate<polycaprolactone. Polymers that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment.

Similarly, biodegradable capsules or particles may be made for inclusion within a hydrogel matrix. The capsules or particles may have a degradation time that is the same as, or different from, the hydrogel matrix.

Hydrogels for Punctal Plugs

The hydrogels may be used as punctal plugs (punctum plug or intracanalicular plug). Various shapes and sizes for punctal plugs are known. The simplest shape may be a solid rod that is flat or rounded at its ends. The rod may be substantially cylindrical in its exterior shape, meaning that it has no protuberances, but has straight sides. Alternatively, the rod may have a head portion and a shaft portion before swelling. For use as a punctal plug, the length of a desiccated or dehydrated hydrogel may be, for instance, from about 0.5 mm to about 15 mm; artisans will immediately appreciate that all the ranges and values within the explicitly stated ranges are contemplated, e.g., from about 2 to about 4 mm. For a generally oblong hydrogel, a width of, e.g., from about 0.1 to about 1.0 mm may be used. For instance, about 0.3 mm diameter in the case of swelling of about 2× after placement will provide a snug fit for most patients. As is evident from reading this disclosure, a greater swelling rate will provide for smaller diameter plugs to be used, and such smaller sizes are contemplated. A "universal fit" plug is preferred over plugs that need to be sized for a particular punctum (as is the case for poly (caprolactone-co-lactide) or silicone plugs)

Hydrogels as described herein may be used as a punctal plug. The high-swelling hydrogels are useful for providing a firm positioning once swollen in place. The firm positioning and comfort of a pliable and smooth hydrogel contributes to a high retention, and a high patient compliance for treatment by drugs delivered from the plug. The high swelling also provides for one-size-fits-all-users since it may be made to swell to fit. The all-synthetic nature eliminates variability and sources of contaminants, impurities, immunogens, and allergens. The plugs may be made and used as a single material, meaning that the plugs are made with one matrix material that is the same throughout, e.g., with no added coverings, sleeves, sheathes, overcoats, reservoir portions, or other added materials. Some embodiments are made with a uniform macroscopic structure such that they have no openings into the hydrogel, i.e., the material lack tunnels or macro-pore structures, bearing in mind that a hydrogel will have a certain native porosity. A homogenous plug may include agents dispersed therein. The plugs may be sized for placement without incisions or invasive processes, in contrast to other opthalmological drug release systems.

The plugs may be hydrolytically biodegradable. As explained, hydrolytic degradation refers to a process that is spontaneous in aqueous solution, i.e., occurring without enzymatic action. The biodegradation may be between about 5 to about 365 days; artisans will immediately appreciate that all the ranges and values within the explicitly stated ranges are contemplated, e.g., from about 1 week to about 30 weeks, at least about 30 days, from about 30 days to about 90 days; about 45 days. Hydrolytic degradation is advantageously available for a predictable rate of degradation relative to cell-based or enzyme-based degradation.

The covalently crosslinked hydrogels have advantages over non-crosslinked hydrogels that are not conventionally appreciated. One advantage is that coacervates (alginate) or ionic crosslinks tend to break and re-form as the gel is strained such that there is a permanent shape-change. Thus water can be squeezed out of such materials in a punctal plug setting. But the covalently crosslinked hydrogels absorb water and do not re-form their crosslinks in response to a strain. The covalent crosslinking also may be used to provide for a gel with structural strength that allows firm grasping and forceful removal by forceps or tools even when hydrated.

Figure 10:
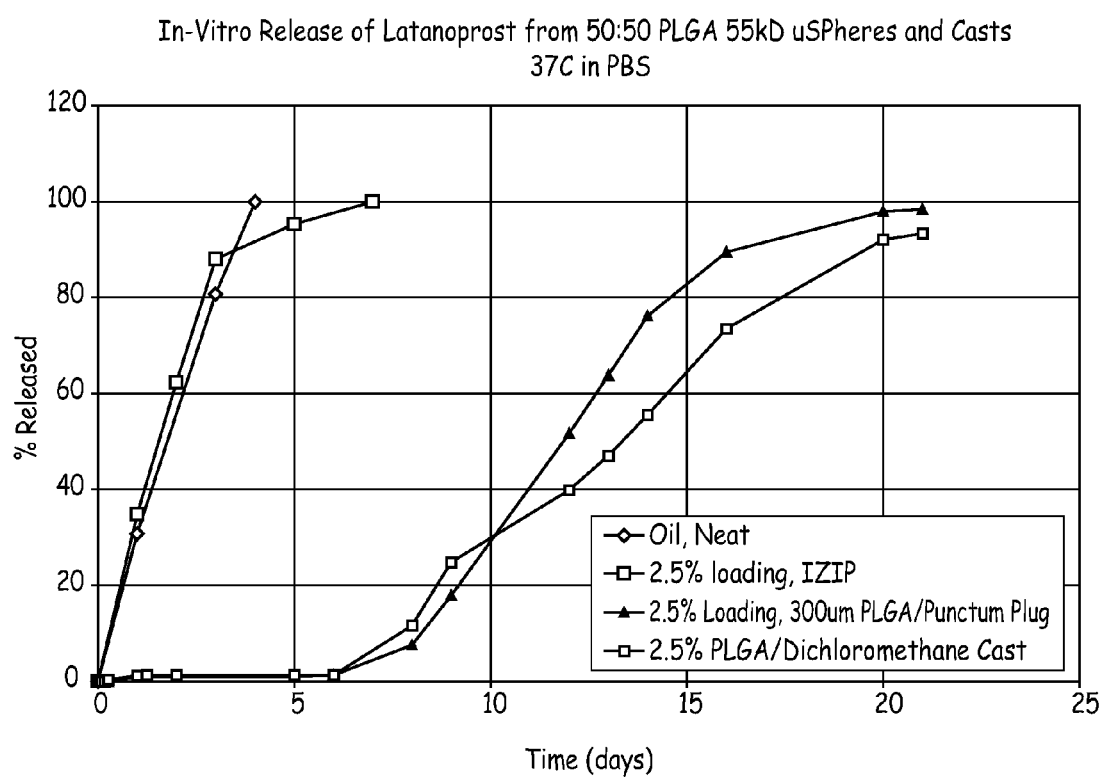
FIG. 10 depicts release of a drug from punctal plug hydrogels and/or from microspheres, as detailed in Example 13.

Some punctal plugs include therapeutic agents that are trapped in particles or capsules that degrade at a different rate than the hydrogel in the punctal plug. A faster rate accelerates drug delivery while a slower rate delays it. A combination of such rates can be used to deliver a desired dosage regimen over time. For instance, a combination of one or more delivery systems as depicted in the Figures will allow for a delivery profile that is a sum of the described rates. For example, FIG. 10 shows a drug that is included in a non-encapsulated form and also provided as a microsphere. The non-encapsulated drug is delivered more quickly and the encapsulated drug is delivered with a delay so that there is a continuous and effective dosage.

Figure 13:
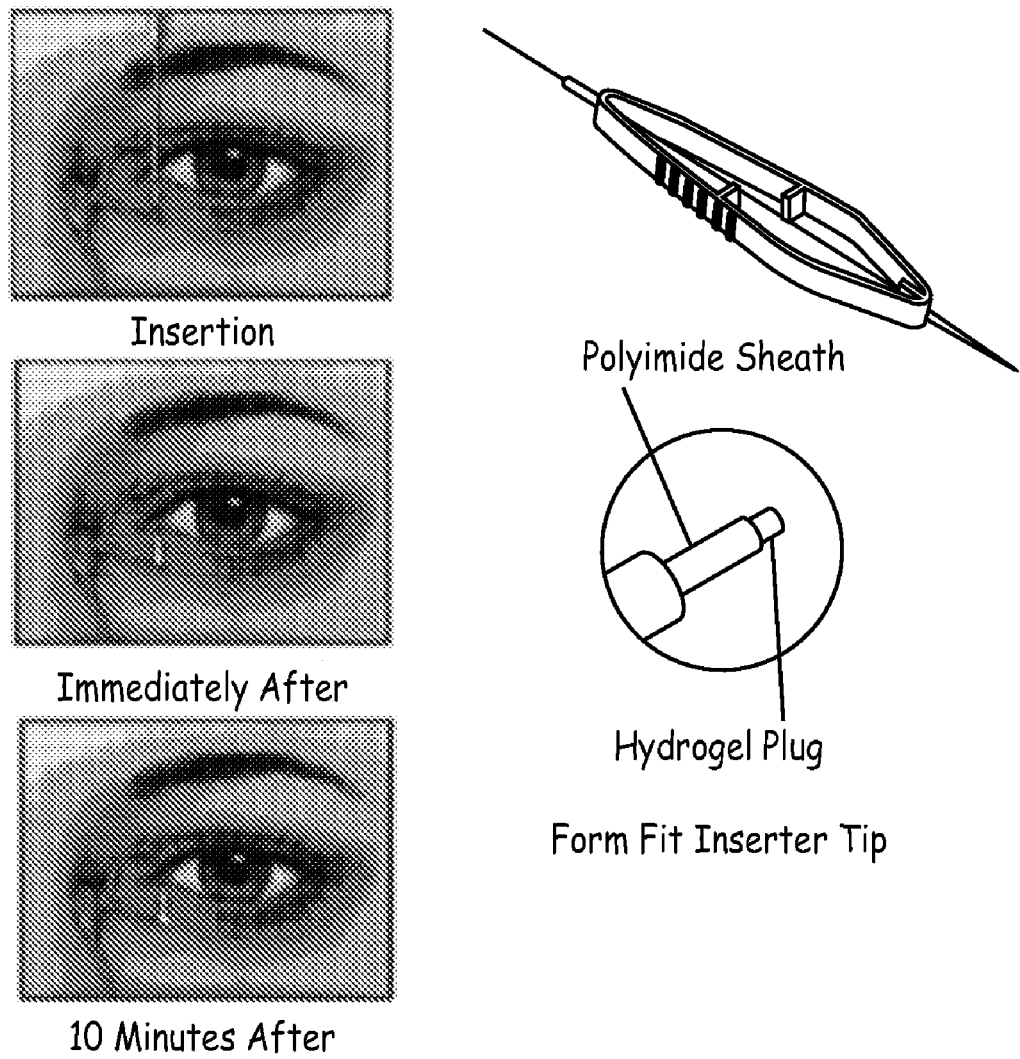
FIG. 13 depicts certain options for punctal plug placement.

FIG. 13 depicts methods for punctal plug placement. One embodiment is to place the punctal plug entirely within the patient so that none of the plug is outside the punctum. The top of the plug may be placed flush with the punctum to provide a seat in the punctum without extending from the patient. Another embodiment is the placement of the punctal plug with a portion outside the punctum so that, upon swelling, a "head" for the plug is created. The head may be readily grasped for easy removal in the case of an adequately swelling material, e.g., at least 2× or 4× increase in volume.

Some embodiments include punctal plugs with a hydrophobic coating that delays swelling without stopping the swelling. The coating can assist the user by delaying swelling long enough to assure a suitable fit. In some embodiments, the coating is chosen and applied with a thickness so as to be effective to delay swelling by an average value of between about 10 to about 300 seconds; artisans will immediately appreciate that all the ranges and values within the explicitly stated ranges are contemplated, e.g., an average delay of about 15 seconds or 30 seconds or from about 30 seconds to about 60 seconds. Exemplary thicknesses are about 1 to about 1000 microns; artisans will immediately appreciate that all the ranges and values within the explicitly stated ranges are contemplated, e.g., from about 10 to about 100 microns, less than about 800 microns, or about 100 to about 500 microns.

Punctal plugs may be made using the materials as described herein and also used for drug delivery as described herein. Accordingly, an embodiment of a punctal plug and process for making the same is a rod formed from a microparticulate basic salts (e.g., sodium borate dihydrate or sodium phosphate dibasic) and microparticulate trilysine. The components are added into a solution of a modified polyethylene glycol (PEG) in dimethylcarbonate (DMC) to form a suspension. The suspension is then dried to form a solid containing the suspended particles. The solid can then be melted and shaped to form a punctum plug. The PEG is modified such that it can react with the trilysine to form a crosslinked hydrogel. By forming the suspension in DMC, a solvent for PEG but a non-solvent for trilysine and the salts, the reactive species cannot comingle and react. Addition of water provides a common solvent for all three components, which allows the reaction to proceed. The plug is then inserted into the moist punctum. On contact with moisture, the plug absorbs the water, liquefies and swells as it reacts to form a hydrogel in situ. The process of forming the suspension can be varied to achieve gel time, swelling and modulus as described herein. Drugs may be incorporated into the suspension for release into the tear fluid or tissues for therapeutic purposes.

Therapeutic Agents for Delivery

The hydrogels may include a therapeutic agent. Punctal plugs that have the hydrogel may be used to deliver the therapeutic agents. Treatment of specific eye conditions depends on delivering a suitable dose of the agent to the eye over a suitable period of time. Table 2 sets forth some embodiments of conditions and treatments.

TABLE 2

Conditions and Corresponding Treatment.

| Item | Condition | Drug Class For Treatment | Examples |
|---|---|---|---|
| 1 | Dry Eye | Immunosuppressant | Cyclosporine A |
| 2 | Keratoconjunctivitis sicca | Immunosuppressant Anti-inflammatory | Cyclosporine A Prednisolone acetate |
| 3 | Blepharitis | Anti-inflammatory Antibiotic | Dexamethasone Tobramycin |
| 4 | Keratitis | Antibiotic | Moxifloxacin Gatifloxacin |

TABLE 2-continued

Conditions and Corresponding Treatment.

| Item | Condition | Drug Class For Treatment | Examples |
|---|---|---|---|
| 4 | Scleritis | Anti-inflammatory (NSAID) | Ibuprofen |
|  |  | Anti-inflammatory Antibiotic | Prednisolone acetate Moxifloxacin Gatifloxacin |
| 5 | Iritis | Anti-inflammatory | Prednisolone acetate |
| 6 | Uveitis | Anti-inflammatory | Prednisolone acetate |
| 7 | Conjunctivitis | Antibiotic | Moxifloxacin Gatifloxacin |
| 8 | Glaucoma | Prostaglandins | Latanoprost Travaprost |
|  |  | Beta Blockers | Timolol |
| 9 | Corneal Ulcer | Antibiotic | Moxifloxacin Gatifloxacin |
| 10 | Corneal Abrasion | Antibiotic | Moxifloxacin Gatifloxacin |
|  |  | Anticholinergic/ Cycloplegic | Atropine Tropicamide |

The hydrogel may be used to deliver classes of drugs including steroids, Non-steroidal anti-inflammatory drugs (NSAIDS), intraocular pressure lowering drugs, antibiotics, or others. The hydrogel may be used to deliver drugs and therapeutic agents, e.g., an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). The rate of release from the hydrogel will depend on the properties of the drug and the hydrogel, with factors including drug sizes, relative hydrophobicities, hydrogel density, hydrogel solids content, and the presence of other drug delivery motifs, e.g., microparticles.

The hydrogel precursor may be used to deliver classes of drugs including steroids, NSAIDS (See Table 3), intraocular pressure lowering drugs, antibiotics, pain relievers, inhibitors or vascular endothelial growth factor (VEGF), chemotherapeutics, anti viral drugs etc. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations. The drugs that have low water solubility may be incorporated, e.g., as particulates or as a suspension. Higher water solubility drugs may be loaded within microparticles or liposomes. Microparticles can be formed from, e.g., PLGA or fatty acids.

TABLE 3

NSAIDS that may be delivered.

| Item | Drug | Structure | Solubility |
|---|---|---|---|
| 1 | Ibuprofen | 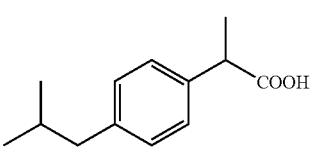 | 10 mg/ml @ pH 7 |

TABLE 3-continued

NSAIDS that may be delivered.

| Item | Drug | Structure | Solubility |
|---|---|---|---|
| 2 | Meclofenamate sodium | 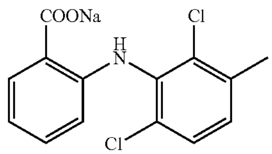 | <50 μg/mL @ pH 7.2<br>50 mg/mL @ pH 9.0 |
| 3 | Mefanamic Acid | 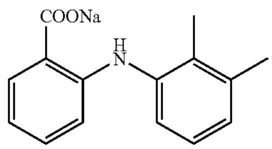 | 40 μg/ml @ pH 7.1 |
| 4 | Salsalate | 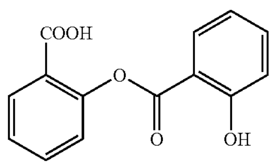 [SMILES: O=C(Oc1ccccc1C(=O)O)c1ccccc1O] | |
| 5 | Sulindac | 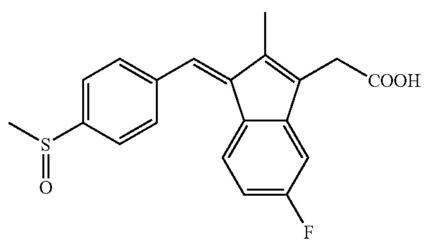 [SMILES: CC1=C(CC(=O)O)c2cc(F)ccc2/C1=C\c1ccc(S(C)=O)cc1] | Practically insoluble below pH 4.5: Very soluble > pH 6 |
| 6 | Tolmetin sodium | 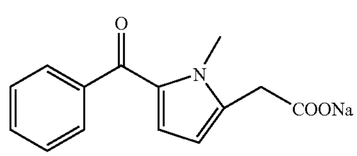 | Freely soluble in water |
| 7 | Ketoprofen | 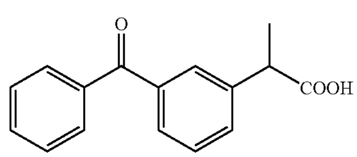 [SMILES: CC(C(=O)O)c1cccc(C(=O)c2ccccc2)c1] | Not less than 0.25 mg/ml @ pH 7.35 |
| 8 | Diflunisal | 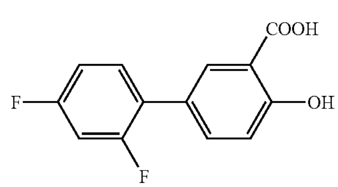 [SMILES: O=C(O)c1cc(-c2ccc(F)cc2F)ccc1O] | 3.43 mg/ml @ pH 7 |
| 9 | Piroxicam | 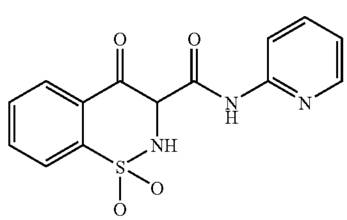 [SMILES: O=C(Nc1ccccn1)C1NS(O)(O)c2ccccc2C1=O] | 0.03 mg/ml |

TABLE 3-continued

NSAIDS that may be delivered.

| Item | Drug | Structure | Solubility |
|---|---|---|---|
| 10 | Naproxen | 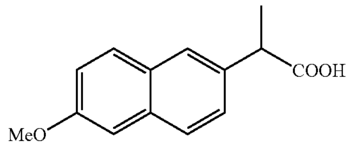 [SMILES: COc1ccc2cc(C(C)C(=O)O)ccc2c1] | Freely soluble at pH 8 |
| 11 | Etodolac | 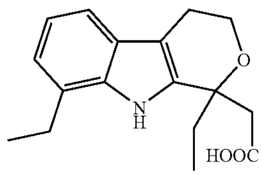 [SMILES: CCc1cccc2c3c([nH]c12)C(CC)(CC(=O)O)OCC3] | Insoluble in water |
| 12 | Flurbiprofen | 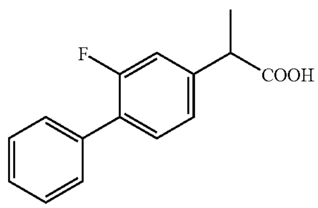 [SMILES: CC(C(=O)O)c1ccc(-c2ccccc2)c(F)c1] | 0.9 mg/mL |
| 13 | Fenoprofen Calcium | 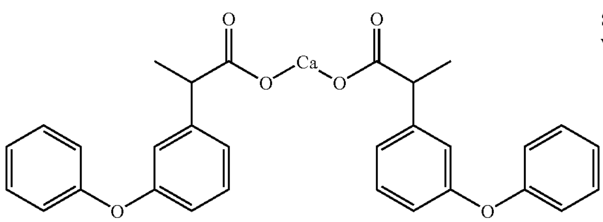 | Slightly soluble in water |
| 14 | Indomethacin | 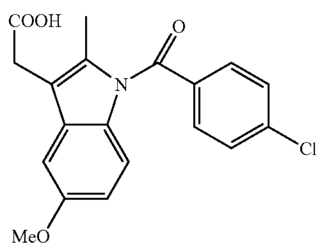 [SMILES: COc1ccc2c(c1)c(CC(=O)O)c(C)n2C(=O)c1ccc(Cl)cc1] | @ pH 7<br>Form I: 0.54 mg/ml<br>Form II: 0.80 mg/ml |
| 15 | Celecoxib | 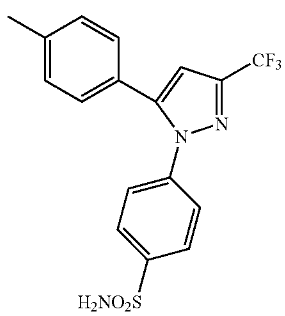 [SMILES: Cc1ccc(-c2cc(C(F)(F)F)nn2-c2ccc(S(N)(=O)=O)cc2)cc1] | 5 µg/ml |
| 16 | Ketorolac | 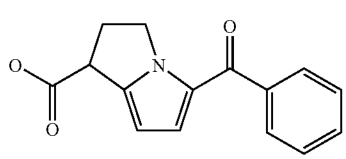 [SMILES: O=C(c1ccccc1)c1ccc2n1CCC2C(=O)O] | 10.5 mg/ml in IPB;<br>25 mg/ml<br>as tromethamine salt. |

TABLE 3-continued

NSAIDS that may be delivered.

| Item | Drug | Structure | Solubility |
|---|---|---|---|
| 17 | Nepafenac | 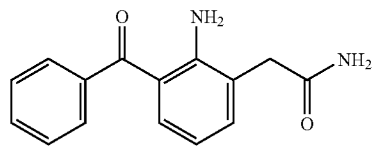 [SMILES: NC(=O)Cc1cccc(C(=O)c2ccccc2)c1N] | <1 mg/ml (The drug is available as 0.1% suspension) |

A variety of drugs or other therapeutic agents may be delivered using these systems. A list of agents or families of drugs and examples of indications for the agents are provided. The agents may also be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure—open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure—open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefrin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

One embodiment comprises extended release of a medication for allergic conjunctivitis. For instance, ketotifen, an antihistamine and mast cell stabilizer, may be released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Moxifloxacin is the active ingredient in VIGAMOX, which is a fluoroquinolone approved for use to treat or prevent ophthalmic bacterial infections. Dosage is typically one-drop of a 0.5% solution that is administered 3 times a day for a period of one-week or more. Herein is described a moxifloxacin loaded hydrogel, e.g, a punctal plug, which has a dried polyethylene glycol (PEG) based hydrogel rod designed to be placed in the vertical canaliculus with forceps following probe dilation. After placement the plug swells on contact with moisture thereby occluding the lumen and locking it in place for the duration of therapy. Embedded in the rod are both polylactide-co-glycolide microspheres containing encapsulated moxifloxacin and non-encapsulated free drug substance (moxifloxacin). The microspheres are bioresorbable particles which encapsulate the drug and are formulated to release the drug via hydrolysis over an extended period of time. The non-encapsulated free drug substance immediately releases upon hydration of the plug. Such a device may be used, for example for treatment of bacterial conjunctivitis caused by strains of bacteria with pre-determined susceptibility to topical ophthalmic moxifloxacin. The moxifloxacin punctal plug is to be retained in the canaliculus over a course of about 10 days. Alternatively, other formulations may be used for a different time course, e.g., about 6 or about 14 days, or another time within the range of about 3 days to about 30 days; artisans will immediately appreciate that all the ranges and values within the explicitly stated ranges are contemplated. Exemplary loading is from about 100 to about 1000 g per plug, with the plug having a volume of less than about 1 cubic millimeter.

VKC and AKC are chronic allergic diseases where eosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis.

Accordingly, embodiments include hydrogels that incorporate one or more of the agents. The agents may be incorporated using one or more processes herein, e.g., with or without microspheres. The hydrogels may be used to make medicaments for administration of an effective amount of the agent over a predetermined time to treat the conditions indicated.

Some therapeutic agents are visualization agents. A visualization agent may be used with a hydrogel; it reflects or emits light at a wavelength detectable to a human eye so that a user applying the hydrogel can observe the gel. Some useful visualization agents are FD&C BLUE #1, FD&C BLUE #2, and methylene blue. Such agents may be used with punctal plug and/or microsphere and/or hydrogel embodiments set forth herein.

These agents, when dispersed in a hydrogel, are preferably present at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. These concentration ranges can give a color to the hydrogel without interfering with crosslinking times for electrophilic-nucleophilic reactive precursor embodiments (as measured by the time for the reactive precursor species to gel).

Visualization agents may be selected from among any of the various non-toxic colored substances suitable for use in medical implantable medical devices, such as FD&C BLUE dyes 3 and 6, eosin, methylene blue, indocyanine green or colored dyes normally found in synthetic surgical sutures. The visualization agent may be present with either reactive precursor species, e.g., a crosslinker or functional polymer solution. The preferred colored substance may or may not become chemically bound to the hydrogel. The visualization agent may generally be used in small quantities, preferably less than 1% weight/volume, more preferably less that 0.01% weight/volume and most preferably less than 0.001% weight/volume concentration.

Additional machine-aided imaging agents may be used, such as fluorescent compounds, x-ray contrast agents (e.g., iodinated compounds) for imaging under x-ray imaging equipment, ultrasonic contrast agents, or MRI contrast agents (e.g., Gadolinium containing compounds).

Visualization agents have advantages that were not foreseen prior to studying degradation of materials used for punctal applications. Plugs or hydrogels are subject to compressive forces that tend to displace them as the materials degrade. But the materials need to remain in place when used for drug delivery. A comfortably placed material, however, can be displaced without a patient noticing this fact. Incorporation of a visualization agent at a concentration that is effective for visualization, however, allows for the user to monitor the ongoing presence of the material and take steps to obtain a replacement if the plug or other material is displaced prior to completion of a therapeutic regimen. Agents that are visible to the naked eye without machine-aid can thus be used in an amount effective for a patient to visualize the presence or absence of the material. Accordingly, embodiments include using an effective amount of a visualization agent and checking the plug or other material periodically (e.g., daily) for the presence of the same.

The materials or devices described herein may be used to deliver drugs or other therapeutic agents (e.g., imaging agents or markers) to eyes or tissues nearby. For instance, a punctal plug may be used to deliver an agent to a surface of an eye, i.e., topically. It has also been discovered that the agents may be delivered in an amount effective to have a therapeutic effect in the anterior segment of an eye. Such delivery may be accomplished by a plug or by a depot or microdepot placed on or near the eye.

Some of the disease states that may be thus treated are back-of-the-eye diseases. The term back-of-the eye disease is recognized by artisans in these fields of endeavor and generally refers to any ocular disease of the posterior segment that affects the vasculature and integrity of the retina, macula or choroid leading to visual acuity disturbances, loss of sight or blindness. Disease states of the posterior segment may result from age, trauma, surgical interventions, and hereditary factors. Some back-of-the-eye disease are; age-related macular degeneration (AMD) cystoid macular edema (CME), diabetic macular edema (DME), posterior uveitis, and diabetic retinopathy. Some back-of-the-eye diseases result from unwanted angiogenesis or vascular proliferation, such as macular degeneration or diabetic retinopathy. Drug treatment options for these and other conditions are further discussed elsewhere herein.

In using the crosslinked composition for drug delivery as mentioned above, the amount of crosslinkable polymer, crosslinker and the dosage agent introduced in the host will necessarily depend upon the particular drug and the condition to be treated. Administration may be by any convenient means such as syringe, cannula, trocar, catheter and the like.

Kits or Systems

Kits or systems for making hydrogels may be prepared. The kits are manufactured using medically acceptable conditions and contain precursors that have sterility, purity and preparation that is pharmaceutically acceptable. The kit may contain an applicator as appropriate, as well as instructions. A therapeutic agent may be included pre-mixed or available for mixing. Solvents/solutions may be provided in the kit or separately, or the components may be pre-mixed with the solvent. The kit may include syringes and/or needles for mixing and/or delivery.

In some embodiments, the kit has at least one precursor and an applicator. In some embodiments, a biodegradable, polymeric, synthetic hydrogel is formed by the reaction of multiaimed polyethylene glycol (PEG) having succinimidyl esters on each terminus of each arm with trilysine (which has primary amine nucleophiles) in phosphate or other buffer solutions.

In some embodiments, kits having precursors and other materials as needed to form a hydrogel in situ with a therapeutic agent may be provided, with the component parts including those described herein. In some aspects, features of the hydrogels can thus be chosen to make hydrogels that are high-swelling and delivered through a small needle. The hydrogel is not inflammatory or angiogenic, relies on biocompatible precursors, and is soft, hydrophilic, and swells the space wherein it is placed. The hydrogel may be easily removable or self-removing, and can be biodegradable or suited to delivery to easily accessible areas without dispersal. It can be made so it is easy to mix and use, with an option to combine all the precursors in a single container. The hydrogel may be made with safe, all-synthetic materials. The degradation and/or delivery rate may be controlled to fit the time periods described. Patient compliance may be enhanced by avoiding repeated dosing. Similarly kits with an applicator may be made that include a material as set forth herein, e.g., a pre-formed dehydrated hydrogel.

The use of fluent aqueous precursors to form a punctal plug in situ allows for administration through small (e.g., 30 gauge) needles. Also, since the hydrogel can be made to minimize acidic by-products, the plugs are well tolerated by sensitive tissues, such as the eye.

Manufacture and Kinetics, Release Profiles

Various examples are set forth of methods for the manufacture of hydrogels and hydrogel punctal plugs with drug delivery capabilities. In general, the working examples are cast in terms of an erodible or non-erodible device made comprising polyethylene glycol containing agents targeted at topical delivery the tear fluid of the eye. Examples of agents include prostaglandins, anti-inflammatories, immunomodulators, antihistamines, NSAIDS, antibiotics, steroids, and anesthetics. The device may be pre-formed and provided as a dried, drug loaded device, or provided as a liquid formulation to be administered to the eye and formed in-situ in the punctum. As is evident, the working examples demonstrate the more general disclosure without limiting it.

Figure 6:
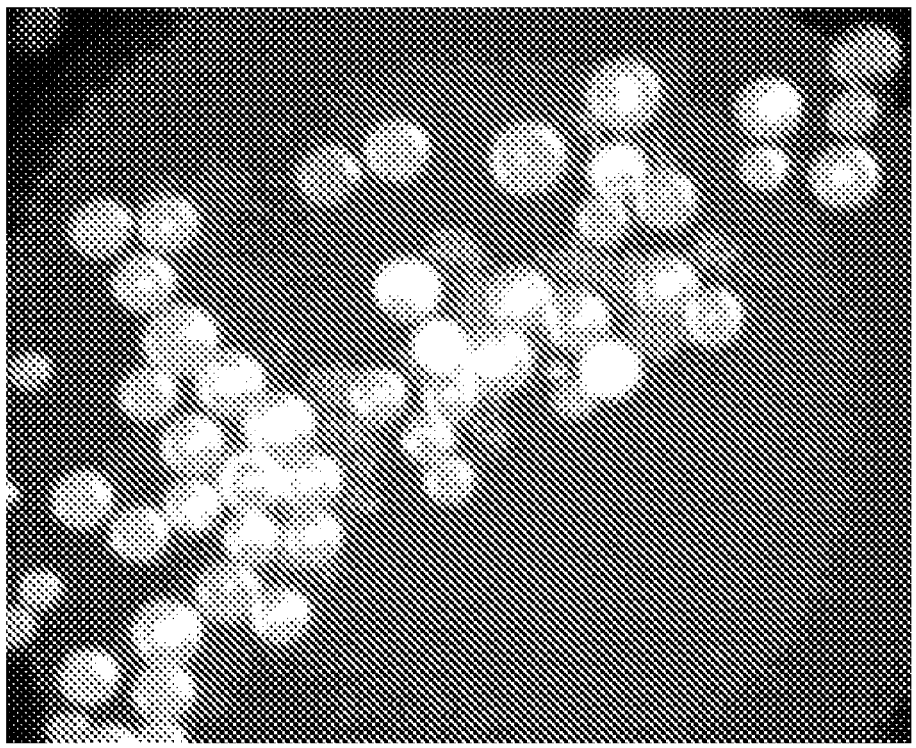
FIG. 6 is a photomicrograph of microspheres containing a drug.

Examples 1, 2, and 3 describe options for an organic-solvent based, methanol-based, or aqueous-based process, respectively, for forming a hydrogel, e.g., as a punctal plug or a depot (or microdepot). The hydrogels may also be formed in situ, e.g, in a canaliculus or as a depot, e.g, topically or subconjunctivally, as in Example 4. Various microsphere formation methods are described. Example 5 uses the hydrophobic drug latanoprost as an example. The term hydrophobic is known to artisans and refers to a material that is substantially insoluble in water even if pH and ionic conditions are adjusted, recognizing that hydrophobic materials theoretically have some very small amount of solubility. A water soluble drug or polymer has a solubility of at least 1 g/100 mL in an aqueous solution. A substantially water soluble material is not hydrophobic but does not dissolve at 1 g/100 mL in water. FIG. 6 depicts a collection of microspheres made using an organic solvent based method; images of particles made by the other methods are comparable. Example 6 provides a prophetic example of a variation of this method, with a transfer agent used.

Films and wafers may be made containing drugs, with the drug dispersed in the same. The material may be chopped or ground to make particles, or used whole as a hydrogel. Examples 7-9 and 18 describe how this process was performed, or variations that could be performed.

Figure 7:
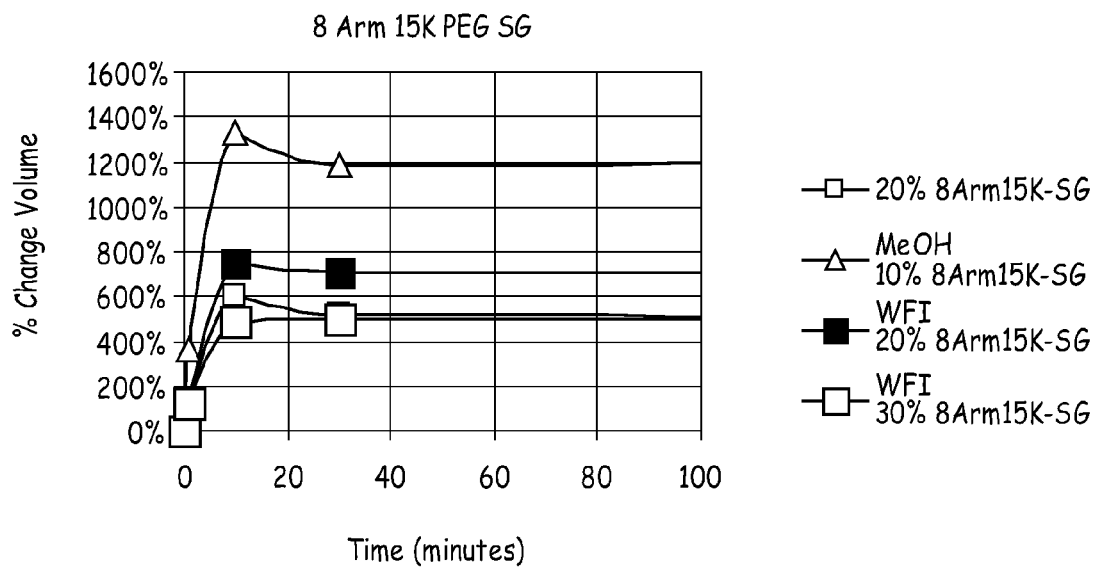
FIG. 7 is a graph depicting swelling of variously formed embodiments of punctal plugs, as detailed in Example 10.

Example 10 describes a high-swelling hydrogel, see also FIG. 7. Volume changes of over 500% were observed. Variously formed hydrogels using organic or aqueous chemistries were observed to be useful for making swellable hydrogels, as in Examples 11-12 and FIGS. 7-9.

Figure 11:
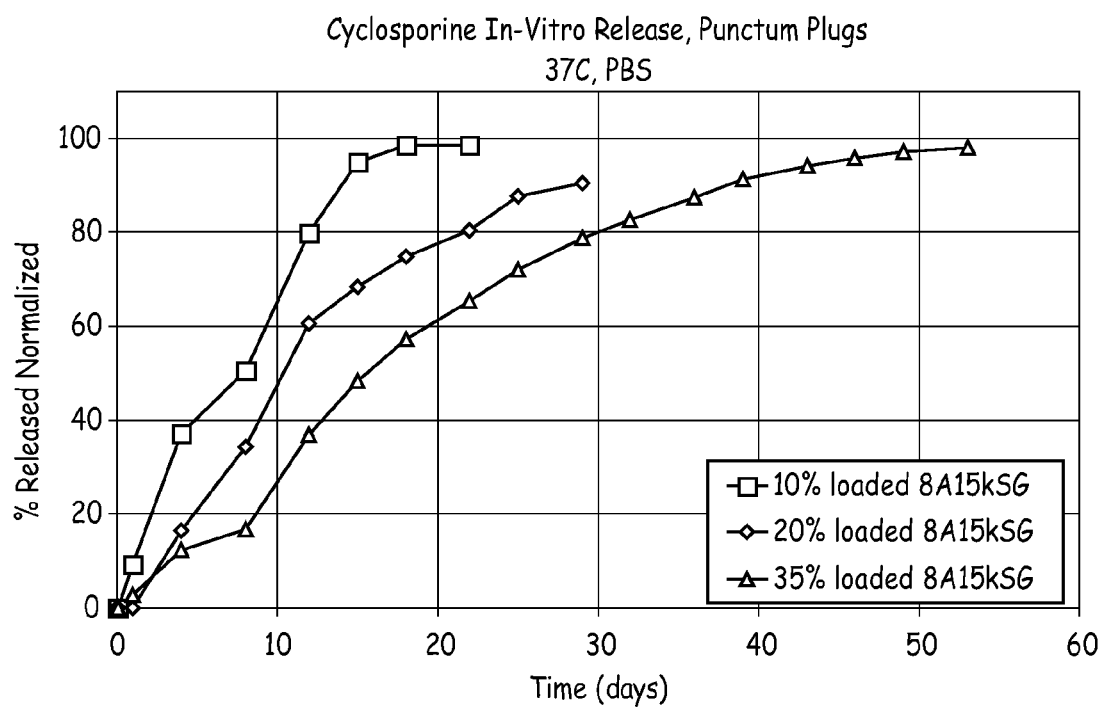
FIG. 11 depicts release of a drug from punctal plug hydrogels and/or from microspheres, as detailed in Example 14.

FIG. 10 (Examples 5 and 13) shows release kinetics for a hydrophobic drug entrapped within particular hydrogels, dispersed freely within the hydrogel, or dispersed after encapsulation in microspheres. The neat (free) drug was released quickly but, significantly, in a zero-order profile. In contrast, the drug in the microspheres entrapped in the hydrogel had a lengthy delayed release (no initial burst). The loading of the drug into the hydrogel was at 2.5%. The percentage loading was discovered to have an unexpected effect on release: FIG. 11 (Example 14) shows release of a hydrophobic drug (cyclosporine) that was not encapsulated, with only the percent loading being varied. More loading caused the kinetics of the release to drop as measured in terms of the percentage of total release from the material. This effect points to an unpredicted property of the systems that can be used to contribute to making a desired release profile. Without being bound to a particular theory, it seems that the hydrogel simply has a limited amount of internal space for fluid, with the space becoming saturated and limiting release. On the other hand, this property can have a confounding effect on predicting if a release profile can be achieved.

The hydrophobic drugs also limited swelling, as shown in FIG. 12. As loading was increased, less swelling was observed. This effect was not predicable a priori. It might be expected that the terminal swelling would be the same for all the hydrogels after the drug was mostly released, but such was not the case. The shrinkage after substantial release was also not expected.

Examples 15 and 16 exemplify the formation of short-term degradable hydrogels and relatively longer-term degradable hydrogels. The short-term materials (Example 15) were made with a succinimidyl glutarate whereas the relatively longer-degradable materials (Example 16) were made with succinimidyl adipates. Examples demonstrating long-term release used the longer term materials (as in implantation of latanoprost-containing materials releasing drugs over weeks for longer-acting inserts) and the short-term release studies used the short-term degrading materials (as is moxifloxacin released over days).

Example 17 describes embodiments that were made for releasing a hydrophilic or a hydrophobic material over a long or short term. Microspheres were prepared for these systems, with Example 17C describing a variation that could have been used.

Figure 15A:
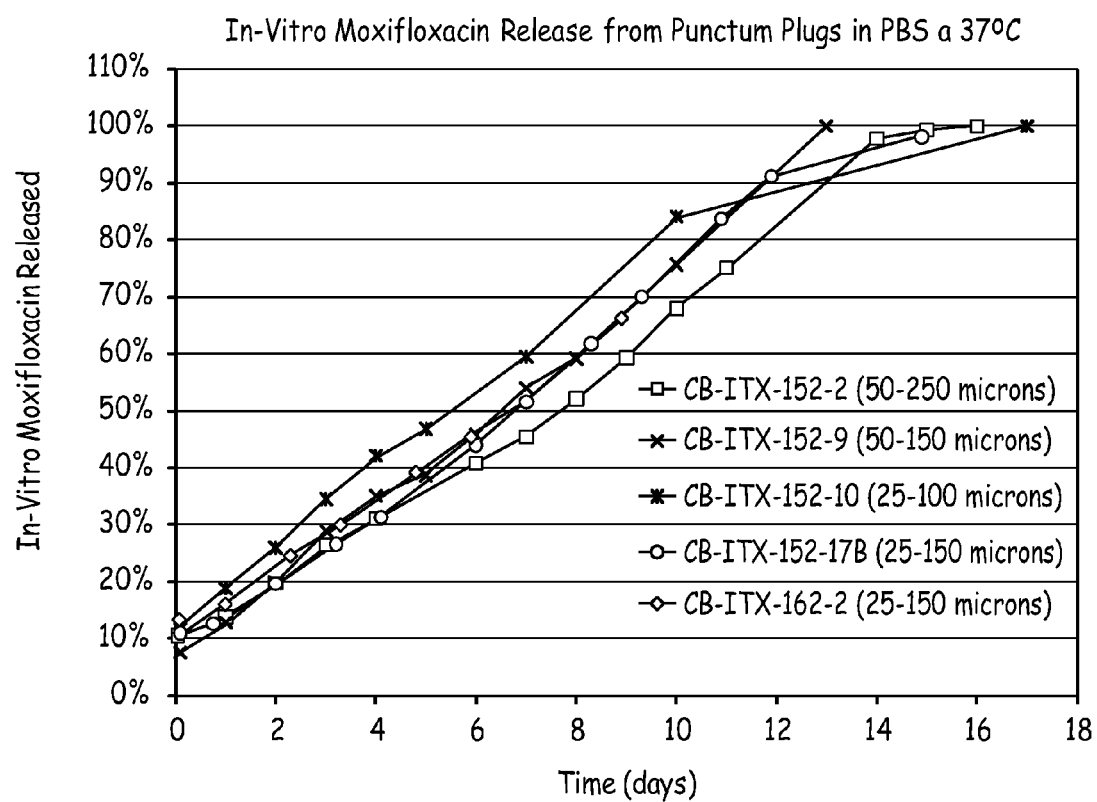
FIG. 15A is a plot showing fabrication and release rate kinetics, as detailed in Examples 18-19.
Figure 15B:
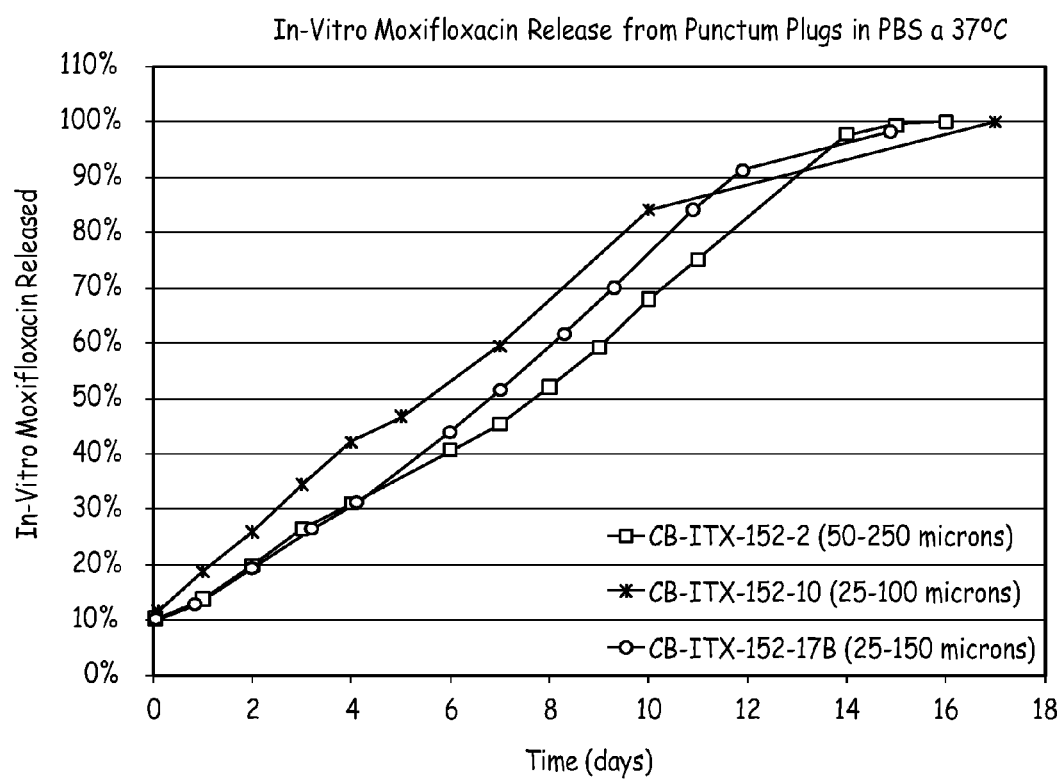
FIG. 15B is a plot of release kinetics as related to microparticle size ranges.
Figure 15C:
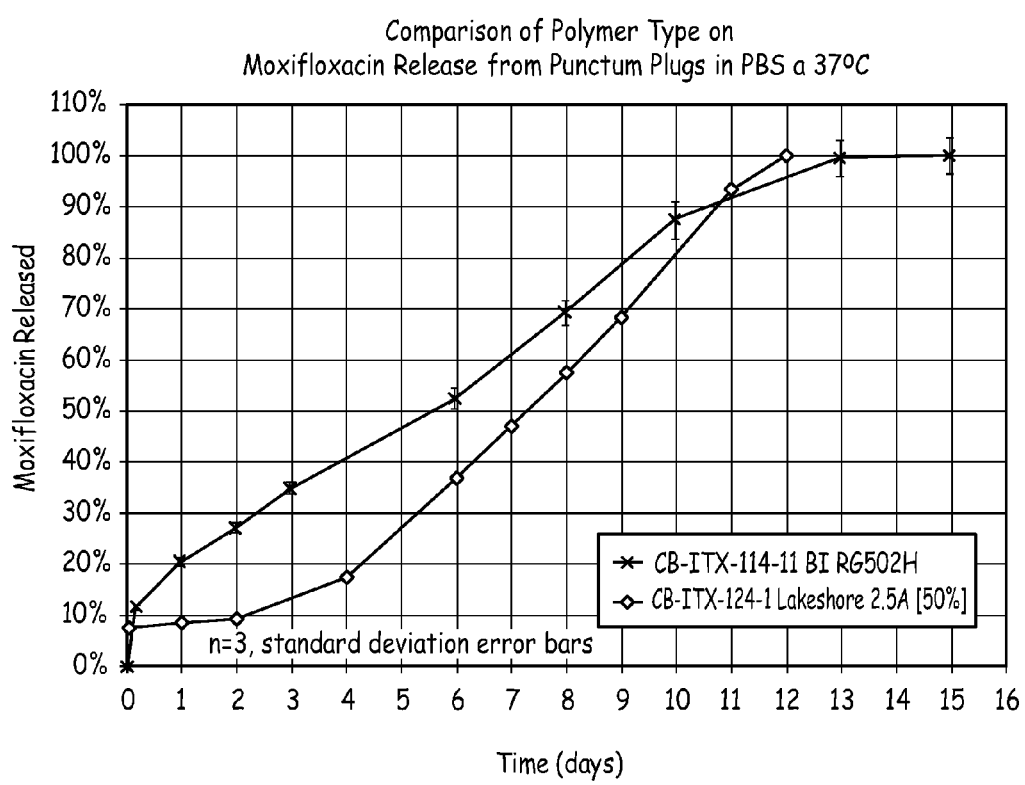
FIG. 15C is a plot of PLGA molecular weight effects on release kinetics.
Figure 15D:
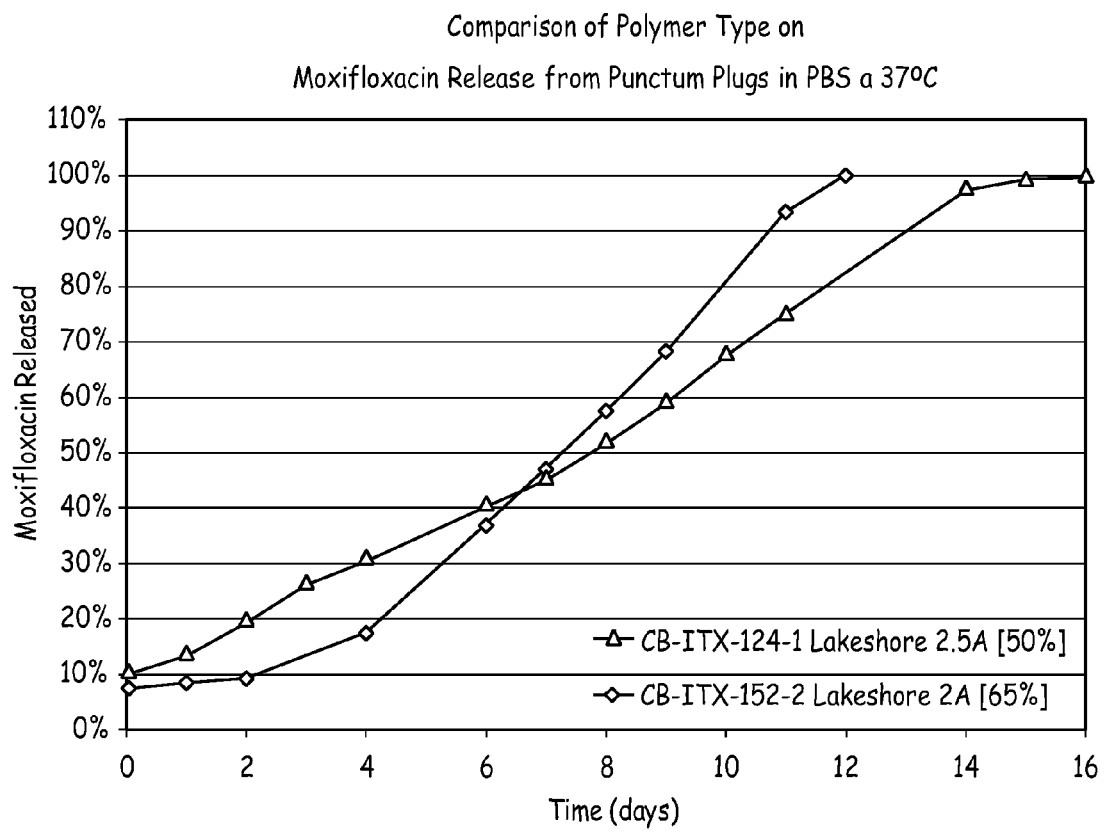
FIG. 15D is a plot showing release kinetic adjustments through molecular weight and concentrations.

The size range of microspheres was discovered to be manipulable to affect control release kinetics in systems with hydrogels containing the particles. FIG. 15A (Example 19A) shows that the smaller microparticles released drug more quickly, as is evident by comparing the plots and observing the release trend from small to large molecules. FIG. 15B is a plot of some the same data as 15A that shows the trend more plainly. The molecular weight and distribution of the PLGA in the microspheres was another variable was manipulated to control release kinetics. A higher molecular weight created a lag period of 2-3 days before release, whereas a lower rate showed a linear release from about day 1 (FIG. 15C). As demonstrated in FIG. 15D, by further changing both the concentration as well as the molecular weight, a formulation was created allowing immediate release but for a prolonged duration. A higher polymer concentration apparently creates a denser microsphere to allow the release period to extend for a longer period.

Figure 15E:
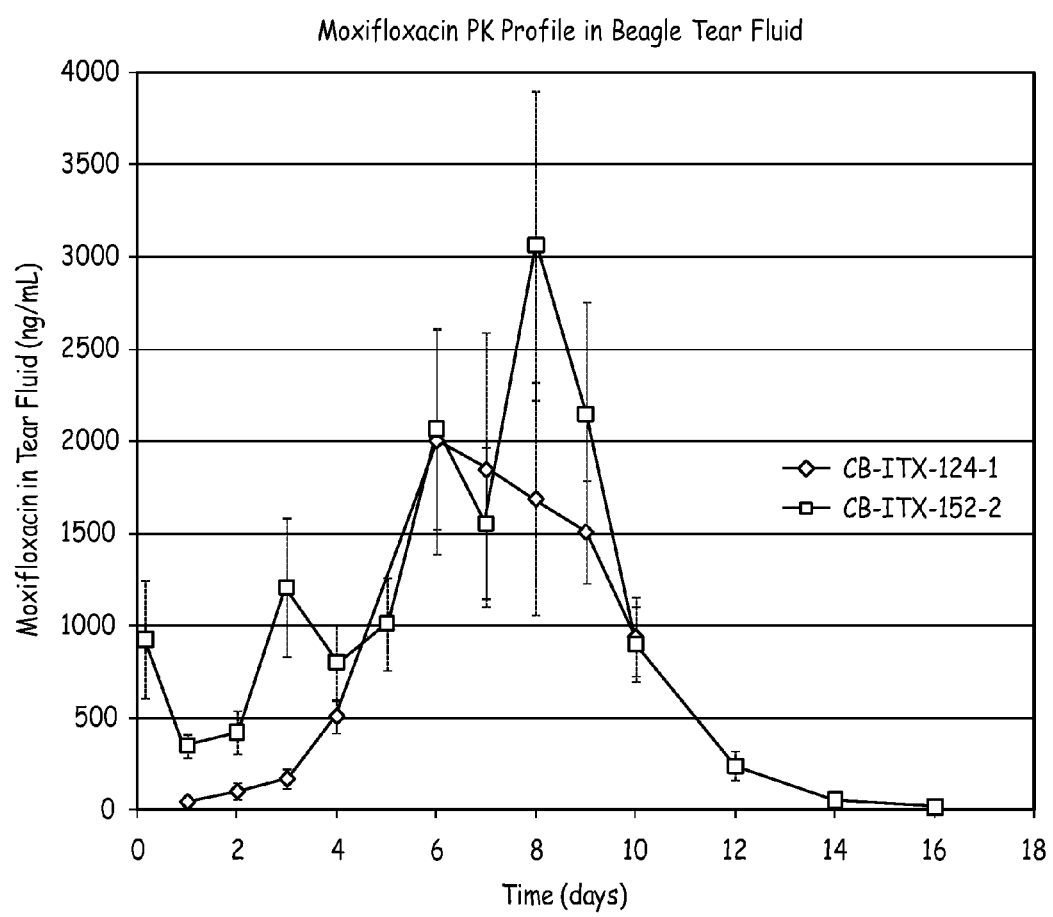
FIG. 15E is a plot relating in vivo and in vitro kinetics.

The elimination of the lag period is useful particularly for immediate action therapeutics like antibiotics. The in vitro lag period observed in FIG. 15D directly translated to an in vivo lag release period in FIG. 15E. Reformulation using a lower molecular weight formulation (denoted as CB-ITX-152-2) compared to the higher molecular weight formulation C (denoted as B-ITX-124-1) demonstrated an immediate release opportunity in the animal model.

Figure 16:
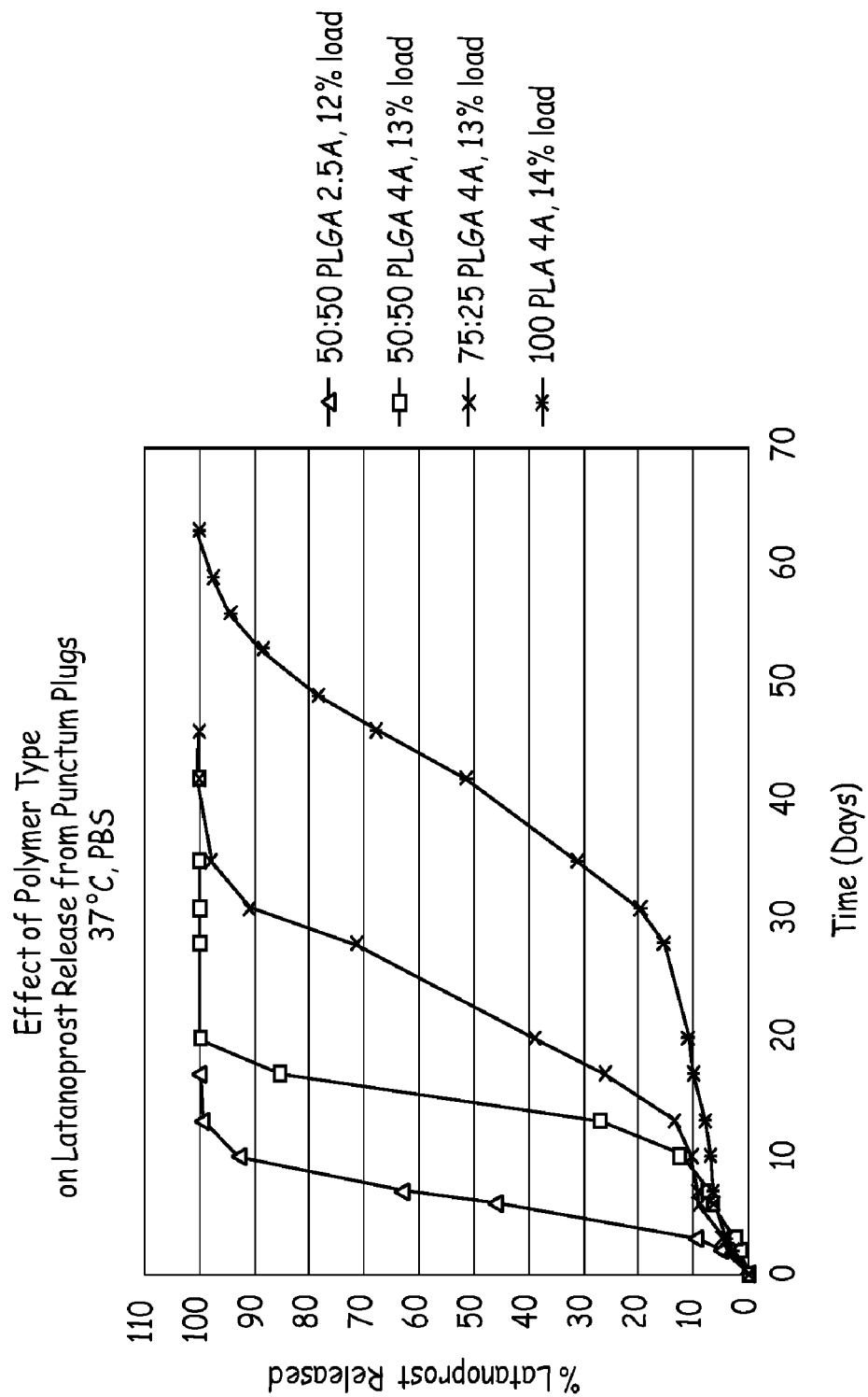
FIG. 16 is a plot showing release profiles for various embodiments of microspheres, as detailed in Example 20.
Figure 17A:
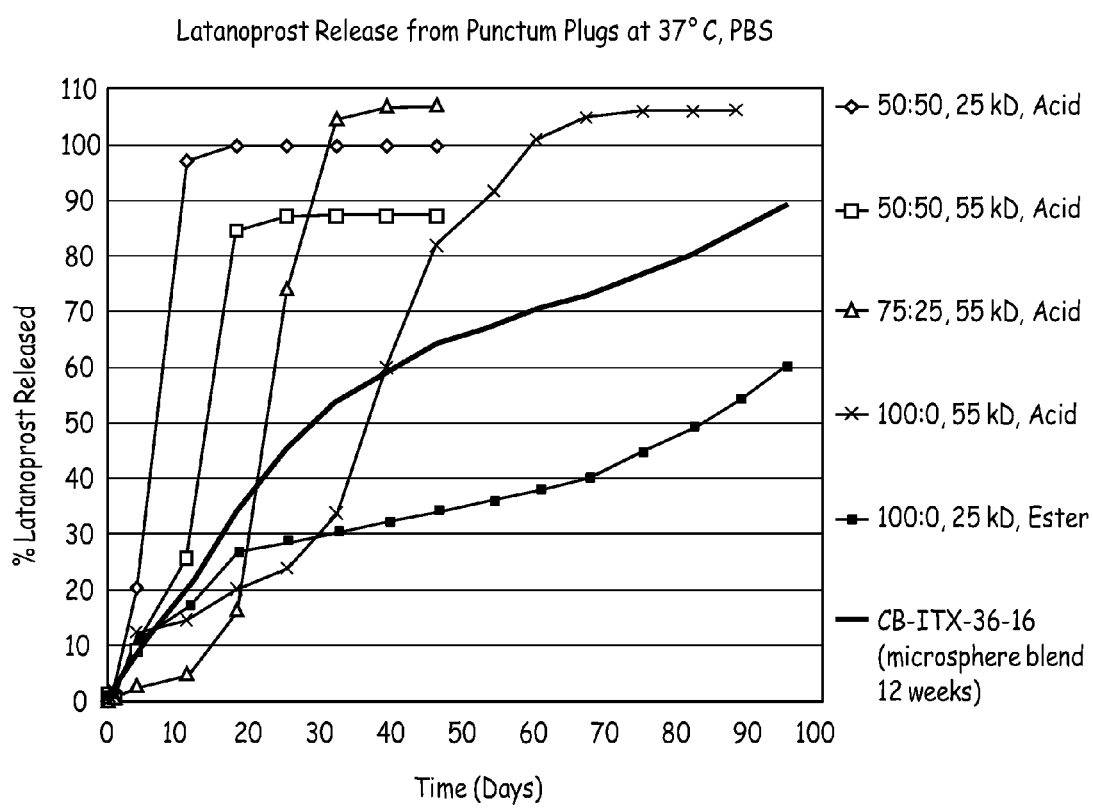
FIG. 17A provides an example of the effects of blending multiple types of polymers containing the same agents, as detailed in Example 20.
Figure 17B:
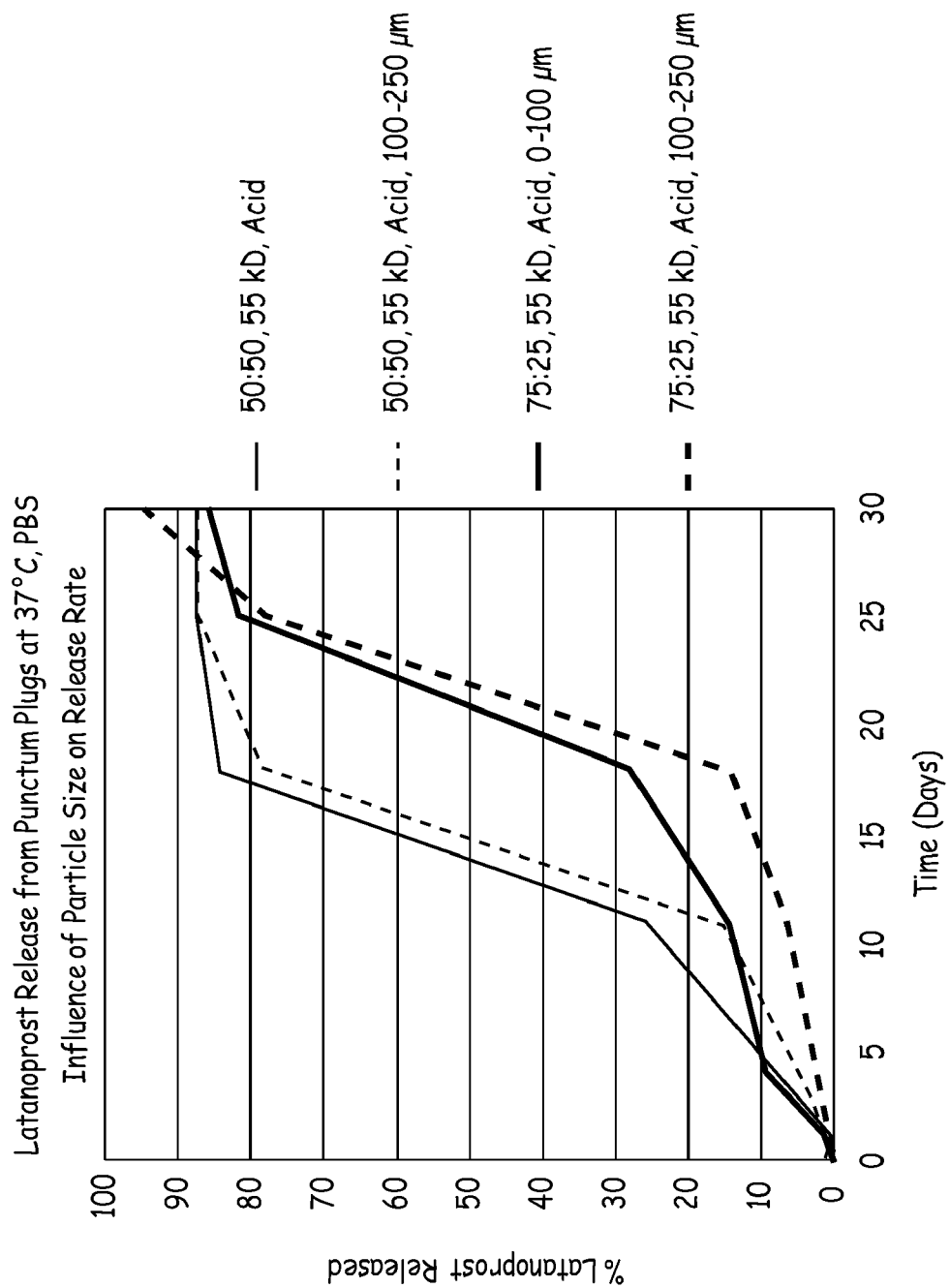
FIG. 17B provides an example of the effects of particle size range.
Figure 17C:
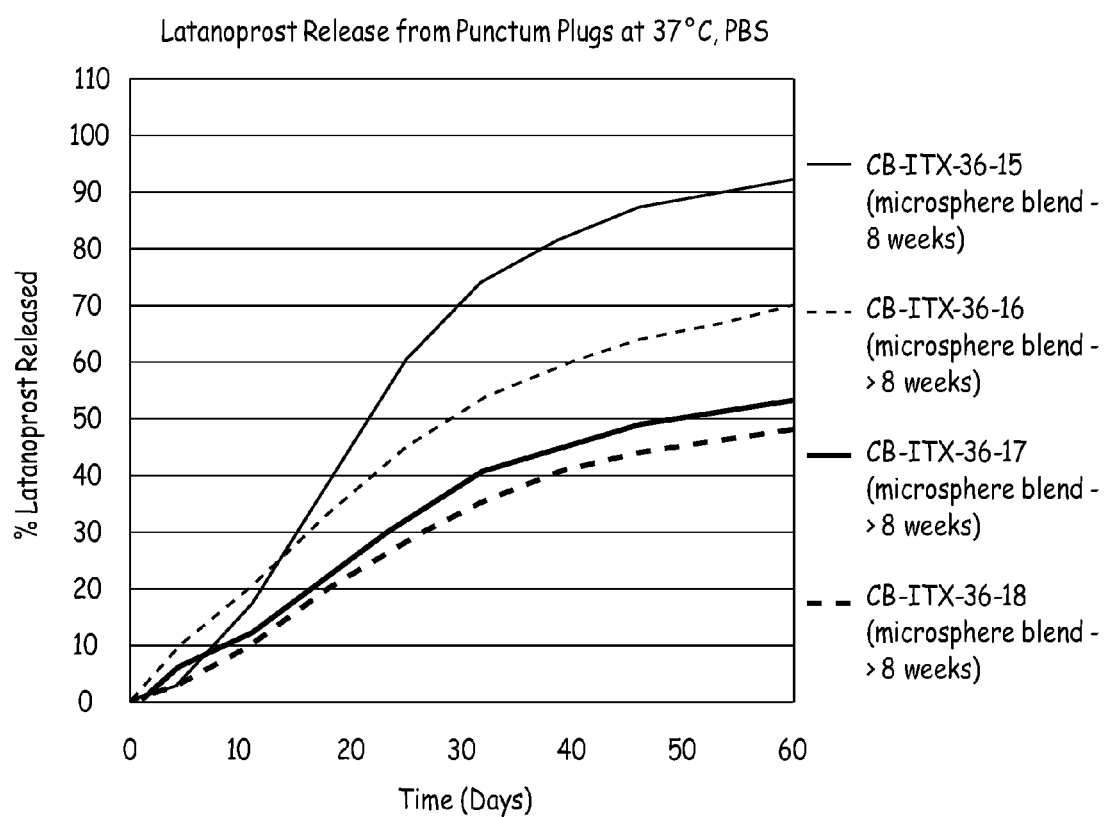
FIG. 17C provides an example of the effects of blending multiple microspheres.

Further investigation of polymeric variations in microsphere content showed that release kinetics for other drugs (latanoprost) could also be manipulated, as at FIG. 16 (Example 20). FIGS. 17A, 17B, and 17C detail how it was in fact possible to balance the competing design factors to blend microsphere sizes and compositions to obtain desired control release rates.

Figure 18:
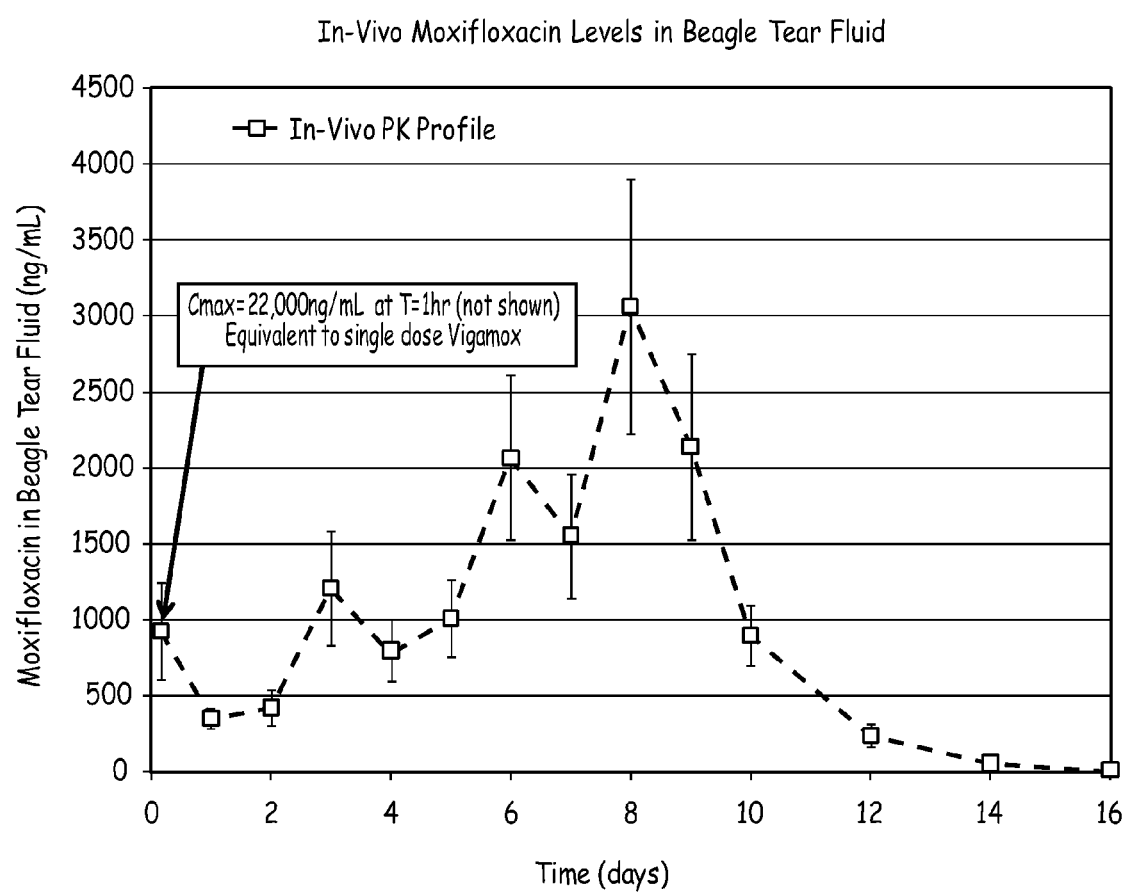
FIG. 18 depicts pharmacokinetic data for drug release from a hydrogel as detailed in Example 21.
Figure 19:
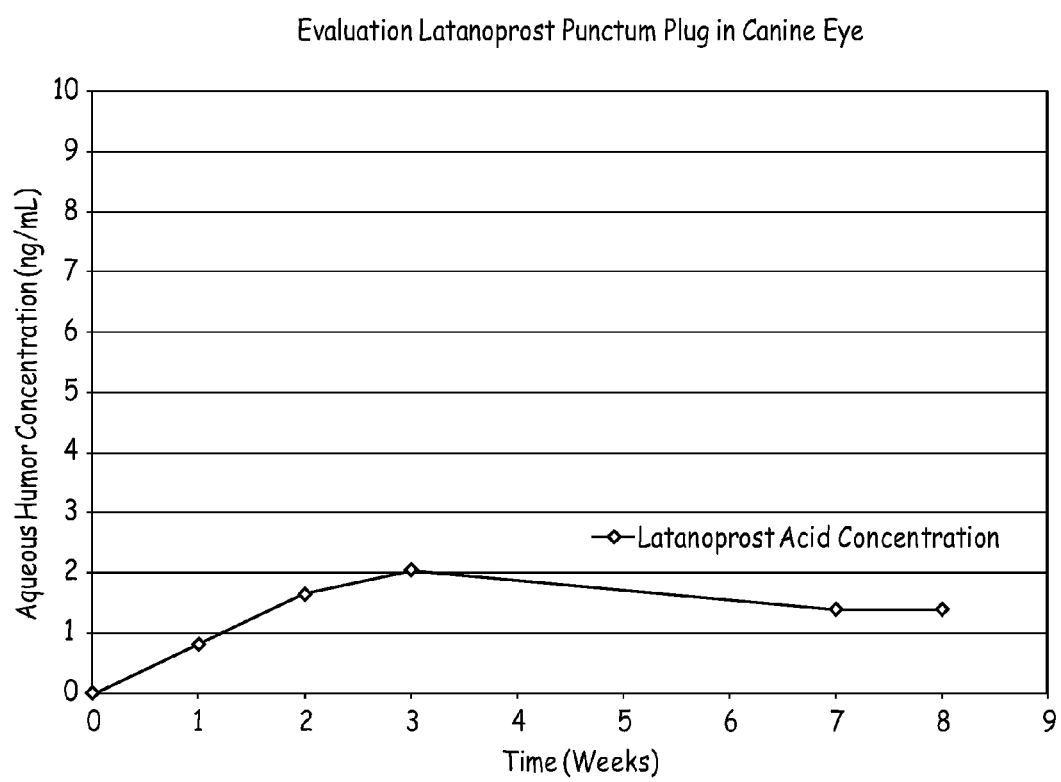
FIG. 19 depicts pharmacokinetic data for drug release from a hydrogel as detailed in Example 22.

Testing in animals showed that a punctal plug system could in fact deliver drugs over a predetermined time and that a tear film could receive the drug and build a concentration with a high initial elevation and then a sustained effective amount of drug, as demonstrated in FIGS. 18 and 19 (Examples 21 and 22). The canaliculus provides a limited volume for receiving a plug so that the total volume of drug, the release rates, the effective threshold concentrations, and duration of retention that makes the application clinically desirable, and the necessary hydrogel volume for restraining the plug therein were limiting and competing factors. One aspect of this puzzle is the loading (expressed as a percentage w/w) of the hydrogels, with a higher load affecting longevity, release rates, eye dosages, kinetics, and also mechanical integrity, i.e., there is a limit to what loading can be achieved. Therefore the unpredictability of this result is to be appreciated.

Figure 20:
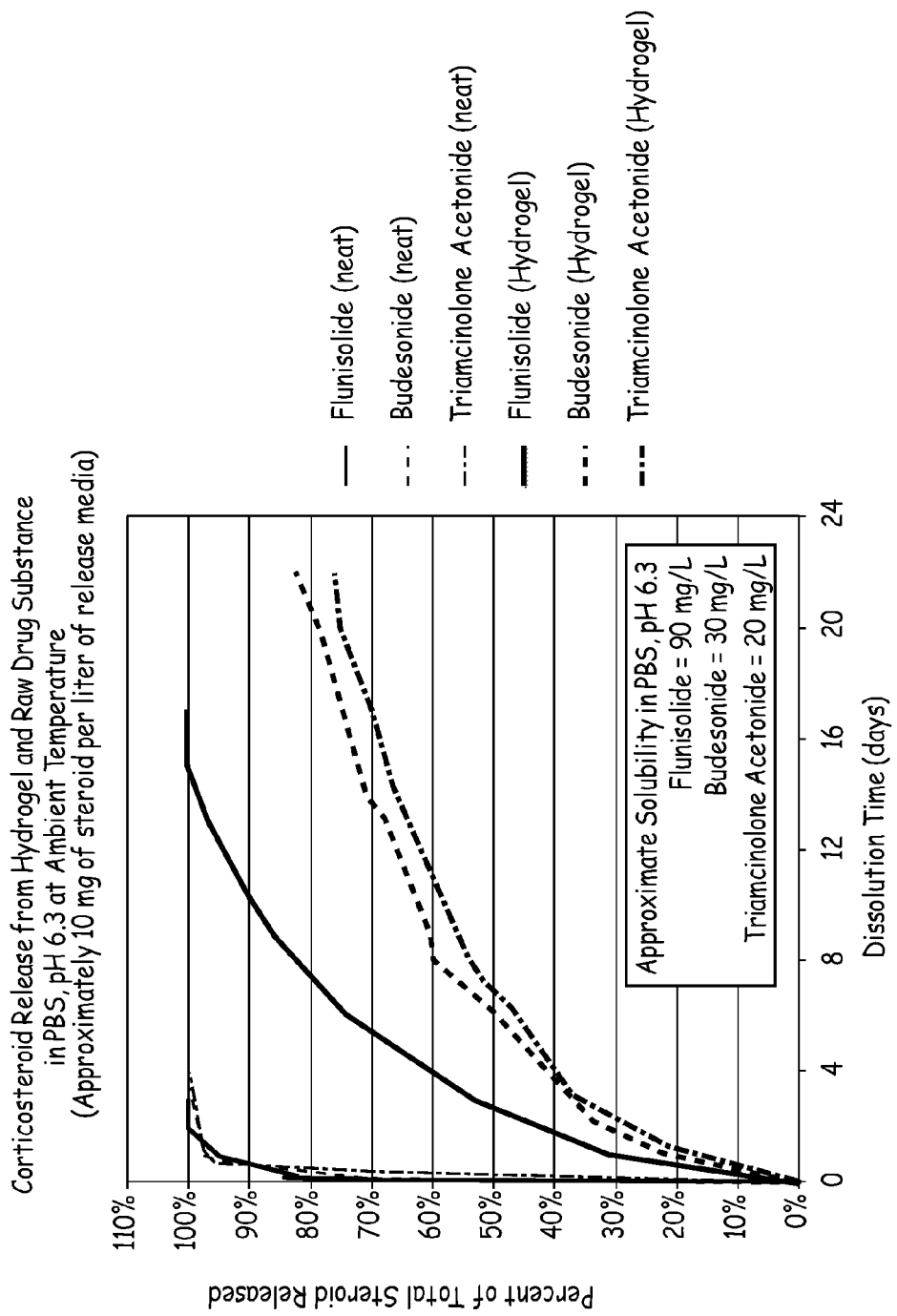
FIG. 20 is a plot showing in-vitro release of drugs entrapped in hydrogel compared to drug substance alone in saline solution, with the hydrogel affecting the rate of release, as detailed in Example 23.

Further testing with additional drugs (various steroids) showed further release kinetics control (FIG. 20).

Another challenge in the use of the hydrogel-microparticulate systems has been the breakage of the hydrogels during processing. It has been determined that a variable that effects this result is the size of the microparticles (Table 4, Example 24). Considering the pliable nature of the hydrogel systems involved, and the microscopic size of the particles, this variable was not foreseeable. Example 25 (Table 5) sets forth other results showing how variables may be manipulated to achieve a balance of the many design factors.

Figure 22:
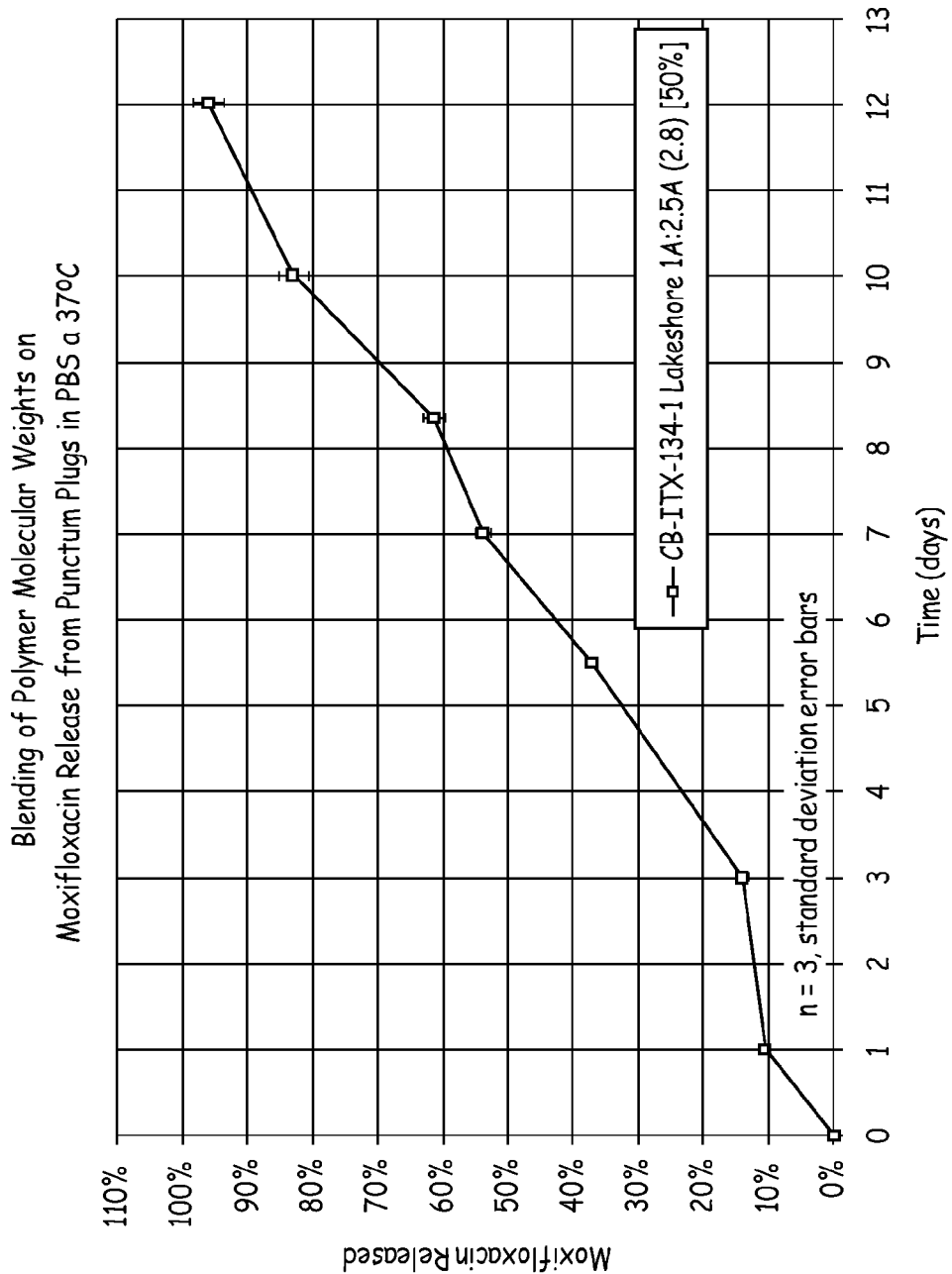
FIG. 22 is a graph demonstrating alterations of release profiles by manipulation of polymer molecular weights used to make microsphere.

Another factor that was determined to be affect the success or failure of the device was microsphere density (FIG. 22). In brief, higher density particles were found to have more of the drug, and techniques were developed to make the higher density molecules, bearing in mind the interrelatedness of manipulable factors on the overall performance of the device.

EXAMPLES

Example 1

Organic-Solvent-Based Manufacture of Pre-Formed Device

A first protocol based on drugs miscible in an organic solvent was developed as follows. 90 mg of 8-armed 15,000 molecular weight polyethylene glycol with succinimidyl glutarate at each arm terminus (8a15K PEG SG) was dissolved with 6.7 mg of trilysine in 329.1 mg of methanol (MeOH) containing 24.2 mg of drug substance. This correlates to a 20% concentration of polymer in the MeOH solution, and a 20% w/w drug loading in the final dried punctum plug.

The solution is drawn into silastic tubing with a known diameter, closed with a clip, and held vertical until the crosslinking reaction is complete. The clips are removed, and the gel filled tubes placed into a vacuum chamber. The gels are dried for 24 hours at 100 mTorr and removed the following day. The dried plugs are removed from the silastic tubing, and cut to size; the optimal length ranges between 2.0 and 4.0 mm.

This method may be used for loading of non-water soluble drugs, or incorporation of encapsulated drugs tolerant to the organic phase.

Example 2

Methanol-Based Manufacture of Pre-Formed Device 90 mg of 8a15K PEG SG was dissolved with 6.7 mg of trilysine in 353.3 mg of MeOH. This correlates to a 20% concentration of polymer in the MeOH solution. The solution is drawn into silastic tubing with a known diameter, closed with a clip, and remains vertical until the crosslinking reaction is complete. The clips are removed, and the gel filled tubes placed into a vacuum chamber. The gels are dried for 24 hours at 100 mTorr and removed the following day. The dried plugs are removed from the silastic tubing, and cut to size; the optimal length ranges between 2.0 and 4.0 mm.

The pre-formed devices are added to a solvent such as MeOH, known to swell cross-linked ITX hydrogels. The MeOH contains dissolved drugs at high concentrations. Plugs are allowed to swell with organic drug solution, causing some drug to permeate into the hydrogel matrix. Gels are removed, and either dried again as above, or placed into a non-solvent such as hexane. This causes the MeOH to leave the gel and the drug to precipitate out in the gel matrix, leaving a drug loaded plug.

This method is suitable, e.g., for loading of drugs incompatible with the crosslinking technology, such as drugs with primary amines. This separates drug loading and crosslinking steps to remove problems with incompatibility.

Example 3

Aqueous-Based Manufacture of Pre-Formed Device 90 mg of 8a15K PEG SG was dissolved with 6.7 mg of trilysine in 329.1 mg of water containing 24.2 mg of a suspension of drug. This correlates to a 20% concentration of polymer in the MeOH solution, and a 20% w/w drug loading in the final dried punctum plug. The drug suspension may be, e.g., insoluble drug particles or a suspension of encapsulated drug formulation.

The solution is drawn into silastic tubing with a known diameter, closed with a clip, and held vertical until the crosslinking reaction is complete. The clips are removed, and the gel filled tubes placed into a vacuum chamber. The gels are dried for 24 hours at 100 mTorr and removed the following day. The dried plugs are removed from the silastic tubing, and cut to size; the optimal length ranges between 2.0 and 4.0 mm.

This method is suitable for, e.g., loading of drugs encapsulated in other polymer systems. The aqueous based manufacture may be used to avoid extraction of the encapsulated drug, which could occur with some organic solvents.

Example 4

Liquid In Situ Formed Device

8a15K PEG SG polymer is dissolved at a 20% concentration in a low pH (4.0) diluent solution) containing the small molecular weight trilysine crosslinker. This solution is activated by combination with a higher pH solution (8.8), initiating the gelation mechanism. Drug is pre-loaded as a suspension in the diluent solution. The drug suspension may consist of, e.g., insoluble drug particles or a suspension of encapsulated drug formulation.

The solution is applied to the vertical canaliculus, or drawn into a small 1 cc syringe with a 27 G cannula and injected into the vertical canaliculus. The gel forms in-situ. Due to the high polymer concentration, the formulation swells significantly, providing a custom fit to the canaliculus.

Example 5

Microsphere Formation

In general, microspheres were prepared by solvent evaporation incorporating latanoprost as the drug substance. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily typically soluble in organic solvents useful for fabrication of microspheres using solvent evaporation.

Approximately 250 mg of PLGA (50:50 lactide:glycolide ratio, ~60 kD molecular weight, Lakeshore Biomaterials, Inc.) was dissolved in 1.67 mL of methylene chloride. This solution was added to approximately 25 mg of latanoprost and mixed until homogeneous. The drug/polymer solution was then injected over an approximate 20 second period through a 25-gauge needle into a 150-mL beaker containing 67 mL of 1.5% polyvinyl alcohol (31-50 kD, 89% hydrolyzed) in water for injection (WFI) while stirring a 300 rpm using a 1 inch stir bar. The solution was stirred overnight for approximately 18 hours to evaporate the solvent. The microspheres were collected on a membrane filter under vacuum and rinsed 3 times with 50 mL of WFI. The washed microspheres were then transferred to a 20 mL scintillation in a an approximate volume of 3 mL, and this vial was frozen and subsequently lyophilized over the weekend to dry the microspheres, prior to incorporation into the punctum plugs. A representative photograph of the microspheres is shown in FIG. 6.

Example 6

Microsphere Formation

This process is similar to Example 5, plus methylene chloride is to be added to the continuous phase to attain a 1% concentration. This addition will reduce the transfer rate of solvent from the discontinuous to the continuous phase and will result in tighter skin formation.

Examples 7-9

Fabrication of Polymer Wafers/Films Via Solvent Casting

Approximately 200 mg of PLGA (50:50 lactide:glycolide ratio, ~60 kD molecular weight, Lakeshore Biomaterials, Inc.) was dissolved in 1 mL of methylene chloride. This solution was added to approximately 10 mg of latanoprost and mixed until homogeneous in a 20 mL scintillation vial. The solvent from the drug/polymer solution was then allowed to evaporate for approximately 72 hours in a fume hood. The resulting film was then additionally dried overnight at ambient temperature under vacuum. Similarly, these methods may be performed using acetone and chloroform as the solvent, respectively.

Example 10

Swelling Capabilities, Pre-Formed Plug

Plugs were manufactured using the methods of Example 1 or Example 3. The branched polyethylene glycol was 8-armed 15,000 MW terminated with succinimidyl glutarate (8a15KSG). The nucleophilic precursor was trilysine. The hydrogel was crosslinked in methanol (MeOH) or water (WFI). Percent changes due to swelling are valued as changes in the specified dimensions, such as length or width of the plug, as a function of time. The amount of solids in the hydrogel at the time of formation of the hydrogel was varied from 10% to 30%. As shown in FIG. 7, unconstrained volume changes at equilibrium were obtained that ranged from about 500% to about 1200% depending on the solvent at time of formation or solids content.

Example 11

Erodible Punctal Plug, 8A15kSG

Figure 8:
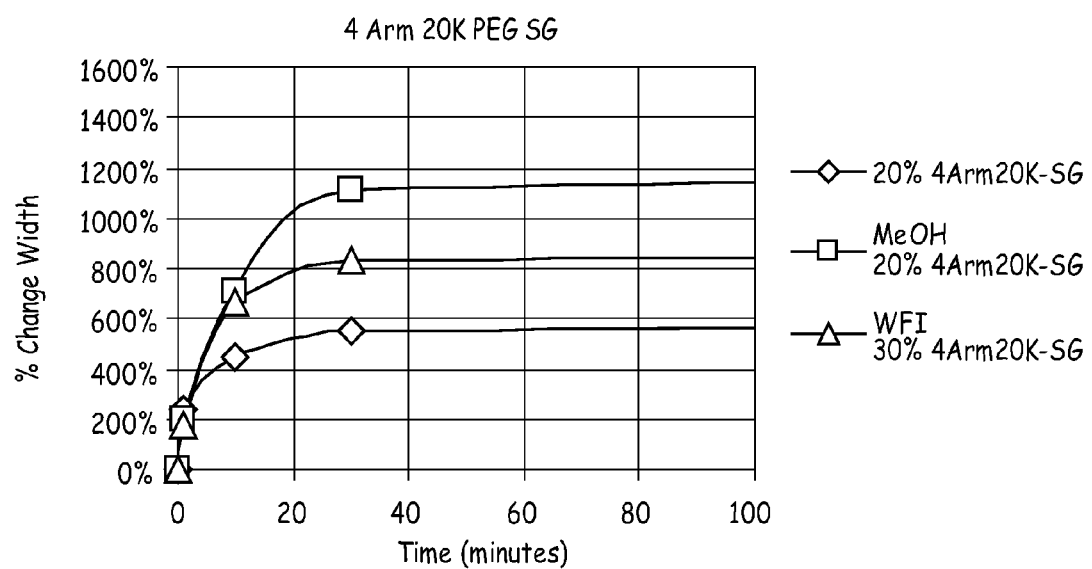
FIG. 8 is a graph of dimensional changes of punctal plugs, as detailed in Example 11.

Plugs were manufactured using the methods of Example 1 or Example 3. The branched polyethylene glycol was 4-armed 20,000 MW terminated with succinimidyl glutarate (4a15KSG). The nucleophilic precursor was trilysine. The hydrogel was crosslinked in methanol (MeOH) or water (WFI). Percent changes due to swelling are valued as changes in the specified dimensions, such as length or width of the plug, as a function of time. The amount of solids in the hydrogel at the time of formation of the hydrogel was varied from 20% to 30%. As shown in FIG. 8, unconstrained dimensional changes at equilibrium were obtained that ranged from about 500% to about 1200% depending on the solvent at time of formation or solids content.

Example 12

Figure 9:
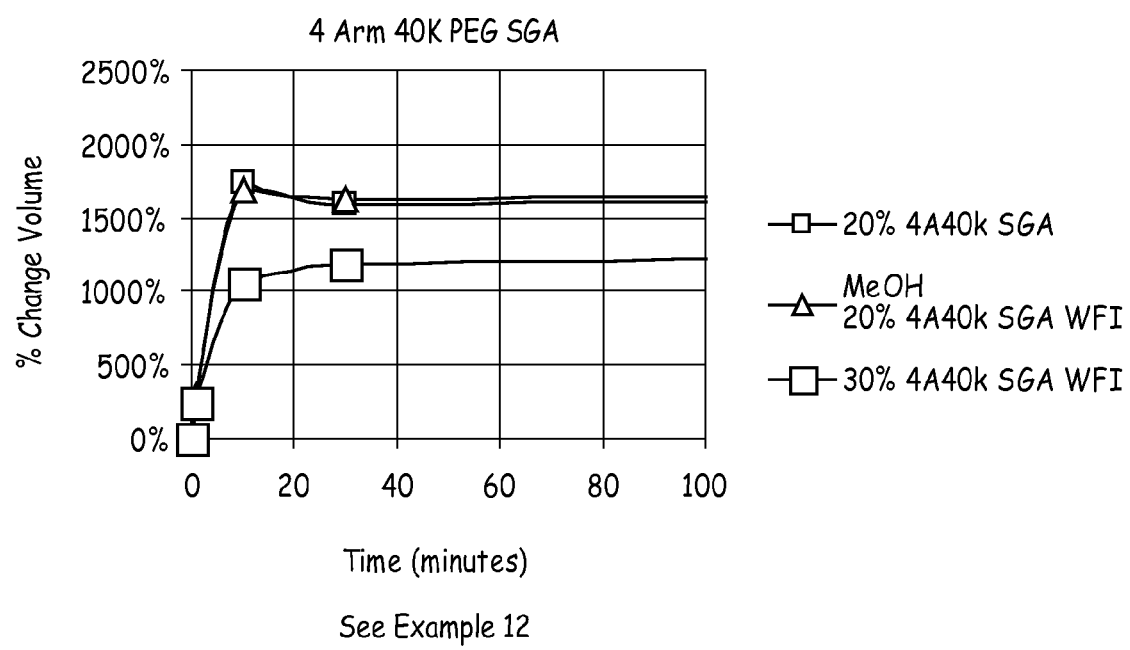
FIG. 9 is a graph of volume changes of variously formed punctal plugs, as detailed in Example 12.

Plugs were manufactured using the methods of Example 1 or Example 3. The branched polyethylene glycol was 4-armed 20,000 MW terminated with succinimidyl glutaramide (4a20KSGA). The nucleophilic precursor was trilysine. The hydrogel was crosslinked in methanol (MeOH) or water (WFI). Percent changes due to swelling are valued as changes in the specified dimensions, such as length or width of the plug, as a function of time. The amount of solids in the hydrogel at the time of formation of the hydrogel was varied from 20% to 30%. As shown in FIG. 9, unconstrained dimensional changes at equilibrium were obtained that ranged from about 1100% to about 1700% depending on the solvent at time of formation or solids content.

Example 13

PLGA Encapsulated 8A15kSG Punctum Plug

Hydrogels were manufactured using the methods of Example 3, with the hydrogels being made in water in the absence of a therapeutic agent. An 8-armed 15,000 MW polyethylene glycol with succinimidyl glutarate termini was reacted with trilysine. The hydrogel was loaded with latanoprost or latanoprost-containing microspheres made according to Example 5. As shown in FIG. 10, neat latanoprost that was not encapsulated was released from the hydrogel at an effectively zero-order release profile until it reached about 90% delivery. Hydrogels loaded with 300 micrometer microspheres did not release the agent until about day 6 and then released over time with a large portion of that time being approximately zero-order release. Similarly, films cast from dichloromethane had a similar but distinct profile.

Example 14

Cyclosporine

Hydrogels were manufactured using the methods of Example 1, with cyclosporine being pre-dissolved in the organic medium used to make the hydrogel, and without encapsulation. One of the unexpected results reported herein is that increased drug loading can cause slower release, which runs counter to expectations in drug delivery. As shown in FIG. 11, the rate of release as a percentage of the total release was unexpectedly faster for lower-loaded plugs than higher-loaded plugs.

Example 15

Aqueous-Based Manufacture of Pre-Formed Device—Short Term 432 mg of 4A20kSG was weighed into a 10 mL syringe and mixed with 1.2 mL of a 1.7% moxifloxacin solution (400 mg of moxifloxacin base in 20 mL of WFI adjusted to pH 4.5 with 1N HCl). Excess air was removed. In a second syringe, 2 g of Moxifloxacin Microspheres mixed with 2.4 mL of a 1.7% moxifloxacin solution (400 mg of moxifloxacin base in 20 mL of WFI adjusted to pH 4.5 with 1N HCl). These two syringes were combined by exchange of material slowly back and forth between the syringes. Material was collected into a single 10 mL syringe. In a $3^{rd}$ syringe, 1.2 mL of a trilysine solution (31.2 mg of trilysine dissolved in 3 mL sodium phosphate dibasic) was added. This was exchanged with the previously mixed syringe, then injected into silastic tubing with a known diameter, closed with a clip, and suspended until the crosslinking reaction is complete. The clips are removed, and the gel/silastic tubing is stretched at 2.5× its original length. This is allowed to dry for 48 hours at 30° C. Stock dried plug is removed and cut to 3.5-4.5 mm lengths. This method is suitable for loading of drugs encapsulated in other polymer systems.

Example 16

Aqueous-Based Manufacture of Pre-Formed Device—Longer Term 432 mg of 4A20kSAP was weighed into a 10 mL syringe and mixed with 1.2 mL of a WFI (adjusted to pH 4.5 with sodium phosphate monobasic). Excess air was removed. In a second syringe, 2 g of Latanoprost Microspheres mixed with 2.4 mL of a WFI (adjusted to pH 4.5). These two syringes were combined by exchange of material slowly back and forth between the syringes. Material was collected into a single 10 mL syringe. In a $3^{rd}$ syringe, 1.2 mL of a trilysine solution (31.2 mg of trilysine dissolved in 3 mL of sodium phosphate dibasic) was added. This was exchanged with the previously mixed syringe, then injected into silastic tubing with a known diameter, closed with a clip, and suspended until the crosslinking reaction is complete. The clips are removed, and the gel/silastic tubing is stretched at 2.5× its original length. This is allowed to dry for 48 hours at 30° C. Stock dried plug is removed and cut to 3.5-4.5 mm lengths.

Example 17

Fabrication of Microspheres

Microspheres were prepared by solvent evaporation incorporating latanoprost or moxifloxacin as the drug substance. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation. Moxifloxacin is the active ingredient in VIGA-MOX, which is a fluoroquinolone approved for use to treat or prevent ophthalmic bacterial infections. Moxifloxacin is readily soluble in aqueous solutions. Thus both a hydrophobic and a hydrophilic agent are exemplified in microsphere formation.

Example 17A

Approximately 2.8 g of moxifloxacin base was dissolved in 8 mL of methylene chloride. To this, 5.18 g of 2A 50:50 PLGA was added and mixed until dissolved. The drug/polymer solution was then injected rapidly into one liter of a 0.5% poly-vinyl alcohol, 0.2% sodium phosphate dibasic, 2.5% sodium chloride solution while stirring at 880 rpm. The solution was stirred overnight for approximately 60 minutes at 40° C. to evaporate the solvent. The microspheres are washed with 8 L of WFI in 500 mL aliquots, then transferred to multiple 20 mL scintillation vials in a an approximate volume of 3 mL. These vials were frozen and subsequently lyophilized over about 48 hours to dry the microspheres, prior to incorporation into a hydrogel or other use. The dried microspheres were then incorporated into punctal plugs by mixing the components (loaded microspheres/macromer/trilysine/buffer) in a syringe and injecting into a silicone tube for hydrogel cross-linking while rolling at room temperature to prevent microspheres from settling to bottom. The tube is then stretched to a desired length and dried in the oven at 30° C. for 1 to 2 days. The dried material is removed from the tubing and cut into specific length plugs.

Example 17B

Approximately 250 mg of PLGA or PLA was dissolved in 1.67 mL of methylene chloride. This solution was added to approximately 25 mg of latanoprost and mixed until homogeneous. The drug/polymer solution was then injected over an approximate 20 second period through a 25-gauge needle into a 150-mL beaker containing 67 mL of 1.5% polyvinyl alcohol (31-50 kD, 89% hydrolyzed) in water for injection (WFI) while stirring a 300 rpm using a 1 inch stir bar. The solution was stirred overnight for approximately 18 hours to evaporate the solvent. The microspheres were collected on a membrane filter under vacuum and rinsed 3 times with 50 mL of water. The washed microspheres were then transferred to a 20 mL scintillation tube in an approximate volume of 3 mL, and this vial was frozen and subsequently lyophilized over about 48 hours to dry the microspheres, prior to incorporation into a hydrogel or other use. The following PLGA and PLA systems were utilized to produce microspheres: 1. 50:50 PLGA 2.5A; 2. 50:50 PLGA 4A; 3. 75:25 PLGA 4A; 4. 100 PLA 4A; 5. 100 PLA 2.5E; 6. 100 PLA 4.5E; 7. 100 PLA 7E. These abbreviations follow a nomenclature known to artisans and published by Lakeshore Biomaterials, with A meaning carboxylic acid end group, E meaning ester end group. The 2.5 and 4 numbers refer to the IV number (inherent viscosity of a solution in chloroform at a specific concentration) which is relative to the molecular weight. The ratios are the L:G ratio (lactide:glycolide). This nomenclature comes from the manufacturer, Lakeshore Biomaterials (division of Surmodics).

Example 17C

Similar to example 17A, plus methylene chloride is added to the continuous phase to attain a 1% concentration. This reduces the transfer rate of solvent from the discontinuous to the continuous phase by means of tighter skin formation.

Example 18

Fabrication of Polymer Wafers/Films Via Solvent Casting

Example 18A

Approximately 200 mg of PLGA (50:50 lactide:glycolide ratio, ~60 kD molecular weight, Lakeshore Biomaterials, Inc.) was dissolved in 1 mL of methylene chloride. This solution was added to approximately 10 mg of latanoprost and mixed until homogeneous in a 20 mL scintillation vial. The solvent from the drug/polymer solution was then allowed to evaporate for approximately 72 hours in a fume hood. The resulting film was then additionally dried overnight at ambient temperature under vacuum.

Example 18B

As at Example 18A, with acetone as the solvent.

Example 18C

As at Example 18A, with chloroform as the solvent.

Example 19A

In Vitro Release Short Term

Figure 14:
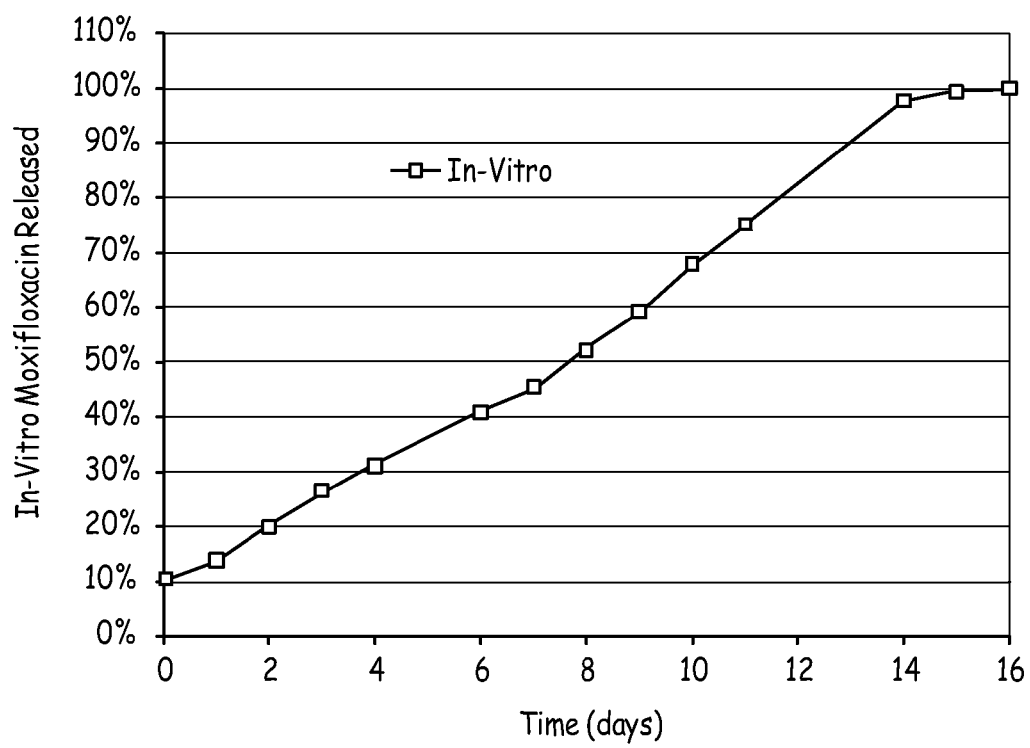
FIG. 14 is a plot showing release of drug from a hydrogel-microparticle combination, as detailed in Examples 18-19.

This Example was performed using moxifloxacin as the therapeutic agent. The in vitro release profile for a prototype moxifloxacin punctal plug like Example 17A has been evaluated at 37° C. in phosphate buffered saline (PBS). The release is shown in FIG. 14. Release from the above prototype utilized a Lakeshore 2A 50:50 PL:GA polymer for encapsulation. The fabrication and release rate kinetics is shown in FIG. 15A. FIG. 15B depicts how the release kinetics were manipulated by changing the range of particle sizes. As depicted in FIG. 15B, the broader particle range of CB-ITX-152-2 leads to longer drug release duration from the hydrogel plug compared to the smaller particle size range of formulation CB-ITX-152-10.

Example 19B

Release Profile

Modifications to Example 19A include altering the release duration and profile by changing the average molecular weight and distribution of the PLGA used during fabrication. As demonstrated in FIG. 15C, the higher molecular weight PLGA used in formulation CB-ITX-124-1 shows a pronounced lag period before sustained release can occur, whereas the lower molecular PLGA used in formulation CB-ITX-114-11 shows a linear release from day 1. A lag period has been observed to in PLGA or PLA microsphere formulations but these can be addressed by adjusting the molecular weight of the polymer and the microsphere particle size range and distribution.

Example 19C

Release Profile

Modifications to Examples 19A and 19B include altering the release duration and profile by changing both the average molecular weight and distribution of the PLGA and the polymer concentration used in the fabrication reaction. As demonstrated in FIG. 15D, by changing both the concentration and molecular weight, a formulation can be created allowing immediate release for a prolonged duration. The higher polymer concentration apparently creates a denser microsphere that may allow the release period to extend for a longer period.

The elimination of the lag period is useful particularly for immediate action therapeutics like antibiotics. The in vitro lag period observed in FIG. 15D directly translated to an in vivo lag release period in FIG. 15E. Reformulation using a lower molecular weight CB-ITX-152-2 formulation compared to the higher molecular weight formulation CB-ITX-124-1 demonstrated an immediate release in the preclinical model.

Example 20

In Vitro Release Long Term Latanoprost Plug

The in vitro release profile for the individual microsphere types used to produce the latanoprost punctum plug will vary according to the molecular weight used, composition (ratio L to G), and end group (acid vs. ester end). An example of individual release rates are shown in FIG. 16.

An example of the effects of blending multiple types of polymer containing the same agent is shown in FIG. 17. An example of the effects of blending multiple types of polymer containing the same active is shown in FIG. 17A. By blending the dried microspheres in different amounts one can tailor the release profile to the application needs. Smaller particle sizes yielded a lesser lag release period (a faster initial release) compared to the larger particle sizes, as is shown in FIG. 17B. FIG. 17C shows other effects resulting from blending.

Example 21

Relatively Shorter Duration Hydrogel

The pharmacokinetic performance of a hydrogel-and-microparticle release system was evaluated using moxifloxacin as a model. A Moxifloxacin Punctal Plug was evaluated in a canine eye model to determine in-vivo correlation of moxifloxacin release. Prototype plugs of 9% 4A20kSG containing 2A 50:50 PLGA solvent evaporation microspheres were implanted into canine inferior punctum, tear samples analyzed by LC-MS/MS over 16 days. The pharmacokinetic data is shown in FIG. 18. The pharmacokinetic profile indicates that the hydrogel punctal plug is capable of delivering to the canine eye a therapeutic amount at a constant rate in vivo for the predetermined 10 day delivery time.

A large postoperative endophthalmitis study containing bacteriological data determined that 94.2% of the confirmed growth isolates responsible for post-operative endophthalmitis were gram-positive pathogens, most commonly *Staphylococcus aureus* and *Staphylococcus epidermidis* (Han D P et al., Spectrum and susceptibilities of microbiological isolates in the Endophthalmitis Victrectomy Study, *Am J Opthalmol*, 1996; 122:1-17). The profile in FIG. 18 demonstrates tear fluid levels above the reported moxifloxacin $MIC_{90}$ for *S. aureus* (60 ng/mL) and *S. epidermidis* (130 ng/mL) for the period of 10 days (Hariprasad, S. et al., Penetration Pharmacokinetics of Topically Administered 0.5% Moxifloxacin Ophthalmic Solution in Human Aqueous and Vitreous, *Arch Opthalmology*, January 2005; 123: 39-44).

Example 22

Longer Duration Hydrogel with Microspheres

The pharmacokinetic performance of a hydrogel-and-microparticle release system was evaluated using moxifloxacin as a model. The performance of a Moxifloxacin Punctal Plug was evaluated in a canine eye model to determine in-vivo correlation of moxifloxacin release. Prototype plugs of 20% 4A20kSAP containing a blend of PLGA/PLA solvent evaporation microspheres were implanted into canine inferior punctum, tear samples analyzed by LC-MS/MS over 16 days. The pharmacokinetic data is shown in FIG. 19.

Example 23

Entrapment of Drugs into the Hydrogel Matrix

A 9% 4a20KSG hydrogel was prepared incorporating three different steroids (flunisolide, budesonide, and triamcinolone acetonide). The release profile of the steroids in the hydrogel compared to the free drug in PBS is shown in FIG. 20. It can be seen that confining or entrapping the steroid in the hydrogel results in slower more sustained drug release profile.

Example 24

Stretching and Particle Sizing

Certain embodiments relate to stretching hydrogels. It has been discovered that particle size affects the stretchable length during drying as a function of tubing size. Fabrication of punctal plugs in smaller diameter tubing and incorporating a relatively larger particle range are much more apt to fracture during the drying process resulting in unusable hydrogel plugs. By controlling the particle size range and the stretch factor for a particular tubing diameter, then hydrogel/microsphere rods can be dried successfully for subsequent cutting into, e.g., punctal plugs as is shown in Table 4. The larger particle size microspheres reduce ability of the hydrogel to be successfully stretched.

Example 26

Stretching Factors Experiments

Figure 21A:
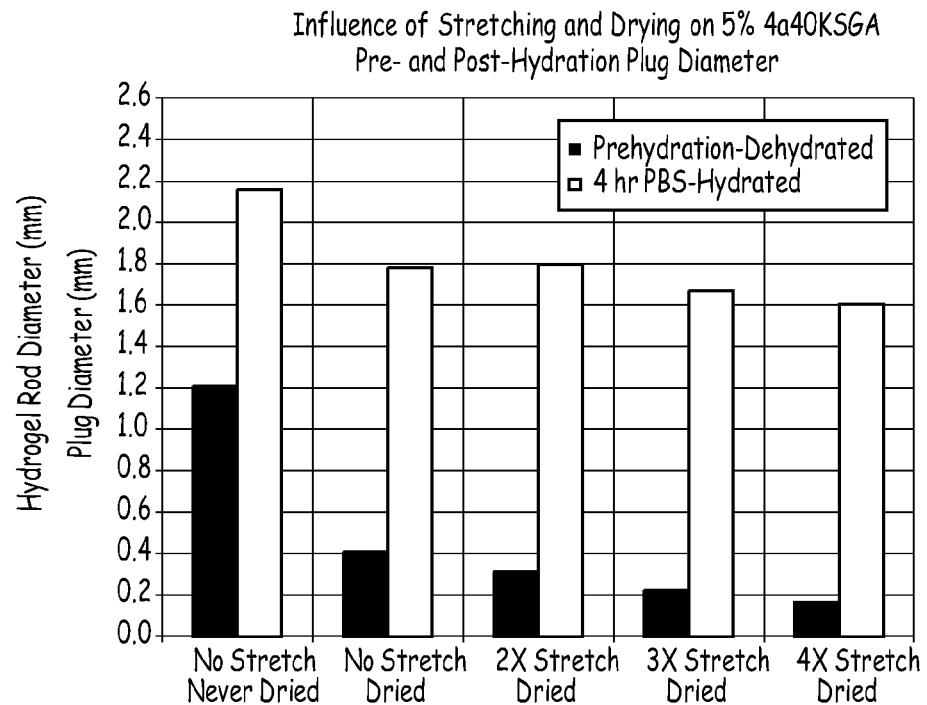
FIG. 21A relates to stretching of hydrogels.
Figure 21B:
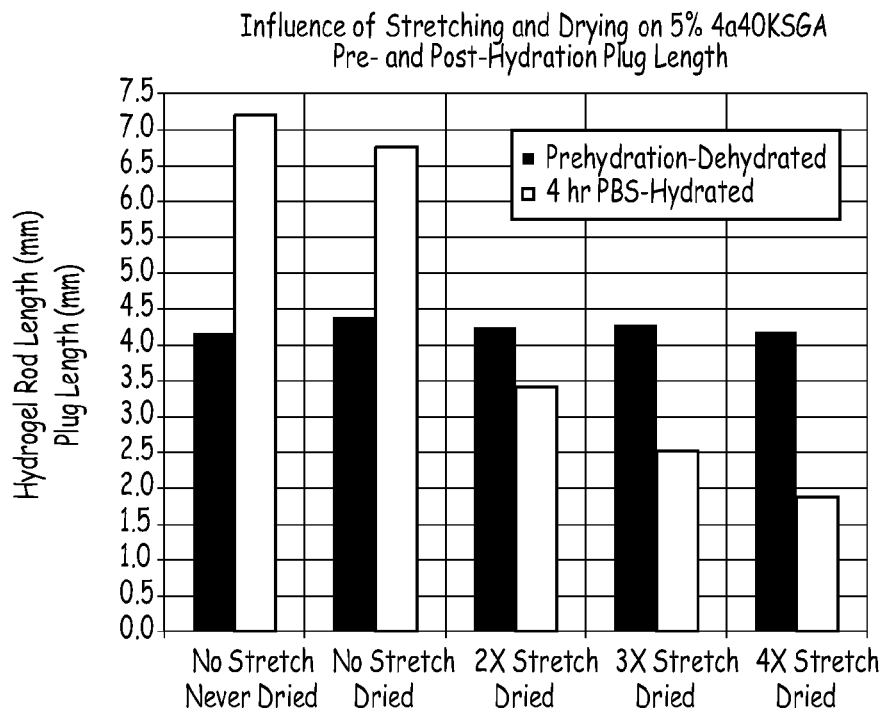
FIG. 21B relates to stretching of hydrogels.

Modifications to Example 1 include an understanding that stretch drying will result in a plug with different dried diameters to target sizes best suited for punctum plugs or other applications, but similar hydrated diameters as is demonstrated in FIG. 21A. A shorter hydrated length correlates with a greater stretch factor even though they all have a similar dried length as is shown in FIG. 21B. Therefore, it is possible to create plugs with a long dried length, but a short hydrated length as might be suitable for use in punctal plugs as the plug retracts into the canaliculus upon hydration in the punctum.

Example 27

Microsphere Polymer Weight Blending

It is possible to undertake blending of polymer weights to alter a release profile as is shown in FIG. 22. This allows a broader range of PLGA molecular weights and therefore a modification to the release profile. By incorporating greater proportions of lower molecular weight PLGA into a formulation it was possible to get a faster release or higher drug encapsulation efficiency for hydrophilic drugs. Conversely larger molecular weights provided a longer duration of release.

Denser microspheres were found to contain more agent. Microspheres prepared without sodium chloride in the PVA/continuous phase had a tapped density of 0.4 g/mL, whereas those with sodium chloride had a higher bulk tapped density of 1 g/mL. Adjustment of the density is controlled by a variety of factors but some factors were observed that markedly increased the drug encapsulation efficiency and resulted in denser microspheres. The combination of a high PLGA concentration plus a large volume (100 times the organic phase) of continuous phase containing sodium chloride yielded dense microspheres with a high encapsulation effi

TABLE 4

Influence of microsphere size, stretch factor and tubing ID on dried plug fracture.

| Microsphere Sieved Fraction (μm) | Final Polymer per Total Liquid % | Final Microspheres Load Per Total Volume | Final Microspheres Load Per Total Solids | Tubing I.D. (mm) | Stretching Drying Factor | Number of Fractures During Stretch Drying at 37° C. for 18 hours | Dried Diameter (mm) |
|---|---|---|---|---|---|---|---|
| 50-100  | 9% | 24% | 77% | 1.6 | 2.5 | 1  | — |
| 100-150 | 9% | 24% | 77% | 1.6 | 2.5 | 14 | — |
| 150-250 | 9% | 24% | 77% | 1.6 | 2.5 | 40 | — |
| 50-150  | 9% | 24% | 77% | 1.6 | 2.5 | 0  | 0.6 |
| 50-150  | 9% | 24% | 77% | 1.6 | 3.5 | 41 | — |
| 50-150  | 9% | 24% | 77% | 1.6 | 4.5 | 60 | — |

Example 25

Hydrogel Size and Parameters

Stretching, drying, drug loading, swelling, degradation, release rates, total volume, and drug dosages present competing design parameters. A feasibility experiment was performed varying microsphere loading per total plug volume, stretching factor during drying, and silicone tubing inner diameter on final plug length and estimated drug (moxifloxacin used as a model) dose per 3.5 mm length plug. Results listed in Table 5 demonstrated that a targeted plug dose of >200 μg with a final dried diameter of 0.50 mm could be achieved with a 2.5× stretch factor when prepared in a 1.47 mm ID tubing.

TABLE 5

Impact of tubing diameter, microsphere loading and stretching factor on final dried plug diameter and moxifloxacin dose per 3.5 mm plug.

| Lot: CB-ITX-152- | 18C | 18B | 17B | 14A | 16A | 14B | 15B | 16B |
|---|---|---|---|---|---|---|---|---|
| Estimated moxifloxacin plug dose (μg) | 168 | 121 | 212 | 226 | 269 | 204 | 223 | 242 |
| tubing inner diameter (mm) | 1.02 | 1.02 | 1.47 | 1.57 | 1.57 | 1.57 | 1.57 | 1.57 |
| mss load per total volume | 33.3% | 33.3% | 27.5% | 22.5% | 27.5% | 22.5% | 25.0% | 27.5% |
| stretching factor during drying | 1.8 | 2.5 | 2.5 | 2.25 | 2.25 | 2.5 | 2.5 | 2.5 |
| dried diameter (mm) | 0.44 | 0.39 | 0.51 | 0.55 | 0.64 | 0.51 | 0.54 | 0.56 | ciency (>70%). The high PLGA concentration and large volume of continuous phase result in rapid precipitation of the PLGA at the microsphere surface forming a pseudo semipermeable membrane. The addition of salt in the continuous phase increased the osmotic pressure which prevented influx of the continuous/water phase into the dispersed/organic phase and reduced the formation of channels through the microsphere surface. Additionally, sodium chloride increases the polarity of the continuous phase thereby reducing the solubility of methylene chloride in the polar continuous phase which thereby precipitates the polymer more slowly and forms relatively dense microparticles.

Additional Disclosure

1. A medical prosthesis for blocking or reducing tear flow through a punctum or canaliculus of a human eye and delivering a drug to the eye that comprises a dehydrated covalently crosslinked synthetic hydrophilic polymer hydrogel with dimensions to pass through a puncta lacriniali, with the dehydrated hydrogel absorbing physiological water to swell to at least about 1 mm in cross-sectional width (or at least about 1.5 mm or at least about 2 mm) and conformably fit a canaliculus, with the hydrogel comprising a therapeutic agent dispersed through the hydrogel for release to an eye, with the hydrogel having a water content of at least about 50% by weight or volume when allowed to fully hydrate in vitro in physiological saline. The volume of the prostheses may be, e.g, between 0.2 and 100 cubic millimeters; artisans will immediately appreciate that all the ranges and values within the explicitly stated ranges are contemplated.

2. The prosthesis of 1 wherein the dehydrated hydrogel swells to at least the 1 mm width within 10 minutes of placement in a canaliculus.

3. The prosthesis of 1 or 2 wherein the hydrogel is stretched in length and dried.

4. The prosthesis of any of 1-3 wherein the amount of stretching increases the length of the hydrogel by a factor of at least about 1 or 1.5 or 2.

5. The prosthesis of any of 1-4 further comprising a visualization agent that present in a concentration effective to provide visibility of the agent to a human without a machine-aid.

6. The prosthesis of any of 1-5 providing a substantially zero-order release kinetic for the drug, as measurable by the slope of a plot of release of the drug over time being a substantially straight line between the total cumulative release percentage at about day 2 and about 75% total cumulative release when the dehydrated hydrogel is placed into a physiological solution in vitro.

7. The prosthesis of any of 1-6 wherein the drug is encapsulated within a collection of microspheres dispersed throughout the hydrogel, with the collection being selected to have a range of particle diameters only from about 20 to about 300 microns and a size distribution that is necessary to provide the zero order release as a result of relatively smaller microspheres releasing drug more rapidly relative to larger particles within the range.

8. The prosthesis of any of 1-7 wherein the diameter range is from about 20 to about 150 microns, or 25 to 150 microns; artisans will immediately appreciate that all the ranges and values within the explicitly stated ranges are contemplated.

9. The prosthesis of any of 1-8 further comprising an additional amount of the drug, with the additional amount being dispersed within the hydrogel without encapsulation in the microspheres, with the additional amount providing an initial burst of release of the additional amount of drug, as measurable by a plot of cumulative release of the drug over time, with the initial burst being between 0% and about 35% (artisans will immediately appreciate that all the ranges and values within the explicitly stated ranges are contemplated or 10% of 20%, w/w) total drug cumulative release when the dehydrated hydrogel is placed into a physiological solution in vitro and wherein drug associated with the microspheres does not substantially contribute to the initial burst.

10. The prosthesis of any of 1-9, with the hydrogel spontaneously degrading by chemical hydrolysis in water.

11. The prosthesis of any of 1-10, consisting essentially of the hydrogel, the microspheres containing the drug, and the additional amount of the drug. Buffers and saline are not essential to the character of the invention. Alternatively, the device may consist essentially of a visualization agent, the hydrogel, and the microspheres containing the drug and/or the additional amount of the drug not in the microspheres.

12. The prosthesis of any of 1-10 wherein the drug is substantially insoluble in aqueous solution.

13. The prosthesis of any of 1-10, 12 wherein the drug is substantially soluble in aqueous solution.

14. The prosthesis of any of 1-10, 12-13 wherein the hydrogel is a reaction product of a first synthetic polymer that comprises a plurality of polymerizable groups that are polymerized by free radical initiation.

15. The prosthesis of any of 1-12, 10-14 wherein the hydrogel is a reaction product of a first synthetic water soluble polymer comprising at least three first functional groups and a second synthetic water soluble polymer that comprises at least three second functional groups, with the first and second functional groups reacting with each other to form covalent bonds and thereby form the hydrogel as a synthetic crosslinked hydrogel.

16. The prosthesis of any of 1-12, 10-15 wherein the first polymer comprises polyethylene glycol and the first functional groups are succinimides, and wherein the second functional groups are selected from the group consisting of amine and thiol.

17. The prosthesis of any of 1-12, 10-16 wherein the drug is latanoprost and the latanoprost is released in vivo from the hydrogel as placed in a canaliculus in an amount effective to reduce elevated intraocular pressure in patients suffering from open angle glaucoma or ocular hypertension over a time of at least about four weeks, with the hydrogel as swollen in place having a volume of no more than about 1 cubic millimeter.

18. The prosthesis of any of 1-10 or 10-17 wherein the drug is moxifloxacin and the moxifloxacin is releasable in vivo from the hydrogel into a tear film of an eye as placed in a canaliculus in an amount effective to substantially reduce *S. aureus* or *S. epidermidis* at the eye over a time of at least about six days, with the hydrogel as swollen in place having a volume of no more than about 1 cubic millimeter.

19. The prosthesis of 18 wherein the moxifloxacin is in a base form.

20. A process for making a prosthesis for blocking or reducing tear flow through a punctum or canaliculus of a human eye and delivering a drug to the eye comprising forming a plurality of microspheres from hydrolytically degradable materials, with the microspheres containing the drug, washing the microspheres, separating the microspheres to obtain a collection of microspheres with a diameter range of between about 20 and about 300 microns, mixing the microspheres with a synthetic polymer hydrogel precursor and forming a hydrogel from the precursor inside a tube, with the microspheres being dispersed throughout the hydrogel, extruding the hydrogel from the tube, stretching the hydrogel length by a factor of at least about 2 (or at least 1.5 or at least 2.5 or from between 1 and 3; artisans will immediately appreciate that all the ranges and values within the explicitly stated ranges are contemplated), with the resultant maximum cross-sectional width of the hydrogel being less than about 1 mm, dehydrating the hydrogel, cutting or breaking the dried hydrogel into lengths of less than about 5 mm, and selecting a distribution of microsphere diameters within the range for the collection to display substantially zero-order release kinetic for the drug, as measurable by the slope of a plot of release of the drug from the prosthesis over time being a substantially straight line between about the total cumulative percentage drug release at about day 2 and about 75% total cumulative release when the dehydrated hydrogel prosthesis is placed into a physiological solution in vitro; with the dehydrated hydrogel absorbing physiological water to swell to at least 1 mm in cross-sectional width and conformably fit a cannaliculus, and with the hydrogel having a water content of at least about 50% by weight or volume when allowed to fully hydrate in vitro in physiological saline.

21. The process of 20 wherein the dehydrated hydrogel swells to at least the 1 mm width within 10 minutes of placement in a canaliculus.

22. The process of 20 or 21 further comprising placing a visualization agent into the hydrogel at a concentration effective to provide visibility of the prosthesis to a human without a machine-aid.

23. The process of any of 20-22 further comprising mixing an additional amount of the drug within the hydrogel without encapsulation in the microspheres, with the additional amount providing an initial burst of release of the additional amount of drug, as measurable by a plot of cumulative release of the drug over time, with the initial burst being between 0% and about 35% total drug cumulative release when the dehydrated hydrogel is placed into a physiological solution in vitro and wherein drug associated with the microspheres during microsphere manufacture or loading does not substantially contribute to the initial burst.

24. The process of any of 20-23 wherein the hydrogel spontaneously degrades by chemical hydrolysis in water.

25. The process of any of 20-24 wherein the hydrogel is a reaction product of a first synthetic polymer that comprises a plurality of polymerizable groups that are polymerized by free radical initiation.

26. The process of any of 20-25 wherein the hydrogel is a reaction product of the synthetic polymer hydrogel precursor that further comprises at least three first functional groups and a second synthetic water soluble polymer that comprises at least three second functional groups, with the first and second functional groups reacting with each other to form covalent bonds and thereby form the hydrogel as a synthetic crosslinked hydrogel.

27. A method comprising using any of the 1-26.

28. A process comprising making any of the prostheses of 1-26.

29. A use or method of using a prosthesis or process of any of 1-28 wherein the drug is latanoprost and the latanoprost is released in vivo from the hydrogel as placed in a canaliculus in an amount effective to reduce elevated intraocular pressure in patients suffering from open angle glaucoma or ocular hypertension over a time of at least about four weeks.

30. A use or method of using a prosthesis or process of any of 1-28 method wherein the drug is moxifloxacin and the moxifloxacin is released in vivo from the hydrogel into a tear film of an eye as placed in a canaliculus in an amount effective to substantially reduce S. aureus or S. epidermidis at the eye over a time of at least about six days.

31. A use or method of using a drug set forth herein to treat the condition associated therewith, or to make a medicament therefor.

32. A medicament as in any of 1-30, or formed thereby.

33. A microsphere as set forth herein placed subconjunctivally for delivery of a drug from said microsphere, a medicament or use thereof, or a therapeutic method of using the same in a patient.

The headings and subheadings in this specification are intended to be for the convenience of the reader. These do not in any way limit the disclosure or embodiments within a section. Various embodiments with particular features have been set forth. These various features may be freely mixed-and-matched by the artisan skilled in these arts, as guided by the need to make a workable device.

The invention claimed is:

1. A medical prosthesis for blocking or reducing tear flow through a punctum or canaliculus of a human eye and delivering a drug to the eye that comprises:
   a punctal plug comprising a dehydrated covalently crosslinked synthetic hydrophilic polymer hydrogel wherein the hydrogel precursors are first covalently cross-linked to form the hydrogel and then stretched in length and dried, with the plug having dimensions to pass through a puncta lacrimali, and with the dehydrated hydrogel absorbing physiological water to swell to at least 1 mm in cross-sectional width to expand the plug to conformably fit a canaliculus, with the hydrogel thereby directly contacting tissue of the canaliculus in the expanded state and having a proximal face in fluid communication with a tear film of the eye and with the punctal plug further comprising a therapeutic agent dispersed through the hydrogel for sustained release through the proximal face to the tear film of the eye in an effective amount over a period of at least about seven days,
   with the hydrogel having a water content of at least about 50% by weight or volume when allowed to fully hydrate in vitro in physiological saline and being free of polysaccharides.

2. The prosthesis of claim 1 wherein the dehydrated hydrogel swells to at least the 1 mm width within 10 minutes of placement in a canaliculus.

3. The prosthesis of claim 1 wherein the amount of stretching increases the length of the hydrogel by a factor of at least about 1.5.

4. The prosthesis of claim 1 further comprising a visualization agent that is present while the hydrogel is present and is in a concentration effective to provide visibility of the agent to a human without a machine-aid.

5. The prosthesis of claim 1 providing a sustained release of the therapeutic agent into the tear film to provide a concentration of the agent in the tear film of at least about 50 ng/mL for at least the seven days.

6. The prosthesis of claim 1 wherein the therapeutic agent is encapsulated within microspheres dispersed throughout the hydro gel, with the microspheres being a blend of a plurality of microsphere collections, with the collections having distinct material compositions and distinct drug release rate profiles.

7. The prosthesis of claim 6 wherein a diameter range of the microspheres is from about 20 to about 150 microns.

8. The prosthesis of claim 6 further comprising an additional amount of the therapeutic agent, with the additional amount being dispersed within the hydrogel without encapsulation in the microspheres, with the additional amount providing an initial burst of release of the additional amount of therapeutic agent, as measurable by a plot of cumulative release of the therapeutic agent over time, with the initial burst being between hydrogel is placed into a physiological solution in vitro and wherein therapeutic agent associated with the microspheres does not substantially contribute to the initial burst.

9. The prosthesis of claim 6, with the hydrogel and agent-loaded microspheres being spontaneously degradable by hydrolysis of covalent bonds in water.

10. The prosthesis of claim 1, consisting essentially of the hydrogel and microspheres containing the therapeutic agent.

11. The prosthesis of claim 8 wherein the therapeutic agent is substantially insoluble in aqueous solution.

12. The prosthesis of claim 8 wherein the therapeutic agent is substantially soluble in aqueous solution.

13. The prosthesis of claim 1 wherein the hydrogel is a reaction product of a first synthetic polymer that comprises a plurality of polymerizable groups that are polymerized by free radical initiation.

14. The prosthesis of claim 1 wherein the hydrogel is a reaction product of a first synthetic water soluble polymer comprising at least three first functional groups and a second synthetic water soluble polymer that comprises at least three second functional groups, with the first and second functional groups reacting with each other to form covalent bonds and thereby form the hydrogel as a synthetic crosslinked hydrogel.

15. The prosthesis of claim 14 wherein the first polymer comprises polyethylene glycol and the first functional groups are succinimides, and wherein the second functional groups are selected from the group consisting of amine and thiol.

16. The prosthesis of claim 1 wherein the therapeutic agent comprises a prostaglandin analogue that is released in vivo from the hydrogel as placed in a canaliculus in an amount effective to reduce elevated intraocular pressure in patients suffering from open angle glaucoma or ocular hypertension over a time of at least about four weeks.

17. The prosthesis of claim 1 wherein the therapeutic agent comprises moxifloxacin and the moxifloxacin is releasable in vivo from the hydrogel into a tear film of an eye as placed in a canaliculus in an amount effective to substantially reduce *S. aureus* or *S. epidermidis* at the eye over a time of at least about six days.

18. The prosthesis of claim 17 wherein the moxifloxacin is in a base form.

19. The prosthesis of claim 16 wherein the prostaglandin analogue comprises travoprost.

20. The prosthesis of claim 1, consisting of the hydrogel and the additional amount of and the therapeutic agent.

21. The prosthesis of claim 1, wherein, at the time of expansion, the plug has the proximal face and a distal face joined to each other by a side surface, wherein the side surface provides the hydrogel that contacts the tissue, and the side surface has an area at least twice an area of the proximal face.

22. The prosthesis of claim 4, wherein the visualization agent is present in microspheres, and/or microparticles and/or microdroplets entrapped within the hydrogel.

23. The prosthesis of claim 4, wherein the visualization agent is covalently bound to the hydrogel.

* * * * *

UNITED STATES PATENT AND TRADEMARK OFFICE
CERTIFICATE OF CORRECTION

PATENT NO. : 8,409,606 B2
APPLICATION NO. : 12/704692
DATED : April 2, 2013
INVENTOR(S) : Amarpreet S. Sawhney et al.

It is certified that error appears in the above-identified patent and that said Letters Patent is hereby corrected as shown below:

In the Claims

In Column 50, line 67, after "between" insert --0% and about 35% total therapeutic agent cumulative release when the dehydrated--.
In Column 52, line 18, after "the" delete "additional amount of and the".

Signed and Sealed this
Ninth Day of July, 2013

Teresa Stanek Rea
*Acting Director of the United States Patent and Trademark Office*